United States Patent [19]
Jacobs et al.

[11] Patent Number: 6,028,049
[45] Date of Patent: Feb. 22, 2000

[54] **COMPOSITIONS COMPRISING THE TBP2 SUBUNIT OF THE TRANSFERRIN RECEPTOR OF *NEISSERIA MENINGITIDIS***

[75] Inventors: Eric Jacobs; Michèle Legrain, both of Dorlisheim; Véronique Mazarin, Lyons; Bernadette Bouchon-Theisen, Strasbourg, all of France; Anthony B. Schryvers, Calgary, Canada; Marie-Aline Bloch, Lyons, France

[73] Assignees: Pasteur Merieux Serums et Vaccins, Lyons; Transgene S.A., Strasbourg, both of France

[21] Appl. No.: 08/448,194

[22] Filed: May 23, 1995

Related U.S. Application Data

[63] Continuation of application No. 08/361,469, Dec. 22, 1994, which is a continuation of application No. 08/078,053, Jun. 18, 1993, abandoned.

[30]  Foreign Application Priority Data

Jun. 19, 1992 [FR] France ................................. 92 07493

[51] Int. Cl.[7] .......................... C07K 14/705; A61K 38/00
[52] U.S. Cl. ............................ 514/2; 530/350; 530/395; 424/250.1; 435/69.1; 536/23.7
[58] Field of Search ................................ 514/2; 530/350, 530/395; 435/69.1; 536/23.7; 424/250.1

[56]  References Cited

U.S. PATENT DOCUMENTS

| | | | |
|---|---|---|---|
| 5,141,743 | 8/1992 | Schryvers | ................................. 424/92 |
| 5,618,541 | 4/1997 | Quentin-Millet | ..................... 424/250.1 |

FOREIGN PATENT DOCUMENTS

| | | |
|---|---|---|
| WO92/03467 | 3/1992 | WIPO . |
| WO90/12591 | 11/1992 | WIPO . |
| 9306861 | 4/1993 | WIPO . |

OTHER PUBLICATIONS

P. Stevenson et al, "Common Antigenic Domains in Transferrin–Binding–Protein 2 of *Neisseria meningitidis, Neisseria gonorrhoeae,* and *Haemophilus influenzae* Type b", Jun. 1992, *Infection and Immunity*, vol. 60, No. 6, pp. 2391–2396.

Schryvers et al., "Comparative Analysis of the Transferrin and Lactoferrin Binding Proteins in the Family Neisseriaceae", 1988, *Molecular Microbiology*, vol. 2, p. 281.

Schryvers et al., "Identification and Characterization of the Transferrin Receptor from *Neisseria meningitidis*", 1989, *Can. J. of Microbiology*, vol. 35, p. 409.

Cornelissen et al, "Gonococcal Transferrin–Binding Protein 1 is Required for Transferrin Utilization and Is Homologous to TonB–Dependent Outer Membrane Receptors", Sep. 1992, *Journal of Bacteriology* pp. 5788–5797.

Legrain et al, "Cloning and Characterization of *Neisseria Meningitidis* Genes Encoding the Transferrin–Binding Proteins Tbp1 and Tbp2", 1993, *Gene*, vol. 130, pp. 73–80.

*Primary Examiner*—Sally P. Teng
*Attorney, Agent, or Firm*—Burns, Doane, Swecker & Mathis, L.L.P.

[57]  ABSTRACT

The subject of the present invention is a DNA fragment which encodes a protein capable of being recognised by an antiserum against the transferrin receptor of the strain IM2394 or IM2169 of *N. meningitidis* as well as a process for producing the said protein by a recombinant route. By way of example, such a DNA fragment encodes the tbp1 subunit of the strain IM2394 or IM2169 or the tbp2 subunit of the strain IM2394 or IM2169.

8 Claims, 12 Drawing Sheets

```
Tbp1-2394  MQQQHLFRLNILCLSLMTALPVYAENVQAEQAQEKQLDTIQVKAKKQKTRRDNEVTGLGK
Tbp1-2169  MQQQHLFRLNILCLSLMTALPAYAENVQAGQAQEKQLDTIQVKAKKQKTRRDNEVTGLGK
           *********************.******.*******************************

Tbp1-2394  LVKSSDTLSKEQVLNIRDLTRYDPGIAVVEQGRGASSGYSIRGMDKNRVSLTVDGVSQIQ
Tbp1-2169  LVKTADTLSKEQVLDIRDLTRYDPGIAVVEQGRGASSGYSIRGMDKNRVSLTVDGLAQIQ
           ***..********* ***************************************. ***

Tbp1-2394  SYTAQAALGGTRTAGSSGAINEIEYENVKAVEISKGSNSSEYGNGALAGSVAFQTKTAAD
Tbp1-2169  SYTAQAALGGTRTAGSSGAINEIEYENVKAVEISKGSNSVEQGSGALAGSVAFQTKTADD
           ***************************************  *  ************* *

Tbp1-2394  IIGEGKQWGIQSKTAYSGKDHALTQSLALAGRSGGAEALLIYTKRRGREIHAHKDAGKGV
Tbp1-2169  VIGEGRQWGIQSKTAYSGKNRGLTQSIALAGRIGGAEALLIHTGRRAGEIRAHEDAGRGV
           .****.*************. ****.***** ********.*.**.**  **.***.**

Tbp1-2394  QSFNRLVLDEDKKEGGSQYRYFIVEEECH-NGYAACKNKLKEDASVKDERKTVSTQDYTG
Tbp1-2169  QSFNRLVPVED----SSEYAYFIVEDECEGKNYETCKSKPKKDVVGKDERQTVSTRDYTG
           *******  **    *  * *****.**   *  **.*  **   ****.****.****

Tbp1-2394  SNRLLANPLEYGSQSWLFRPGWHLDN-RHYVGAVLERTQQTFDTRDMTVPAYFTSEDYVP
Tbp1-2169  PNRFLADPLSYESRSWLFRPGFRFENKRHYIGGILEHTQQTFDTRDMTVPAFLTKAVFDA
            ** **.**.* * ******* . .*.***.*..**.**************..*.  *

Tbp1-2394  -----GSLKGLGKYSGDNKAERLFVQGEGSTLQGIGYGTGVFYDERHTKNRYGVEYVYHN
Tbp1-2169  NSKQAGSLPGNGKYAGNHKYGGLFTNGENGALVGAEYGTGVFYDETHTKSRYGLEYVYTN
                *** *.***.*..* .  **  **.  * * .********* ***.***.****.*

Tbp1-2394  ADKDTWADYARLSYDRQGIDLDNRLQQTHCSHDGSDKNCRPDGNKPYSFYKSDRMIYEES
Tbp1-2169  ADKDTWADYARLSYDRQGIGLDNHFQQTHCSADGSDKYCRPSADKPFSYYKSDRVIYGES
           *******************.***. ***** ***** ***.  **.* ***** ** **

Tbp1-2394  RNLFQAVFKKAFDTAKIRHNLSINLGYDRFKSQLSHSDYYLQNAVQAYDLITPKKPPFPN
Tbp1-2169  HRLLQAAFKKSFDTAKIRHNLSVNLGFDRFDSNLRHQDYYYQHANRAYSSKTPPKTANPN
            .**.**.****.*********.***.***.*.* *.*** *.*  **   .* *  **

Tbp1-2394  GSKDNPYRVSIGKTTVNTSPICRFGNNTYTDCTPRNIGGNGYYAAVQDNVRLGRWADVGA
Tbp1-2169  GDKSKPYWVSIGGGNVVTGQICLFGNNTYTDCTPRSINGKSYYAAVRDNVRLGRWADVGA
           * *  ** ****  . ** .**.************ * *. *****.*************
```

\*   identical amino acid
.    conserved amino acid

FIG 7A

```
Tbp1-2394   GIRYDYRSTHSEDKSVSTGTHRNLSWNAGVVLKPFTWMDLTYRASTGFRLPSFAEMYGWR
Tbp1-2169   GLRYDYRSTHSDDGSVSTGTHRTLSWNAGIVLKPADWLDLTYRTSTGFRLPSFAEMYGWR
            * ********.* ******* ***** ****  * ***** ******************

Tbp1-2394   AGESLKTLDLKPEKSFNREAGIVFKGDFGNLEASYFNNAYRDLIAFGYETRTQNGQTSAS
Tbp1-2169   SGVQSKAVKIDPEKSFNKEAGIVFKGDFGNLEASWFNNAYRDLIVRGYEAQIKNGKEEAK
            *    *   . .*****.**************** ********.  ***   * **  *

Tbp1-2394   GDPGYRNAQNARIAGINILGKIDWHGVWGGLPDGLYSTLAYNRIKVKDADIRADRTFVTS
Tbp1-2169   GDPAYLNAQSARITGINILGKIDWNGVWDKLPEGWYSTFAYNRVHVRDIKKRADRTDIQS
            ***.* *** *** ********** ***  **  ***.****.   **  ***** . *

Tbp1-2394   YLFDAVQPSRYVLGLGYDHPDGIWGINTMFTYSKAKSVDELLGSQALLNGNANAKKAASR
Tbp1-2169   HLFDAIQPSRYVVGLGYDQPEGKWGVNGMLTYSKAKEITELLGSRALLNGNSRNTKATAR
             ****.****** ***** *.*  ** * * ******  . *****.****** **  *

Tbp1-2394   RTRPWYVTDVSGYYNIKKHLTLRAGVYNLLNYRYVTWENVRQTAGGAVNQHKNVGVYNRY
Tbp1-2169   RTRPWYIVDVSGYYTIKKHFTLRAGVYNLLNYRYVTWENVRQTAGGAVNQHKNVGVYNRY
            ******. ****** **** ****************************************

Tbp1-2394   AAPGRNYTFSLEMKF
Tbp1-2169   AAPGRNYTFSLEMKF
            ***************

*    identical amino acid
    .    conserved amino acid
```

FIG 7B

```
Tbp2-2394  CLGGGGSFDLDSVETVQDMHSKPKYEDEKSQ-PESQQDVSENSGAAYGFAVKLPRRNAHF
Tbp2-2169  CLGGGGSFDLDSVDT-EAPRPAPKYQDVSSEKPQAQKD----QG-GYGFAMRLKRRN--W
           ************* *           *   * *    *       * .****  * ***

Tbp2-2394  NPKYKEKHKPLGSMDWKKLQ-RGEPNSFSERDE--LEKKR--G-----SSE-LIESKWED
Tbp2-2169  YPGAEESEVKLNESDWEATGLPTKPKELPKRQKSVIEKVETDGDSDIYSSPYLTPSNHQN
            *    *   *  **  *    *     *     ** *    *    ** *   *  *

Tbp2-2394  G-------Q--SRVVGYTNFTYVRSGYVYLNK-NNIDIKNNIVLFGPDGYLYYKGKEPSK
Tbp2-2169  GSAGNGVNQPKNQATGHENFQYVYSGWFYKHAASEKDFSNKKIKSGDDGYIFYHGEKPSR
           *       *     ** **  * ** ** **   *   * . * ***.* *   * **.

Tbp2-2394  ELP-SEKITYKGTWDYVTDAMEKQRF-EG--GSAAGGDKSGALSALEEGVLRNQAEAS--
Tbp2-2169  QLPASGKVIYKGVWHFVTDTKKGQDFREIIQPSKKQGDRYSGFSGDGSEEYSNKNESTLK
            ** * *.*** *  *** *  * *  *    *  * ** **. .*.      ** *

Tbp2-2394  SGHTDFGMTSEFEVDFSDKTIKGTLYRNNRITQNNSENKQIKTTRYTIQATLHGNRFKGK
Tbp2-2169  DDHEGYGFTSNLEVDFGNKKLTGKLIRNNASLNNNTNNDKHTTQYYSLDAQITGNRFNGT
             * *  * **  **** * *  * * *** * * ..**.*   *  *..  *  **** *

Tbp2-2394  ALAADKGATNGS-HPFISDSDSLEGGFYGPKGEELAGKFLSNDNKVAAVFGAKQKDKKDG
Tbp2-2169  ATATDKKENETKLHPFVSDSSSLSGGFFGPQGEELGFRFLSDDQKVAGVGSAKTKDKLEN
           * * **       *** ***.*** *** ***  ****.**  .*** *.*** *  *

Tbp2-2394  EN------------AAGPATE-----TVIDAYRITGEEFKKEQIDSFGDVKKLLVDGVE
Tbp2-2169  GAAASGSTGAAASGGAAGTSSENSKLTTVLDAVELTLNDKKIKNLDNFSNAAQLVVDGIM
                        *** .*     **.**.*   *  ** *  * **    *.***.

Tbp2-2394  LSLLPSEGNKAA---------------FQHEIE------QNGVKAT-------------
Tbp2-2169  IPLLPKDSESGNTQADKGKNGGTEFTRKFEHTPESDKKDAQAGTQTNGAQTASNTAGDTN
           . ***    .              *   *        *

Tbp2-2394  ---------VCCSNLDYMSFGKLSKEN-K-------------------DDMFLQGVRTP
Tbp2-2169  GKTKTYEVEVCCSNLNYLKYGMLTRKNSKSAMQAGGNSSQADAKTEQVEQSMFLQGERTD
                    ****** *   * * .** *                     ***** **

Tbp2-2394  VSDVAARTEANAKYRGTWYGYIANGTSWSGEASNQEGGNRAEFDVDFSTKKISGTLTAKD
Tbp2-2169  EKEIP--TDQNVVYRGSWYGHIANGTSWSGNASDKEGGNRAEFTVNFADKKITGKLTAEN
            . *  * *  *** *** ********* **  ********* * ** *** * ***

Tbp2-2394  RTSPAFTITAMIKDNGFSGVAKTGENGFALDPQNTGNSHYTHI-EATVSGGFYGKNAIEM
Tbp2-2169  RQAQTFTIEGMIQGNGFEGTAKTAESGFDLDQKNTTRTPKAYITDAKVKGGFYGPKAEEL
           *   ***  ** .*** * **** * **  *  ***        * * ******  *

Tbp2-2394  GGSFSFPGNAPEGKQE---------KASVVFGAKRQQLVQ
Tbp2-2169  GGWFAYPGDKQTEKATATSSDGNSASSATVVFGAKRQQPVQ
           ** *  **     *            *.********* **

*          identical amino acid
.          conserved amino acid
```

FIG 8

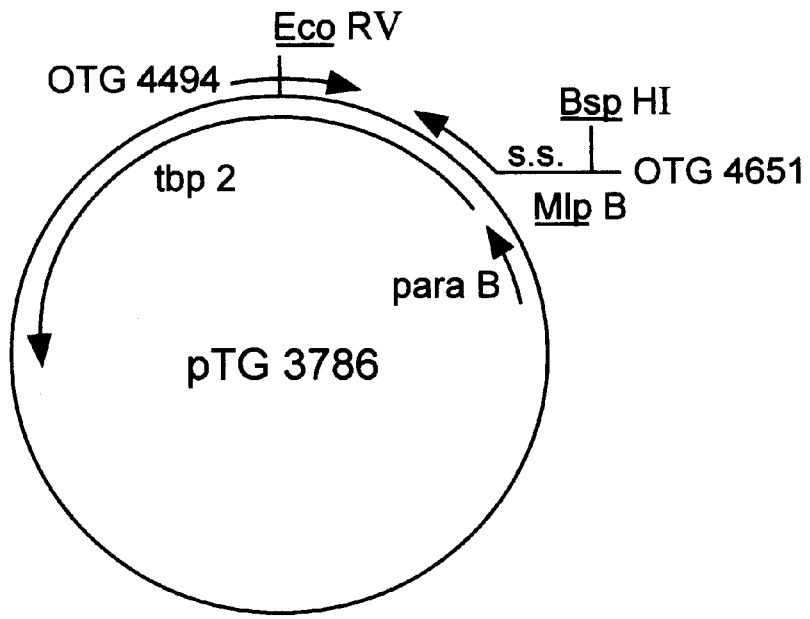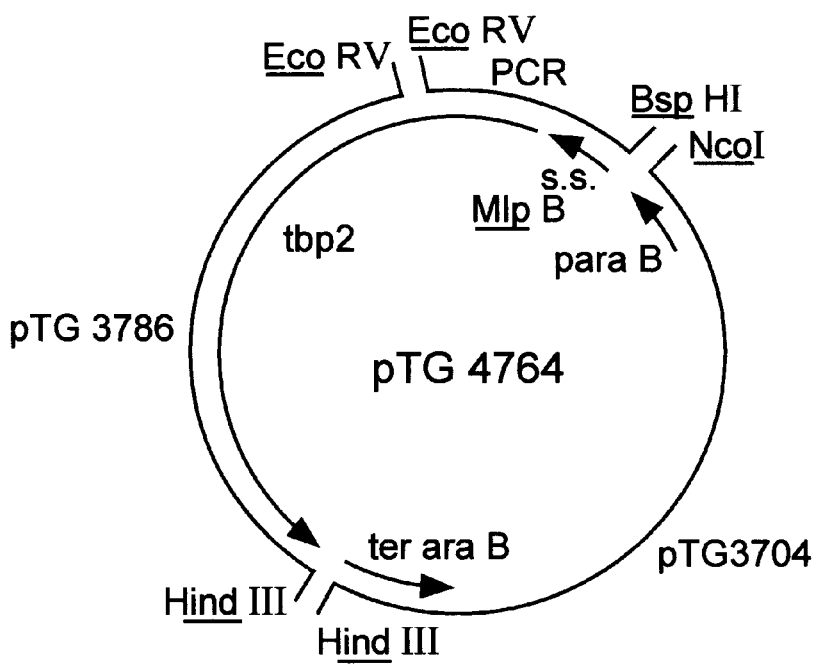
FIG. 11

COMPOSITIONS COMPRISING THE TBP2 SUBUNIT OF THE TRANSFERRIN RECEPTOR OF *NEISSERIA MENINGITIDIS*

This application is a continuation of application Ser. No. 08/361,469, filed Dec. 22, 1994, which is a continuation of application Ser. No. 08/078,053, filed Jun. 18, 1993, now abandoned.

BACKGROUND OF THE INVENTION

1. Field of the Invention

The subject of the present invention is DNA fragments of *Neisseria meningitidis* which encodes the transferrin receptor subunits as well as a process for producing each of the subunits by the recombinant route.

Meningitides are generally either of viral origin or of bacterial origin. The bacteria mainly responsible are: *N. meningitidis* and *Haemophilus influenzae*, which are respectively implicated in about 40 and 50% of cases of bacterial meningitides.

In France, about 600 to 800 cases of N. meningitidismeningitites are recorded per year. In the United States, the number of cases is up to about 2,500 to 3,000 per year.

The *N. meningitidis* species is sub-divided into serogroups according to the nature of the capsular polysaccharides. Although about twelve serogroups exist, 90% of meningitis cases can be attributed to 3 serogroups: A, B and C.

2. Description of the Related Art

Effective vaccines based on capsular polysaccharides exist for the prevention of meningitides caused by *N. meningitidis* serogroups A and C. These polysaccharides as they are only slightly or not at all immunogenic in children below 2 years and do not induce immunological memory. However, these disadvantages can be overcome by conjugating these polysaccharides with a carrier protein.

In contrast, the polysaccharide of *N. meningitidis* group B is not at all or is only slightly immunogenic in man whether it is in conjugated form or not. Thus it appears highly desirable to seek out a vaccine against meningitides induced by *N. meningitidis* especially of the serogroup B other than a polysaccharide-based vaccine.

To this end, various proteins of the outer membrane of *N. meningitidis* have already been proposed. These are in particular the membrane receptor for human transferrin.

In general, the great majority of bacteria require iron for their growth and they have developed specific systems for acquiring this metal. With regard especially to *N. meningitidis* which is a strict pathogen for man, the iron can only be derived from human iron transport proteins such as transferrin and lactoferrin since the quantity of iron in free form is negligible in man (of the order of $10^{-18}$ M), in any case insufficient to permit bacterial growth.

Thus, *N. meningitidis* has a human transferrin receptor and a human lactoferrin receptor which enable it to bind these iron-chelating proteins and subsequently to capture the iron required for its growth.

The transferrin receptor of the strain B16B6 of *N. meningitidis* has been purified by Schryvers et al. (WO 90/12591) from a membrane extract. This protein, as purified, appears to consist essentially of 2 types of polypeptides: a polypeptide with a high apparent molecular weight of 100 kD and a polypeptide with a lower apparent molecular weight of about 70 kD, as visualised after SDS-polyacrylamide gel electrophoresis.

The purification product especially identified by Schryvers is by arbitrary definition and for the purposes of the present patent application, called transferrin receptor and its constituent polypeptides, subunits. In the text which follows, the subunits of high molecular weight and of lower molecular weight are called Tbp1 and Tbp2 respectively.

However, the purification process described by Schryvers et al. cannot be used for the large-scale production of the transferrin receptor. The industrial preparation of this receptor in purified form necessarily involves a production step using a heterologous expression system.

SUMMARY OF THE INVENTION

To this end, the object of the invention is to provide DNA fragments which encode the transferrin receptor subunits of *N. meningitidis*.

Moreover, since the pioneering work of Schryvers et al., it has been discovered that there are in fact at least 2 types of strains which differ by the constitution of their respective transferrin receptors. This was demonstrated by studying membrane extracts of several tens of *N. meningitidis* strains of diverse origins. These membrane extracts were first subjected to an SDS-polyacrylamide gel electrophoresis and then electrotransferred onto nitrocellulose membranes. These nitrocellulose membranes were incubated:

a) in the presence of a rabbit antiserum directed against the transferrin receptor purified from the strain B16B6 of *N. meningitidis*, also called IM2394;

b) in the presence of a rabbit antiserum directed against the transferrin receptor purified from the strain IM2169 of *N. meningitidis*; or c) in the presence of peroxydase-conjugated human transferrin.

With regard to a) and b), the recognition of the transferrin receptor subunits is visualised by the addition of a peroxydase-coupled anti-rabbit immunoglobulin antibody and then by the addition of the substrate for this enzyme.

Tables I and II below show the profile of some representative strains as it appears on a 7.5% polyacrylamide gel after SDS gel electrophoresis; the bands are characterised by their apparent molecular weights expressed in kilodaltons (kD):

TABLE I

| | Strains | | |
|---|---|---|---|
| | 2394 (B; 2a; P1.2:12.3)<br>2228 (B; nd)<br>2170 (B; 2a:P1.2:1.3) | 2234 (Y; nd)<br>2154 (C; nd)<br>2448 (B; nd) | 550 (C; 2a:)<br>179 (C; 2a:P1.2) |
| Detection with anti-2394 receptor antiserum | 93<br>68 | 93<br>69 | 99<br>69 |
| Detection with anti-2169 receptor antiserum | 93<br>68 | 93<br>69 | 99<br>69 |

TABLE I-continued

| Strains | | | |
|---|---|---|---|
| 2394 (B; 2a; P1.2:12.3) | 2234 (Y; nd) | | |
| 2228 (B; nd) | 2154 (C; nd) | 550 (C; 2a:) | |
| 2170 (B; 2a:P1.2:1.3 | 2448 (B; nd) | 179 (C; 2a:P1.2) | |
| transferrin-peroxydase | | | |

N.B. in brackets are indicted in order the serogroup, the serotype, the subtype and the immunotype.

TABLE II

| | Strains | | | | | | | | |
|---|---|---|---|---|---|---|---|---|---|
| | 2169 (B:9:P1.9) | 1000 (B:nd) | 1604 (B:nd) | 132 (C:15:P1.16) | 1001 (A:4:P1.9) | 876 (B:19:P1.6) | 1951 (A:nd) | 2449 (B:nd) | 867 (B:2b:P1.2) |
| Detection with anti-2394 receptor antiserum | 96 | 98 | 98 | 98 | 98 | 96 | 94 | 94 | 93 |
| Detection with anti-2169 receptor antiserum | 96 | 98 | 98 | 98 | 98 | 96 | 94 | 94 | 93 |
| | 87 | 85 | 83 | 81 | 79 | 88 | 87 | 85 | 85 |
| Detection with transferrin-peroxydase | 87 | 85 | 83 | 81 | 79 | 88 | 87 | 85 | 85 |

N.B. In brackets are indicated in order the serogroup, the serotype, the subtype and the immunotype.

The results entered in the first 2 lines of the tables show that there are 2 types of strains:

The first type (Table I) corresponds to strains which possess a receptor whose 2 subunits, under the experimental conditions used, are recognised by the anti-IM2394 receptor antiserum whereas only the high molecular weight subunit is recognised by the anti-IM2169 receptor antiserum.

The second type (Table II) corresponds to strains which possess a receptor whose 2 subunits, under the experimental conditions used, are recognised by the anti-IM2169 receptor antiserum whereas only the high molecular weight subunit is recognised by the anti-IM2394 receptor antiserum.

Consequently, an antigenic diversity exists at the level of the subunit of lower molecular weight. This diversity is however limited since it is of 2 main types, contrary to what is suggested by Griffiths et al., FEMS Microbiol. Lett. (1990) 69:31.

By virtue of these observations, it could have been supposed that an effective vaccine against all N. meningitidis infections could be adequately made up of the high molecular weight subunit, irrespective of the strain from which the receptor originates, since the said subunit is recognised by the 2 types of antisera. However, it appears that this cannot be the case since the high molecular weight subunit is thought to be incapable of inducing the production of neutralising type antibodies. Only the smallest of the 2 receptor subunits is thought to be capable of performing this function. Since this subunit of lower molecular weight is characterised by a significant antigenic variation from the first type to the second type of strain, a single type of transferrin receptor could not be sufficient for vaccinating against all N. meningitidis infections. Consequently, a vaccine should contain at least the subunit of lower molecular weight of each of the strains IM2394 and IM2169 or their respective equivalents and, optionally, the high molecular weight subunit of at least one N. meningitidis strain.

BRIEF DESCRIPTION OF THE DRAWINGS

FIGS. 7a and 7b compare the predicted amino acid sequences of the Tbp1 subunits of the strains IM2394 (SEQ ID NO: 4) and IM2169 (SEQ ID NO: 6). The degree of homology may be estimated at about 76%.

FIG. 8 (SEQ ID NOS: 1–62) compares the predicted amino acid sequences of the Tbp subunits of the strains IM2394 (SEQ ID NO: 2) and IM2169 (SEQ ID NO: 3). The degree of homology may be estimated at about 47%.

FIG. 11 represents the methodology which was used to construct the expression vector pTG4764.

DETAILED DESCRIPTION OF THE PREFERRED EMBODIMENTS OF THE INVENTION

Figure 1:
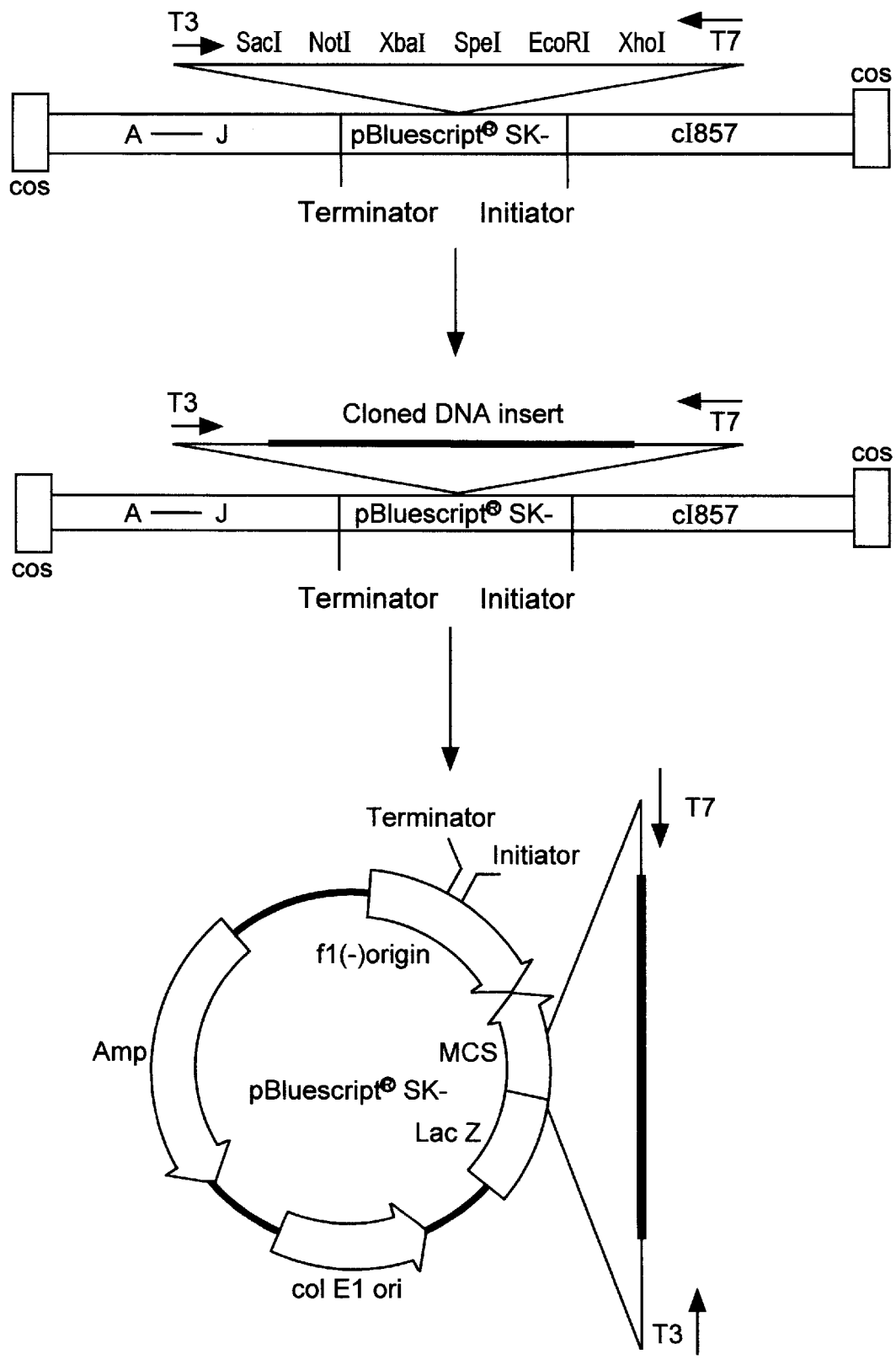
FIG. 1 represents the structure of the phage lambda ZAP II and schematically represents the cloning methodology relating thereto. Lambda ZAP II is an insertion vector equipped with multiple cloning sites located in the plasmid portion (pBluescript SK). This plasmid portion may be excised in vivo by coinfection with a helper phage and converted into plasmid vector. If a coding sequence is fused in phase with lacZ or if a cloned DNA fragment contains a promoter which is functional in E. coli, there may be production of a protein of interest which can be connected by means of specific antibodies.
Figure 2:
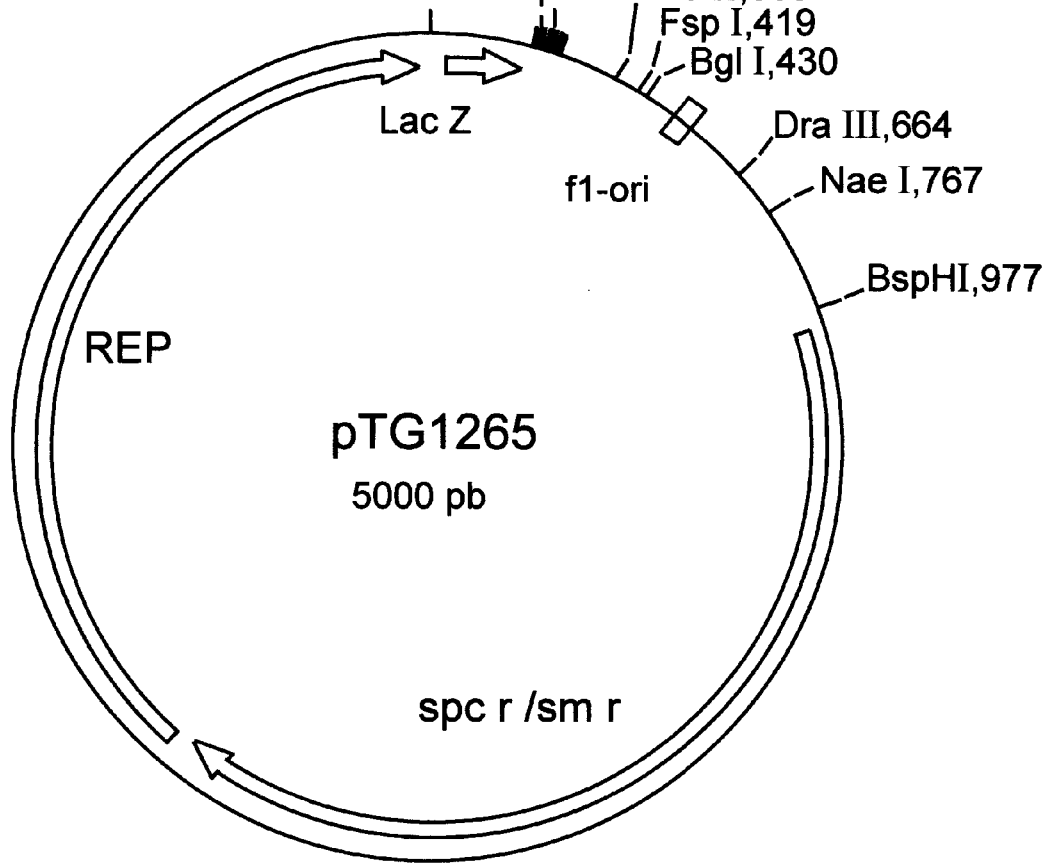
FIG. 2 represents the structure of the plasmid pTG1265. pTG1265 is derived from the plasmid pGB2 (Churchward et al., Gene (1984) 31:165) as follows: pGB2 is digested with EcoRI and HindIII, treated with Klenow polymerase and the ligated into the 1-kb SspI-PvuII fragment obtained from pT7T3 184 (Mead et al., Protein Engineering (1986) 1:67; Pharmacia) which contains f1-ori, the sequence lacZ, the promoters T3 and T7 as well as multiple cloning sites.

Accordingly, the invention provides an isolated DNA fragment which encodes a peptide, a polypeptide or a protein capable of being recognised by an antiserum against the receptor of the strain IM2394 or IM2169 of *N. meningitidis*.

Such a DNA fragment may especially comprise a nucleotide sequence which encodes an amino acid sequence, homologous to that shown:

in the sequence identifier (SEQ ID NO: 1) No. 1, starting with the cysteine residue in position 1 and ending with the glutamine residue in position 579;

in SEQ ID NO: 3, starting with the glutamic acid residue in position 1 and ending with the phenylalanine residue in position 884;

in SEQ ID NO: 5, starting with the glutamic acid residue in position 1 and ending with the phenylalanine residue in position 887; or in SEQ ID NO: 7, starting with the cysteine residue in position 1 and ending with the glutamine residue in position 691.

For guidance, it is specified that a DNA fragment according to the invention may furthermore comprise an additional nucleotide sequence which encodes any other amino acid sequence; the two nucleotide sequences considered forming an open reading frame so as to encode a hybrid protein or a precursor.

Advantageously, a DNA fragment according to the invention may be selected from:

i) A first isolated DNA fragment having a nucleotide sequence which encodes a protein having an amino acid sequence homologous to that shown in SEQ ID NO: 2, starting with the cysteine residue in position 1 and ending with the glutamine residue in position 579.

ii) A second isolated DNA fragment having a nucleotide sequence which encodes a protein having an amino acid sequence homologous to that shown in SEQ ID NO: 4, starting with the glutamic acid residue in position 1 and ending with the phenylalanine residue in position 884.

iii) A third isolated DNA fragment having a nucleotide sequence which encodes a protein having an amino acid sequence homologous to that shown in SEQ ID NO: 6, starting with the glutamic acid residue in position 1 and ending with the phenylalanine residue in position 887.

iv) A fourth isolated DNA fragment having a nucleotide sequence which encodes a protein having an amino acid sequence homologous to that shown in SEQ ID NO: 8, starting with the cysteine residue in position 1 and ending with the glutamine residue in position 691.

"Homologous amino acid sequence" is understood to mean a sequence which exhibits a degree of homology of at least 75%, advantageously of at least 80%, preferably of at least 90%, most preferably of 100%, with the amino acid sequence which is cited as reference. It should be noted that the term "homologous" as defined includes the special case of the identity.

The degree of homology can be easily calculated by aligning the sequences so as to obtain the maximum degree of homology; to do this, it may be necessary to artificially introduce empty spaces as illustrated in FIG. 7. Once the optimal alignment has been achieved, the degree of homology is established by recording all the positions in which the amino acids of the two sequences coincide, relative to the total number of positions.

It would be tedious to describe homologous sequences otherwise than in a generic manner because the number of combinations is too great. However, persons skilled in the art know the general rules which make it possible to replace one amino acid with another without destroying the biological or immunological function of a protein.

An isolated and most preferred DNA fragment has a nucleotide sequence which encodes:

i) The Tbp1 subunit of the strain IM2394 whose amino acid sequence is as shown in SEQ ID NO: 4, starting with the glutamic acid residue in position 1 and ending with the phenylalanine residue in position 884;

ii) the Tbp2 subunit of the strain IM2394 whose amino acid sequence is shown in SEQ ID NO: 2, starting with the cysteine residue in position 1 and ending with the glutamine residue in position 579;

iii) the Tbp1 subunit of the strain IM2169 whose amino acid sequence is shown in SEQ ID NO: 6, starting with the glutamic acid residue in position 1 and ending with the phenylalanine residue in position 887; or iv) the Tbp2 subunit of the strain IM2169 whose amino acid sequence is shown in SEQ ID NO: 8, starting with the cysteine residue in position 1 and ending with the glutamine residue in position 691.

The transferrin receptor being a membrane protein, each of its subunits is initially produced in the form of a precursor consisting of a signal peptide associated, in the N-terminal position, with the mature form.

Accordingly, the subject of the present invention is also an isolated DNA unit which encodes a signal peptide whose amino acid sequence exhibits a degree of homology of at least 80%, preferably of 100%, with the sequence shown in:

i) SEQ ID NO: 4, starting with the methionine residue in position −24 and ending with the alanine residue in position −1;

ii) SEQ ID NO: 6, starting with the methionine residue in position −24 and ending with the alanine residue in position −1; or iii) SEQ ID NO: 8, starting with the methionine residue in position −20 and ending with the alanine residue in position −1.

A DNA fragment according to the invention may also be selected from a fifth, sixth, seventh and eighth DNA fragment which respectively encode a precursor whose amino acid sequence is homologous to the sequence presented in SEQ ID NOS: 2, 4, 6, or 8.

"Isolated DNA fragment or unit" is understood to mean a DNA fragment or unit of genomic origin which is i) inserted into a viral or plasmid vector or ii) placed under the control of a promoter which, for its part, is heterologous.

Furthermore, the DNA unit which encodes the signal peptide according to the invention is, in addition, considered as isolated when this DNA unit is associated with a DNA fragment which encodes a protein heterologous to the signal peptide so as to form an open reading frame which encodes a hybrid precursor.

The invention also relates to a cassette for expressing a peptide, a polypeptide or a protein capable of being recognised by an antiserum against the receptor of the strain IM2394 or IM2169 of *N. meningitidis*, which comprises at least one DNA fragment according to the invention placed under the control of elements capable of bringing about its expression in an appropriate host cell.

In the expression cassette, the first, second, third or fourth DNA fragment according to the invention which encodes a mature form may be associated or not with a DNA unit which encodes a signal peptide depending on whether or not the secretion of the protein is sought. Preferably, this secretion will be sought. In this last case, the DNA unit may encode a signal peptide homologous or heterologous to the mature form, resulting in the synthesis of a natural or hybrid precursor respectively.

The elements essential for the expression of a DNA fragment according to the invention are a transcription promoter, translational start and stop codons and optionally, a transcription terminator. The promoter may be constitutive or inducible. It should be pointed out that the DNA fragment which encodes the Tbp2 subunit of the strain IM2394 appears to be toxic for a heterologous cell, especially for *E. coli*. In such a case, it may be preferable to use an inducible promoter, for example the araB gene promoter of *Salmonella thyphimurium*.

Elements such as a DNA unit which encode a heterologous signal peptide (signal region) or a promoter already exist in fairly large number and are known to a person skilled in the art. His general expertise will enable him to choose a signal region or a specific promoter which will be adapted to the host cell in which he envisages the expression.

More particularly, it should be noted that the Tbp2 subunit appears to be a lipoprotein since its precursor contains a signal peptide characteristic of lipoprotein precursors and because it possesses a cysteine in the $NH_2$-terminal position and amino acids with a strong tendency to adopt a "turn" type conformation slightly downstream of the $NH_2$-terminal cysteine (4 glycines). For reference, see Wu & Tokunaga, Current Top. Microb. Immunol. (1986) 125: 127. The lipidation might enhance the immunogenicity of the Tbp2 subunit.

Thus, in a prokaryotic system, it would be desirable to obtain the Tbp2 subunit either from its natural precursor or from a precursor which comprises a suitable heterologous signal peptide which permits the lipidation; that is to say a signal peptide of a lipoprotein other than Tbp2. Such a signal peptide has especially the characteristic of being liberated by cleavage of the precursor with a type II signal peptidase. The sequence at the cleavage site of the signal peptide corresponds to the consensus sequence (L, V, I) (A, S, T, G) (G, A) C, cysteine (C) being the first amino acid of the mature sequence. By way of example of heterologous signal peptide, there may be mentioned especially those of the lipoproteins ColE1, ColE3, Lpp, NlpA, OsmB, Pal, RlpB and TraT whose sequences are presented in SEQ ID NO: 9 to 24 respectively, as well as the corresponding nucleotide sequences.

Consequently, according to a specific embodiment, an expression cassette according to the invention, intended for the production of a protein having an amino acid sequence homologous to that shown:

in SEQ ID NO: 2, starting with the cysteine residue in position 1 and ending with the glutamine residue in position 579 or in SEQ ID NO: 8, starting with the cysteine residue in position 1 and ending with the glutamine residue in position 691;

comprises:

i) a DNA unit which encodes a signal peptide of a lipoprotein other than the Tbp2 subunit, such as the signal peptide RlpB and ii) a DNA fragment which encodes the said protein.

Finally, the invention provides (i) a process for producing a peptide, a polypeptide or a protein capable of being recognised by an antiserum against the receptor of the strain IM2394 or IM2169 of *N. meningitidis*, according to which a host cell containing an expression cassette according to the invention is cultured and the said peptide, polypeptide or protein is recovered from the culture; as well as (ii) the peptide, polypeptide or protein produced by this process and (iii) pharmaceutical, especially vaccinal, compositions containing them.

For the purposes of the process according to the invention, the host cell may be a mammalian cell, a yeast or a bacterium, the latter being preferred. In this case also, the choice of a specific line is within the scope of a person skilled in the art.

Alternatively, a pharmaceutical composition according to the invention may contain, as active ingredient, a viral or bacterial vector in whose genome is inserted a DNA fragment according to the invention, placed under the control of the elements required for its expression. By way of example of appropriate vector, there may be mentioned especially pox viruses, adeno-virus and lactic acid bacteria.

A pharmaceutical composition according to the invention is especially useful for the treatment or prevention of an *N. meningitidis* infection. It may be manufactured in a conventional manner. In particular, a therapeutically effective amount is combined with a carrier or a diluent. It may be administered by any conventional route in usage in the field of the art, e.g. in the field of vaccines, especially enterally or parenterally. The administration may be made in a single dose or repeated after a certain period of time. The route of administration may vary as a function of various parameters, for example the individual treated (condition, age and the like). A composition may, in addition, contain a pharmaceutically acceptable adjuvant.

In order to determine the object of the present invention, it should be specified that the strains IM2394 (also called B16B6) and IM2169 (also called M982) of *N. meningitidis* are openly available from the Collection de Institut Pasteur, 25 rue de Dr Roux 75015 Paris, under the registration numbers CIP7908 and CIP7917 respectively.

An antiserum specific for the transferrin receptor of the strain IM2394 or IM2169 of *N. meningitidis* may be obtained as described in the examples below.

EXAMPLE 1

Cloning of the DNA fragments which encode the Tbp1 and Tbp2 subunits of the transferrin receptor of the strain IM2394

1A—Culture of the strain and purification of the transferrin receptor

A freeze-dried product of the strain IM2394 of *N. meningitidis* is taken up in about 1 ml of Muller-Hinton broth (MHB, Difco). The bacterial suspension is then plated on the solid Muller-Hinton medium containing boiled blood (5%).

After incubating for 24 h at 37° C. in an atmosphere containing 10% $CO_2$, the bacterial layer is recovered in order to inoculate 150 ml of MHB, pH 7.2, distributed into 3 250-ml Erlenmeyer flasks. The incubation is continued for 3 h at 37° C., with stirring. Each of the 3 cultures thus produced makes it possible to inoculate 400 ml of MHB, pH 7.2, supplemented with 30 $\mu$m ethylenediamine-di(o-hydroxyphenylacetic acid), (EDDHA, Sigma) which is an iron-chelating agent in free form.

After culturing for 16 h at 37° C. with stirring, the cultures are checked for their purity by examination under a microscope after Gram staining. The suspension is centrifuged, the pellet containing the pathogenic microorganisms is weighed and preserved at −20° C.

The purification is carried out essentially according to the method described by Schryvers et al. (supra), as follows:

The bacterial pellet is thawed and then resuspended in 200 ml of 50 mM Tris-HCl buffer, pH 8.0 (buffer A). The suspension is centrifuged for 20 min at 15,000×g at 4° C. The pellet is recovered, then resuspended in buffer A to a final concentration of 150 g/l. 150-ml fractions are treated for 8 min at 800 bars in a cell breaking device operating under high pressure (Rannie, model 8.30 H). The cell lysate thus obtained is centrifuged for 15 min at 4° C. at 15,000×g. The supernatant is recovered and then centrifuged for 75 min at 4° C. at 200,000×g. After removal of the supernatant, the pellet is taken up in buffer A and after protein assay according to Lowry, the concentration of the suspension is adjusted to 5 mg/ml.

To 1.4 ml of the membrane suspension are added 1.75 mg of human tranferrin biotinylated according to the process described by Schryvers. The final concentration of the membrane fraction is 4 mg/ml. The mixture is incubated for 1 hour at 37° C. and then centrifuged at 100,000×g for 75 minutes at 4° C. The membrane pellet is taken up in buffer A containing 0.1 M NaCl and incubated for 60 minutes at room temperature.

After solubilisation, a certain volume of 30% N-lauroylsarcosine (w/v) and 500 mM EDTA is added to this suspension so that the final sarkosyl and EDTA concentrations are 0.5% and 5 mM respectively. After incubating for 15 minutes at 37° C., with stirring, 1 ml of strepavidin-agarose (Pierce), previously washed in buffer A, is added. The suspension is incubated for 15 minutes at room temperature and then centrifuged at 1,000×g for 10 minutes. The resin is then packed into a column and the direct eluate is discarded.

The resin is washed with 3 column volumes of 50 mM Tris-HCl buffer, pH 8.0, containing 1 M NaCl, 10 mM EDTA, 0.5% sarkosyl (buffer B) and then with a column volume of buffer B containing 750 mM guanidine-HCl. The transferrin receptor is then eluted with buffer B containing 2 M guanidine-HCl. The eluate is collected as fractions, in tubes containing an identical volume of 50 mM Tris-HCl, pH 8.0, 1 M NaCl. The optical density at 280 nm of the eluate is measured at the column outlet by means of a UV detector.

The fractions corresponding to the elution peak are recovered, dialysed against 10 mM phosphate buffer, pH 8.0, containing 0.05% sarkosyl and freeze-dried. The freeze-dried product is taken up in water to a concentration 10 times higher. The solution is dialysed a second time against 50 mM phosphate buffer, pH 8.0, containing 0.05% sarkosyl (buffer C) and then the solution is filtered on a membrane of porosity 0.22 μm.

The protein content is determined and adjusted to 1 mg/ml by addition of buffer C, under aseptic conditions. This preparation is preserved at −70° C.

1B—Preparation of an antiserum specific for the transferrin receptor

New Zealand albino rabbits receive subcutaneously and intramuscularly 100 μg of the IM2394 receptor in the presence of complete Freund's adjuvant. 21 days and 42 days after the first injection, the rabbits again receive 100 μg of the purified receptor but this time in the presence of incomplete Freund's adjuvant. 15 days after the last injection, serum is collected from the animals and then decomplementised and filtered on a membrane of porosity 0.45 μm. The filtrate is subsequently exhausted by contact with the strain IM2394 which, in order to do this, was cultured beforehand in the presence of iron in free form (under these conditions, the synthesis of the transferrin receptor is repressed). The conditions of contact are as follows: 10 ml of filtrate are added to $10^{10}$ cfu (colony-forming units) of a culture of the strain IM2394. The adsorption is continued overnight at 4° C., with stirring. The bacteria are then removed by centrifugation. The supernatent is recovered and then again subjected to 2 successive adsorption operations as described above.

1C—Determination of the peptide sequences which permit identification of the DNA fragments.

Aliquot fractions of the material obtained in 1A are dried and then resolubilised in two times concentrated Laemmli buffer (65 mM Tris, 3% SDS, 10% glycerol, 5% 2-mercaptoethanol). An equivalent volume of water is added.

After sonication, the material is heated at 90° C. for 2 minutes and then subjected to a polyacrylamide gel electrophoresis. The subunits thus separated are transferred onto PVDF membrane (Immobilon, Millipore) for 16 hours at 400 mA in 50 mM Tris-borate buffer, pH 8.3. The electrotransferred subunits are stained with amido black and the bands corresponding to Tbp1 and Tbp2 are recovered and subjected to microsequencing of the N-terminal end.

This is repeated several times in order to establish the following N-terminal consensus sequences [SEQ ID NOS. 25–26]:

Tbp1 IM2394 :EXVQAEQAQEKQLDTIQV
Tbp2 IM2394 :XLXXXXSFDLDSVEXVQXMX
(X=undetermined amino acid).

In order to sequence the internal regions of Tbp2, the protein on PVDF membrane is subjected to trypsin digestion in 0.1 M Tris buffer, pH 8.2. After reacting for 4 hours at 37° C., the peptides are extracted with 70% formic acid and then with 0.1% trifluoroacetic acid (TFA). These peptides are then separated by HPLC.

For Tbp2 IM2394, the internal sequences [SEQ ID NOS: 27–36] which were established are the following:
S1122: NNIVLFGPDGYLYYK
S1125: YTIQA
S"770: DGENAAGPATEXVIDAYR
S"766: XQIDSFGDVK
S1126: AAFXXXI
S"769: XNXXXMFLQGVR
S"771: TPVSDVAAR
S"767: XSPAFT
S"762: NAIEMGGSFXFPGNAPEG(K)
S1128: XQPESQQDVSENX 1D—Preparation of the genomic DNA The bacterial pellet obtained in 1A is resuspended in about 25 ml of solution A (25 mM Tris-HCl, pH 8, containing 50 mM glucose and 10 mM EDTA) supplemented with 10 mg of proteinase K. The mixture is left for 10 minutes at room temperature.

Then 12.5 ml of solution A containing 10 mg of lysozyme are added. The mixture is yet again left for 10 minutes at room temperature. The mixture is then topped up with 0.5 ml of 10% sarkosyl. The mixture is incubated for 10 minutes at +4° C.

2 mg of RNase are then added and the incubation is continued for 90 minutes at 37° C. The DNA is purified by four successive phenol extractions. The DNA present in the final aqueous phase is precipitated with ethanol. High molecular weight DNA is obtained by CsCl gradient separation.

1E—Cloning

A first DNA library was prepared in the lambda ZAP vector (FIG. 1), as follows:

A genomic DNA preparation was fragmented by ultrasonic treatment. The ends of the fragments thus obtained were made blunt by treatment with $T_4$ polymerase. The fragments were methylated. After methylation, the fragments were linked to EcoRI adaptors, treated with EcoRI and then inserted into the EcoRI site of phage lambda ZAP II (Stratagene).

The strain XL1-blue of *E. coli* (Stratagene) was infected with the DNA library thus prepared. The white lysis plaques (presence of recombinant phages) were tested using an antiserum specific for the transferrin receptor of the strain IM2394 prepared as described in 1B. This made it possible to identify two lambda ZAP II clones. The pBluescript plasmids contained in these clones were excised by coinfection with helper phage and were called pBMT1 and pBMT2.

The plasmids pBMT1 and pBMT2 each contain an EcoRI-EcoRI fragment of 3.8 kb and 1.3 kb respectively. They are presented in FIG. 3.

Sequencing of the EcoRI-EcoRI insert of pBMT1 was carried out according to the shotgun method (Bankier and Barrell, Biochemistry (1983) B5: 508), as follows:

The EcoRI-EcoRI insert of pBMT1 was purified and then fragmented by ultrasonic treatment. The ends of the fragments thus obtained were made blunt by treatment with $T_4$ polymerase. The fragments thus treated were introduced into a site of the phage M13TG131 (described in Kieny et al., Gene (1983) 26: 91). About 200 clones obtained from this preparation were sequenced. Computer analysis of these sequences made it possible to reconstitute the complete sequence of the EcoRI-EcoRI insert of pBMT1.

Figure 3:
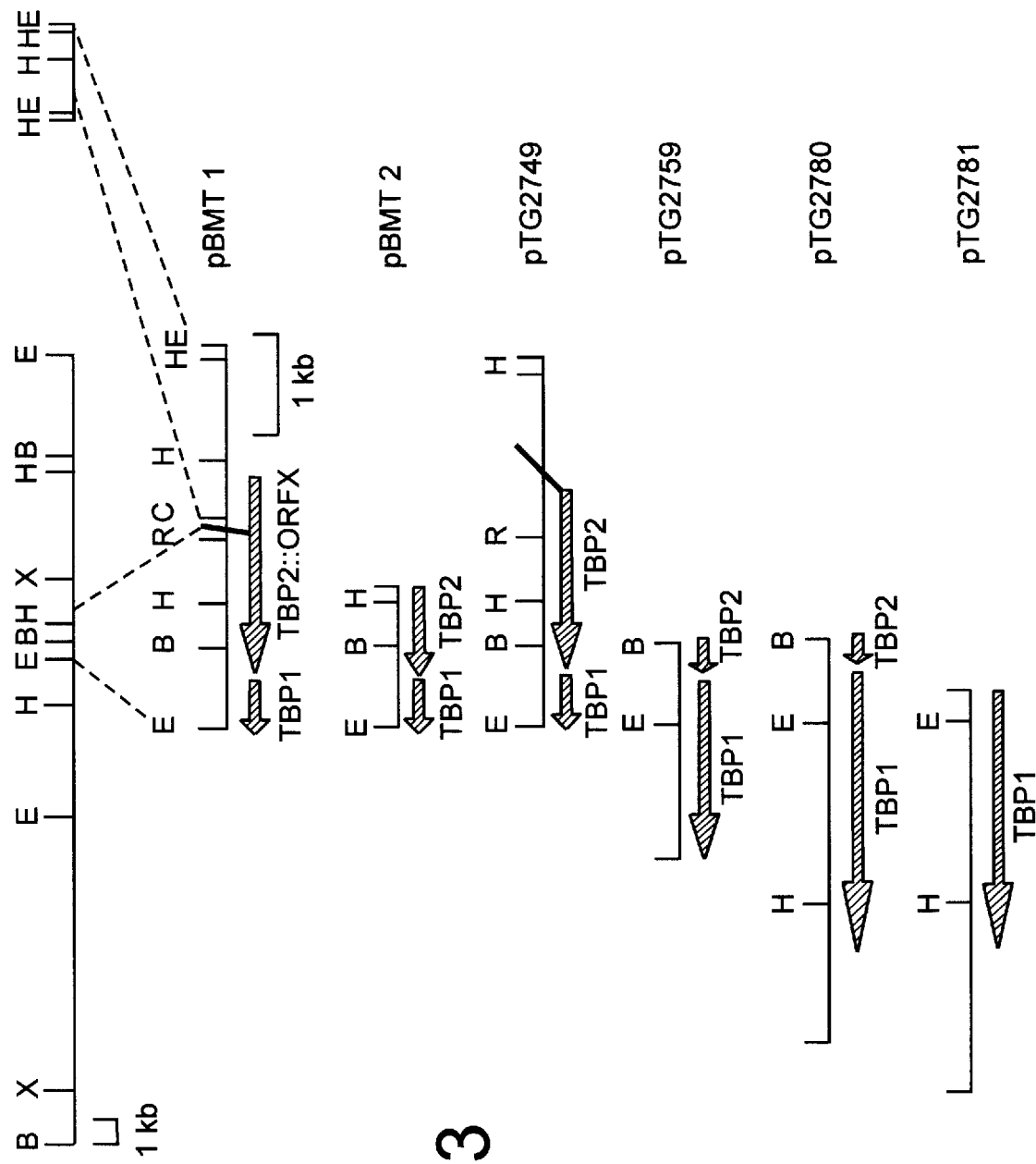
FIG. 3 represents the genomic map of the DNA region of the strain IM2394 containing the sequences which encode Tbp1 and Tbp2 as well as the different fragments which were cloned. B=BamHI; E=EcoRI; H=HincII; R=EcoRV; X=XbaI; C=ClaI.

The sequence encoding the N-terminal end of Tbp1 was localised as shown in FIG. 3. Given the molecular mass of Tbp1 it was clear that this insert did not contain the complete DNA fragment which encodes Tbp1. An open reading frame was identified upstream of the 5' end of the tbp1 gene but it was not possible to clearly identify the region which encodes the N-terminal end of the tbp2 gene.

Microsequencing of the internal regions of Tbp2 was therefore affirmed as reported above in 1C. The internal sequences which were localised towards the C-terminal end indeed corresponded to the 3' portion of the open reading frame upstream of tbp1.

Furthermore, the genomic DNA of the strain IM2394, previously digested with HincII, was analysed by Southern blotting using a radioactive DNA probe corresponding to the 1.5-kb HincII-HincII region of the 3.8-kb insert of pBMT1; two bands were thus visualised. This made it possible to demonstrate that the insert carried by pBMT1 resulted from an artefactual assembly of sequences obtained from two distinct loci. The 5' sequence of tbp2 was therefore absent.

The above-described genomic DNA library in lambda ZAP was again screened, this time using the EcoRI-EcoRI insert of pBMT2 as probe. 29 candidates were retained among about 200,000 plaques tested. Only the derived plasmid pTG2749 appeared to possess a new insert relative to pBMT1 and pBMT2. The insert of pTG2749 is as represented in FIG. 3. The region of the insert upstream of the EcoRV site (EcoRV-EcoRI region) was subcloned into M13TG131 and sequenced by the method of Sanger et al., PNAS (1977) 74: 5463 using synthetic primers. The sequence corresponding to the N-terminal end of Tbp2 was thus obtained.

The sequence of the DNA fagment which encodes Tbp2 of the strain IM2394 is presented in SEQ ID NO: 1 as well as the corresponding amino acid sequence.

Just upstream of the sequence which encodes mature Tbp2, the insert of pTG2749 contains a distinct genomic region obtained from another locus. In this case also, it is a cloning artefact analogous to that detected in the case of pBMT1.

Given the rearrangements observed and the absence of 3' sequences of tbp1 and 5' sequences of tbp2, the genomic DNA library constructed in lambda ZAP was judged unsuitable for continuing the cloning.

A second genomic DNA library was therefore constructed in a low-copy number plasmid as follows: a genomic DNA preparation was partially digested with Sau3A. DNA fragments of about 4 to 6 kb were purified after sucrose gradient fractionation and inserted into the BamHI site of the plasmid pTG1265. This plasmid preparation was used to transform the strain 5K of *E. coli*. It was estimated that this library contained about 18,000 independent clones.

About 50,000 clones from the second library were tested using a radioactive probe corresponding to the EcoRI-EcoRI insert of pBMT2. Only one clone was observed, that is to say the plasmid pTG2759 which has a 1.8-kb insert. The size of this insert was judged to be insufficient to contain the complete gene which encodes Tbp1.

A third DNA library was constructed according to the method described in the preceding paragraph except for the strain 5K of *E. coli* which was replaced by the strain SURE of *E. coli* (Stratagene). It was estimated that this library contained about 60,000 independent clones.

About 70,000 clones from the third DNA library were tested using a radioactive probe corresponding to the 2.4-kb MluI-HincII fragment obtained from the insert of pTG2754 described in Example 2 below and represented in FIG. 4. Two clones were detected, that is to say the plasmids pTG2780 and pTG2781, represented in FIG. 3.

The sequence of the inserts of pTG2780 and pTG2781 was established according to the Sanger method. It is presented in SEQ ID NO: 3 as well as the corresponding amino acid sequence.

A fourth library was constructed. The genomic DNA was digested with Sau3A and a fraction containing fragments of about 7 kb was purified on a sucrose gradient. This fraction contained a fragment corresponding to the locus tbp1,2 since it was recognised by a DNA probe specific for tbp2. After digestion with EcoRV and XbaI and ligation into pTG1265 digested with SmaI and XbaI, *E. coli* 5K was transformed. The clones were screened using a probe specific for tbp2. Among a series of positive clones, the plasmid pTG3791 was studied in particular and was found to contain tbp2 5' sequences including the sequence which encodes the putative signal peptide of Tbp2.

EXAMPLE 2

Cloning of the DNA fragments which encode the Tbp1 and Tbp2 subunits of the transferrin receptor of the strain IM2169

2A—The culture of the strain IM2169 and the purification of the transferrin receptor were performed under conditions identical to those described in Example 1A.

2B—The preparation of an antiserum against the receptor of the strain IM2169 was carried out according to the procedure described in Example 1B.

2C—The peptide sequences permitting the identification of the DNA fragments were determined according to the method reported in Example 1C. The microsequences which were established are the following.

Consensus sequence [SEQ ID NO. 37] of the N-terminal end of Tbp1:
ENVQAGQAQEKQLXXIQVX Sequences [SEQ ID NOS. 38–41] of the internal peptides of Tbp1:
S1031: XLS(E,W)NAGXVLXPADX
S1032: QLDTIQVK
S1033: TAGSSGAINEIEYENXX
S1034: YVTWENVDXXXXXX Consensus sequence [SEQ ID NO. 42] of the N-terminal end of Tbp2:
SLVXAXSFDLXSV Sequences [SEQ ID NOS. 43–46] of the internal peptides of Tbp2:
S1037: XXDNLSNAX
S1035: XGDDGYIFYXGEKPX
S1036: XQGXYGFAMX
S1040: XQATGHENFQYVYSGXFYK 2D—Preparation of the genomic DNA of the strain IM2169 was carried out according to the procedure described in Example 1D.

2E—Cloning

A first genomic DNA library (fragments of partial Sau3A DNA; pTG1265; *E. coli* 5K) was constructed as described above in Example 1. It was estimated that this library contained about 40,000 independent clones, of which about 70% had a 4–6-kb insert.

Figure 4:
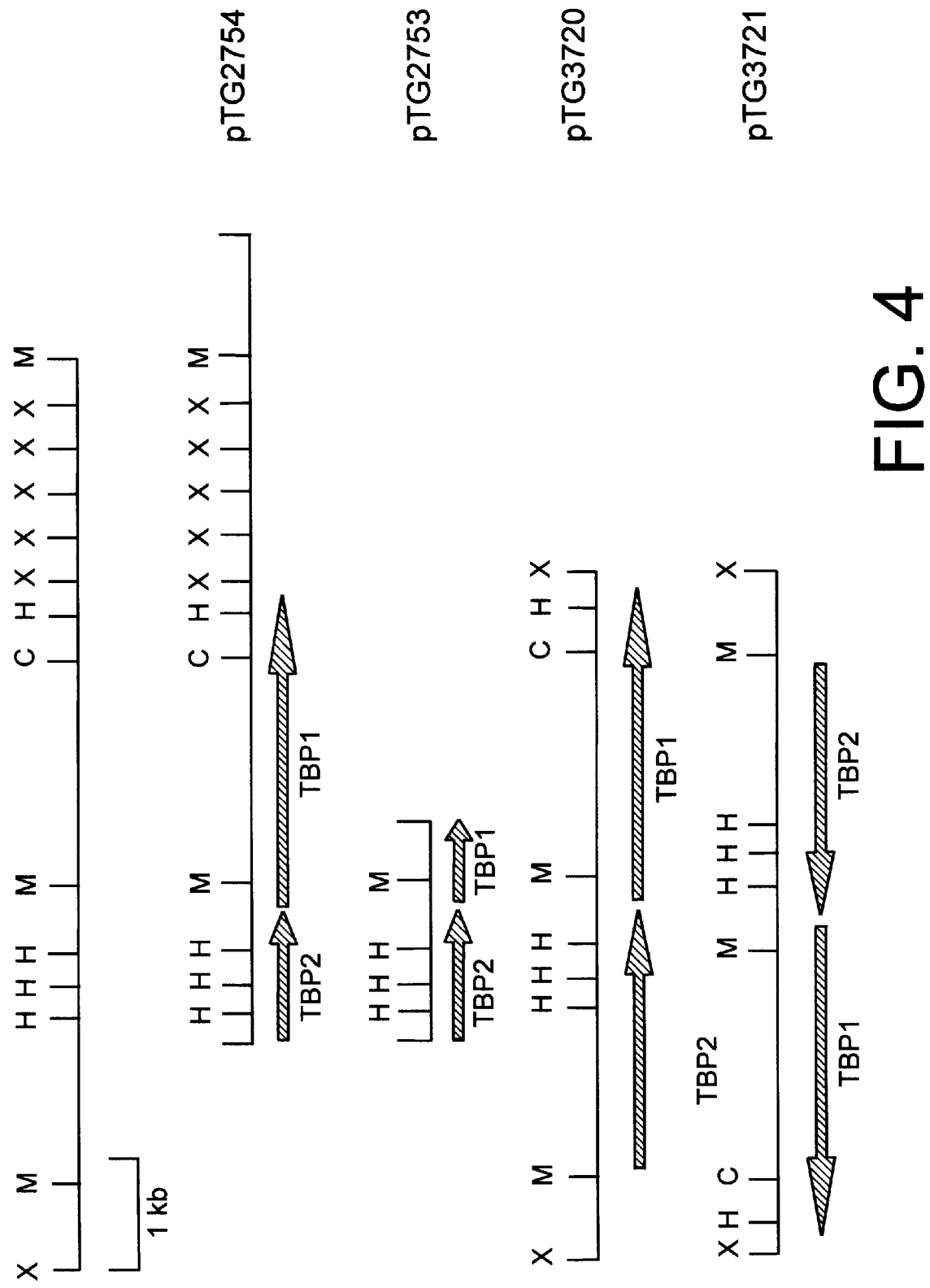
FIG. 4 represents the genomic map of the DNA region of the strain IM2169 containing the sequences which encode TBP1 and TBP2 as well as the different fragments which were cloned. C=ClaI; H=HincII; M=MluI; X=XbaI; ?=imprecise position.

130,000 clones from this library were tested using a radioactive probe corresponding to the EcoRI-EcoRI insert of pBMT2. 42 clones were analysed, among which 2 were retained: the plasmids pTG2753 and pTG2754 which are as shown in FIG. 4. Southern blot analyses showed that the restriction maps of the inserts of pTG2753 and pTG2754 corresponded to the restriction map of the genomic DNA.

The determination of the nucleotide sequences and the search for the regions which encode the N-terminal ends and the internal regions demonstrated that:

the 1.9-kb insert of pTG2753 contains the 3' portion of the tbp2 gene and the 5' portion of the tbp1 gene; and the insert of pTG2754 contains the 3' portion of the tbp2 gene and the 5' and 3' portions of the tbp1 gene, with phase disruption.

This first library did not therefore make it possible to clone the complete DNA fragments which encode Tbp1 or Tbp2.

A second genomic library was constructed as above but from XbaI-digested genomic DNA. The DNA fragments were purified after sucrose gradient fractionation. Each fraction (about 500 µl) was tested by Southern blotting with a radioactive probe corresponding to the 3' end of tbp1 (fragment of the insert of pTG2754). The fraction exhibiting a hybridisation reaction and containing about 6-kb fragments was cloned into pTG1265. The strain 5K of *E. coli* was transformed.

About 2,400 clones from this library were tested using a radioactive probe corresponding to the 0.6-kb HincII-MluI fragment obtained from pTG2754. Five clones were characterised, among which 2 were retained: that is to say pTG3720 and pTG3721, as shown in FIG. 4, both of which contain the tbp1 and tbp2 genes.

In order to complete the nucleotide sequence which encodes Tbp1, the insert of pTG3720 was sequenced in the region where the phase disruption discovered in the insert of pTG2754 was situated. This sequencing made it possible to show that the phase disruption of the insert of pTG2754 was due to a 22 bp deletion. The complete sequence of the DNA fragment is as shown in SEQ ID NO: 5.

The sequencing of the insert of pTG3720 was pursued in order to establish the sequence of tbp2. The said sequence was indeed identified, but again in this case a phase disruption was observed.

Finally, the sequence of tbp2 was determined from the plasmid pTG3721. It is as shown in SEQ ID NO: 7.

EXAMPLE 3

Expression of the DNA fragment which encodes the Tbp2 subunit of the strain IM2394

3A. Construction of the expression vector pTG3749.

Figure 5:
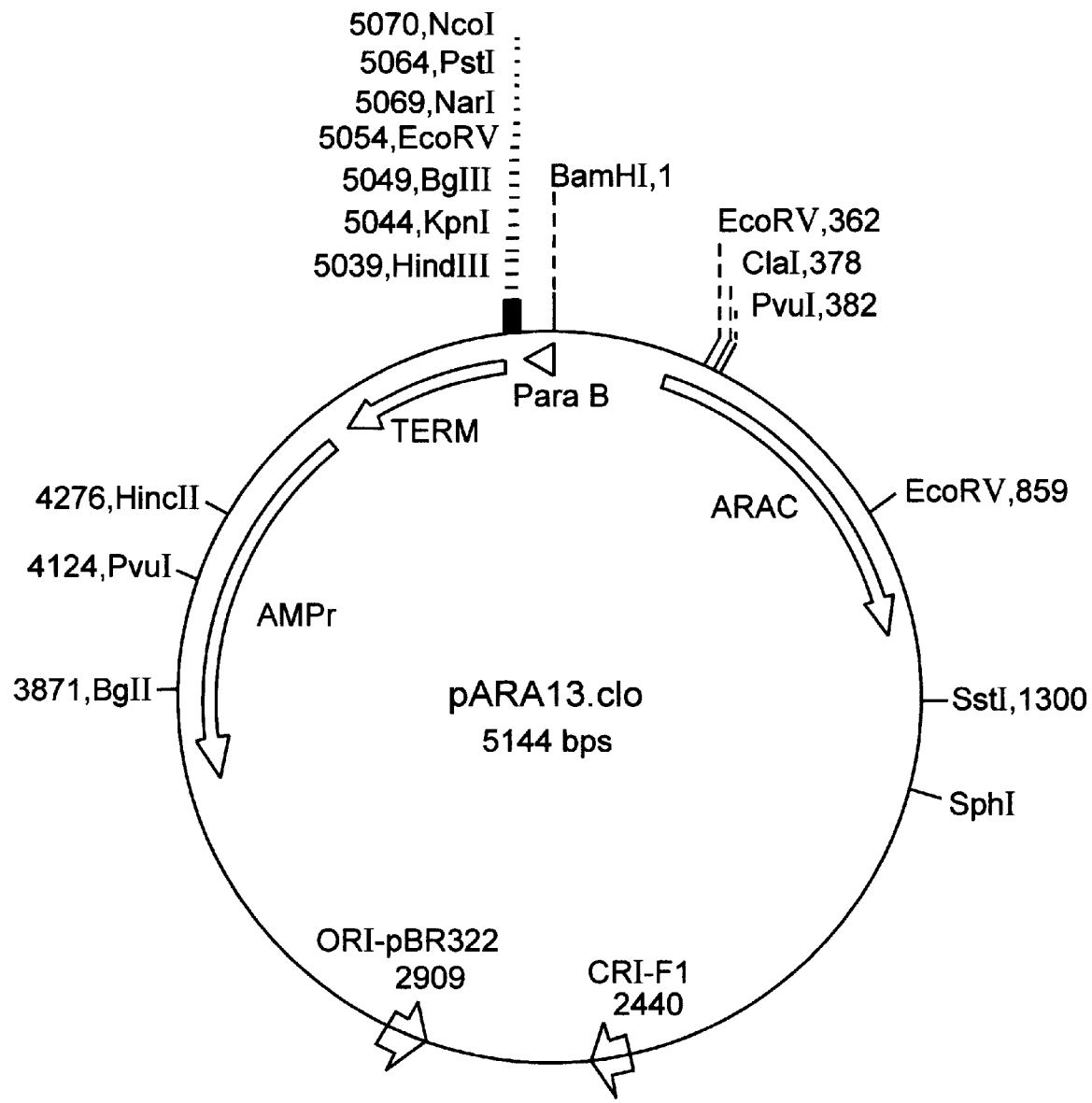
FIG. 5 represents the structure of the plasmid pARA13. pARA13 is a plasmid capable of replicating in E. coli which contains the promoter of the arabinose operon BAD (ParaB) of Salmonella typhimurium (modified at the level of the TATA box), as well as the AraC gene. Downstream of the promoter ParaB are multiple insertion sites. The pARA plasmid series is described by Cagnon et al., Prot. Eng. (1991) 4: 843.

The SphI site of the plasmid pARA13 (FIG. 5; Cagnon et al., Prot. Eng. (1991) 4: 843) was destroyed by treatment with klenow polymerase in order to give the plasmid pTG3704. pTG3704 was linearised by NcoI cleavage, treated with Klenow polymerase in order to produce blunt ends and then digested with HindIII.

Furthermore, the oligonucleotides OTG4015 and OTG4016 [SEQ ID NOS: 47–48] were synthesised and paired.

OTG4015:5' AAATACCTATTGCCTACGGCAGC-CGCTGGACTGTTATTACT CGCTGCCCAACCAGC-GATGGCATGCTTTCCCACGCGTTTTCCCA 3'

OTG4016:5' AGCTTGGGAAAACGCGTGGGAAAG-CATGCCATCGCTGGTTGGGCA GCGAGTAATAA-CAGTCCAGCGGCTGCCGTAGGCAATAGGTATTT 3'

The double-stranded DNA fragment OTG4015/OTG4016 was inserted into pARA13 treated as described above, in order to give the plasmid pTG3717 in which the sequence [SEQ ID NO: 49] which encodes the N-terminal portion of the precursor of the protein PelB of *Erwinia carotovora* had been reconstituted (Lei et al., J. Bact. (1987) 169: 4379); that is to say: 1

```
....... ATG AAA TAC CTA CCT ACG GCA GCC GCT
        Met Lys Tyr Leu Leu Pro Thr Ala Ala Ala

GGA CTG
        Ala Gly Leu

SphI
    TTA TTA CTC GCT GCC CAA CCA GCG ATG GCA TGCTTT
    Leu Leu Leu Ala Ala Gln Pro Ala Met Ala

MluI        HindIII
    CCCACGCGTTTTCCCA AGCTT.....

0
```

(The ends of pTG3704 are underlined)

Figure 6:
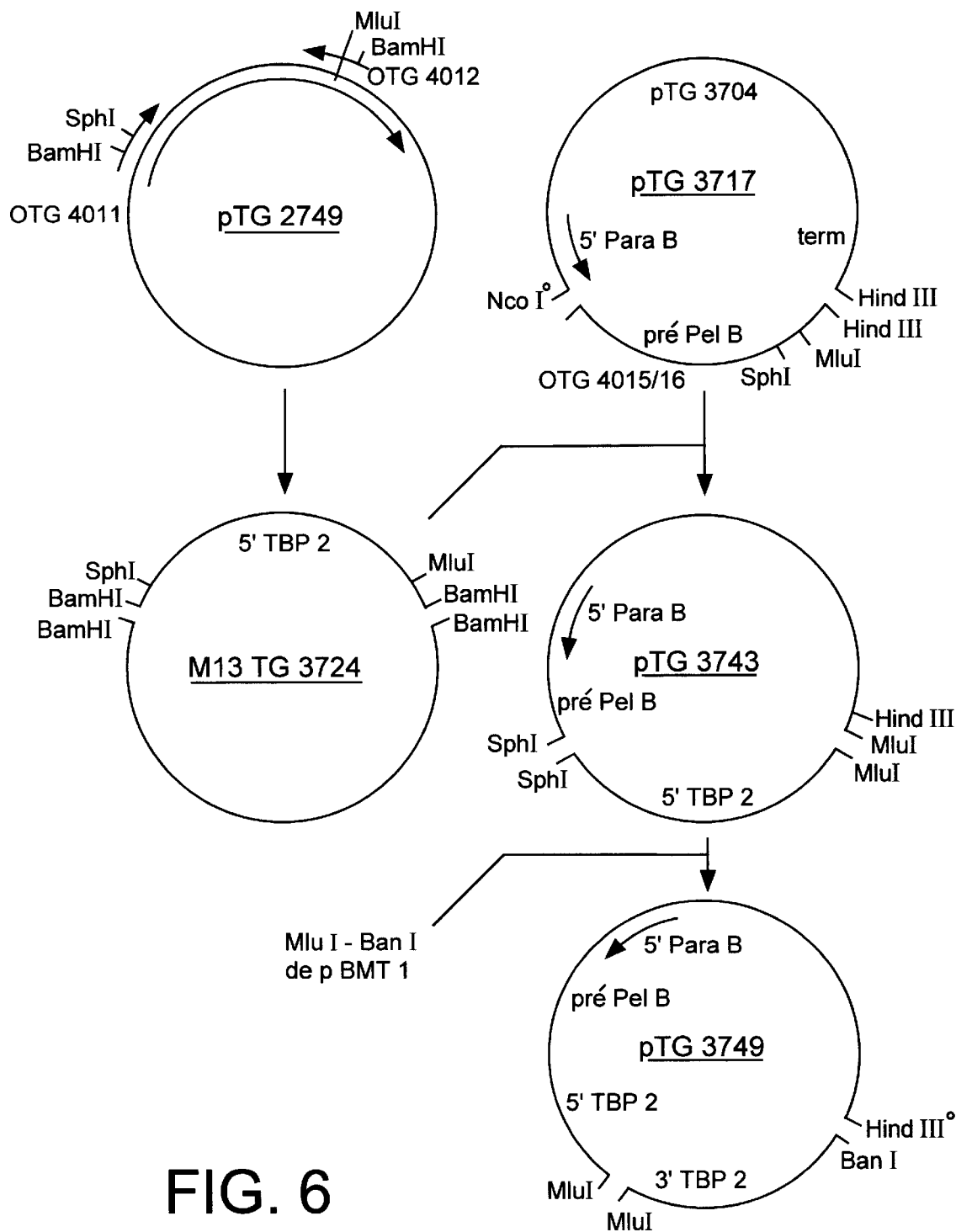
FIG. 6 represents the methodology which was used to construct the expression vector pTG3749.
Figure 9:
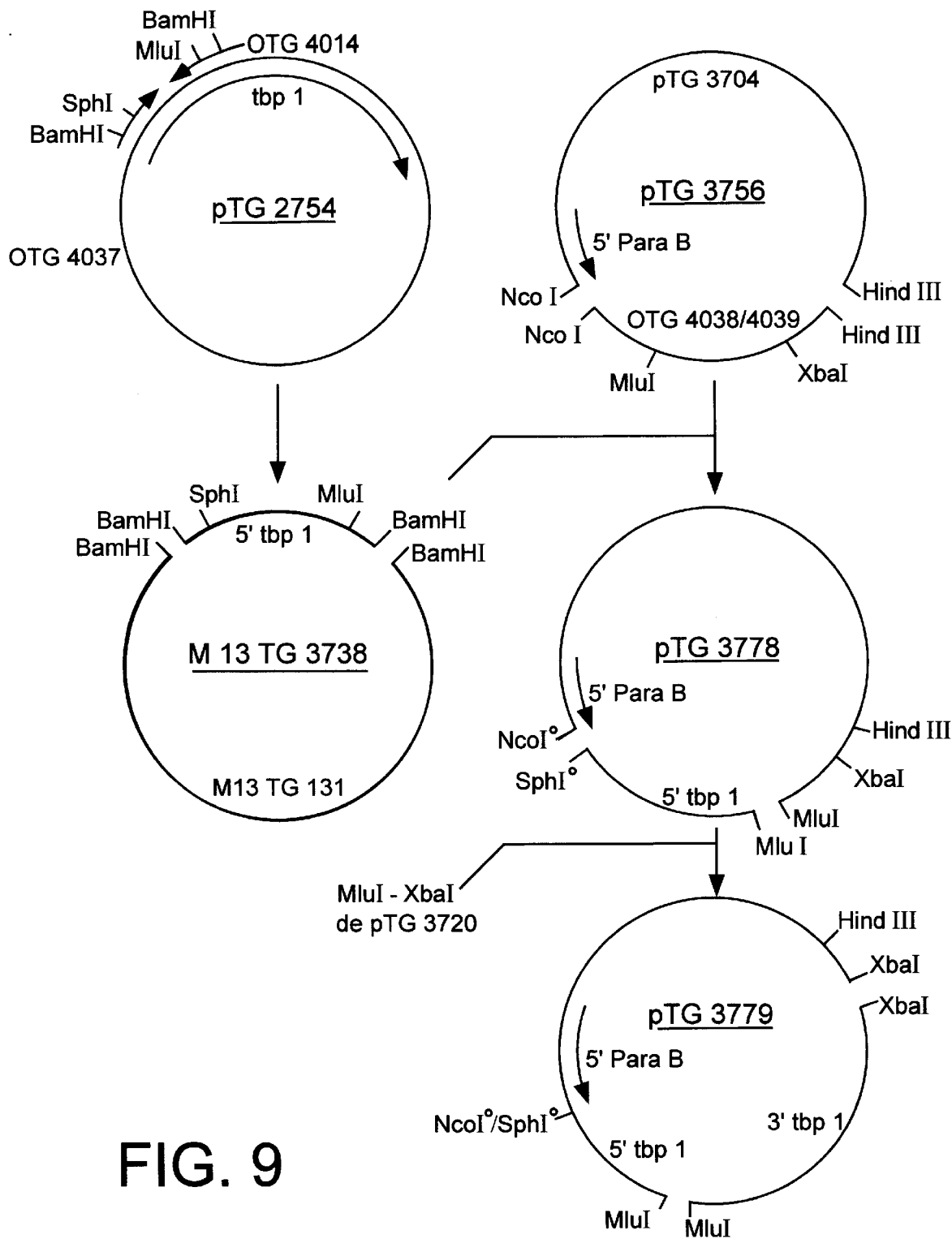
FIG. 9 represents the methodology which was used to construct the expression vector pTG3779.
Figure 10:
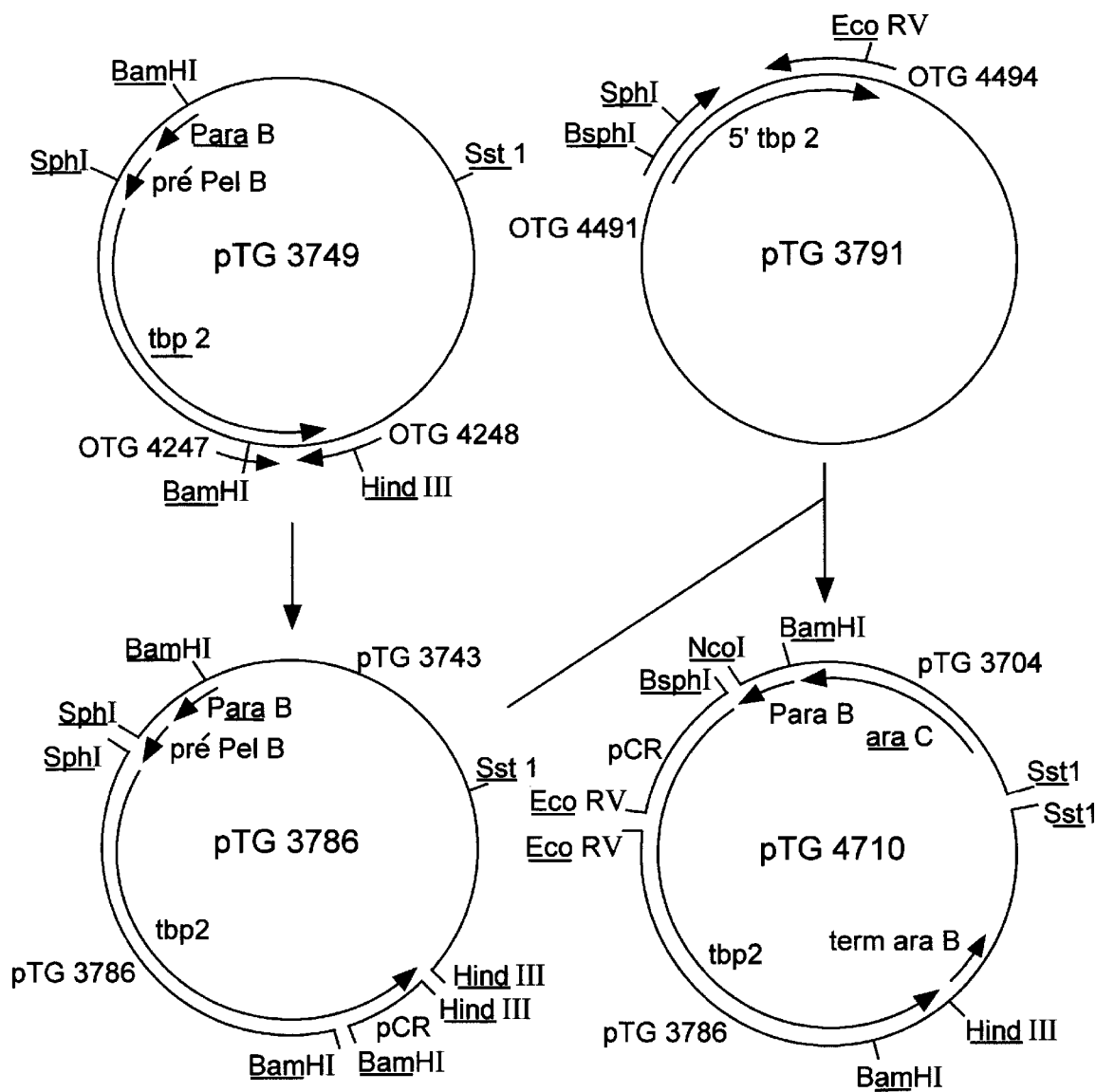
FIG. 10 represents the methodology which was used to construct the expression vector pTG4710.

From the plasmid pTG2749, a fragment including the region which encodes the N-terminal portion of Tbp2, up to the internal MluI site, as shown in FIG. 6, was generated by PCR using the primers OTG4011 and OTG4012 [SEQ ID NOS: 50–51].

```
OTG4011 :
        BamHI   SphI
5' AAAAAGGATCC/GCA TGC CTG GGT GGC GGC GGC AGT TTC 3'
                  Cys Leu Gly ....

OTG4012 :
        BamHI                  MluI
5'  AAAAGGATCCG AAT GGT GTA ACG CGT AGT TTT TAT 3'
```

The fragment generated by PCR was digested with BamHI and then inserted into the BamHI site of the phage M13TG131 to give M13TG3724. The sequence of this fragment was checked by sequencing.

The region which encodes the N-terminal portion of Tbp2 was recovered from M13TG3724 in the form of an SphI-MluI fragment which was then inserted into pTG3717 previously digested with SphI and MluI, to give the plasmid pTG3743.

From the plasmid pBMT1, the region which encodes the C-terminal portion of Tbp2 was recovered in the form of an MluI-BanI fragment whose BanI sticky end had been made blunt by treatment with Klenow polymerase. This fragment was inserted into pTG3743 previously digested with HindIII, treated with Klenow polymerase and finally digested with MluI. The plasmid pTG3749 was thus obtained.

3B. Production of the Tbp2 subunit.

E. coli MC1061 (Casadaban & Cohen, J. Mol. Biol. (1980) 138: 179) is transformed with pTG3749 and then cultured at 37° C. in LB medium supplemented with 2 g/l of glycerol and 100 μg/ml of ampicillin. To the culture in exponential phase, is added 0.2 g/l of arabinose. The incubation is continued for a further 6 h. The expression was observed less than one hour after the addition of arabinose.

Polyacrylamide gel electrophoresis of a sample of the total cell lysate shows the presence of a protein of about 70 kD which is capable of binding peroxydase-labelled human transferrin.

EXAMPLE 4

Expression of the DNA fragment which encodes the Tbp2 subunit of the strain IM2169

4A. Construction of the expression vector pTG3779.

A synthetic fragment consisting of the oligonucleotides OTG4038 and OTG4039 [SEQ ID NOS: 52–53] previously paired, was inserted into the plasmid pTG3704 digested with NcoI and HindIII, thus generating the plasmid pTG3756.

OTG4038: 5' CATGGCTGCAGGRACCACGCGTGAAT-TCCCCGGGTCTAGA 3'

OTG4039: 5' AGCTTCTAGACCCGGGGAAT-TCACGCGTGGTACCTGCAGC 3'

From the plasmid pTG2754, a fragment including the region which encodes the N-terminal end of the precursor of Tbp1 up to the MluI site was generated by PCR using the primers OTG4037 and OTG4014 [SEQ ID NOS: 54–55].

```
OTG4037 :
5' TTTCCCGGATCCGC ATG CAA CAG CAA CAT TTG TTC CGA TTA 3
                 BamHI   SphI

OTG4014 :
5' AAAAGGATCCGGGGTCGTAACGCGTCAGGTCGCGG 3'
         BamHI         MluI
```

This PCR fragment was digested with BamHI and cloned into the BamHI site of M13TG131 in order to generate M13TG3738. The sequence of this fragment was checked.

M13TG3738 was then linearised with SphI, treated with T4 DNA polymerase so as to make the ends blunt, and then digested with MluI in order to isolate the fragment carrying the region which encodes the N-terminal end of the precursor of Tbp1.

This fragment was inserted into NcoI-digested pTG3756, treated with T4 DNA polymerase and then digested with MluI in order to generate the plasmid pTG3778. The sequence of the NcoI°/SphI° junction was checked.

The MluI-XbaI fragment of pTG3720 encoding the main part of Tbp1 (3'tbp1) was inserted into the plasmid pTG3778. The final plasmid thus obtained is the plasmid pTG3779.

4B. Production of the Tbp1 subunit.

E. coli MC1061 was transformed with pTG3779 and then cultured at 37° C. in LB medium. To the culture in exponential phase, is added 0.2 g/l of arabinose. The incubation was continued for 4 hours.

Polyacrylamide gel electrophoresis of a sample of the total cell lysate showed the presence of a protein of about 100 kD which is recognised by the anti-receptor antibodies.

EXAMPLE 5

Expression of the DNA fragment which encodes the Tbp2 subunit of the strain IM2394 (construct with the homologous signal sequence)

5A. Construction of the expression vector pTG4710.

From the plasmid pTG3749, a fragment which encodes the C-terminal portion of Tbp2 (from the internal BamHI site) and containing an HindIII restriction site downstream of the translational termination codon of tbp2 was generated by PCR using the primers OTG4247 and OTG4248 [SEQ ID NOS: 56–57].

```
OTG4247 : 5' GGCTTTGCGCTGGATCCGCAAAATACC 3'
                       BamHI

OTG4248 :
5' CCCAAAAGATCTCCAAGCTTGAAGCCTTATTCTCGATTGTTCGGCAGCC 3'
                 HindIII
```

The fragment generated by PCR was digested with HindIII and BamHI and inserted simultaneously with the SphI-BamHI fragment of pTG3749 which encodes the N-terminal part of mature Tbp2 into the vector pTG3743 digested with SphI and HindIII to give the plasmid pTG3786. The sequence of the PCR-amplified fragment was checked.

From the plasmid pTG3791, a fragment which encodes the N-terminal portion of the precursor of Tbp2 up to the internal EcoRV site was generated by PCR using the primers OTG4491 and OTG4494 [SEQ ID NOS: 58–59].

```
              BspHI
5' TTTTTTGGATCCTCATG AAC AAT CCA TTG GTA AAT CAG GCT
                    Met Asn Asn Pro Leu Val Asn Glu Ala

SphI
GCT ATG GTG CTG CCT GTG TTT TTG TTG AGT GCA TGC CTG GGT
Ala Met Val Leu Pro Val Phe Leu Leu Ser Ala Cys Leu Gly
```

Cleavage of the signal peptide

```
OTG4494 :
5' TTTTTTGGATCCGATATCCGTCAGGTCCAAAAAGAACTATATTATTC 3'
             EcoRV
```

The fragment generated by PCR was then digested with BspHI and EcoRV and ligated simultaneously into the NcoI-SstI fragments of pTG3704 containing the araC gene and the araB promoter, and into the EcoRV-Sst1 fragments of pTG3786 containing the 3' portion of the tbp2 and the araB terminator. The resulting plasmid pTG4710 was checked by sequencing (sequence of the PCR-amplified fragment).

5B. Production of the Tbp2 subunit.

E. coli Xac-I (Normanly et al., Proc. Natl. Acad. Sci. (1986) 83: 6548) is transformed with the plasmid pTG4710 and then cultured at 37° C. in M9 medium+0.5% succinate+50 μg/ml arginine+100 μg/ml ampicillin. In the exponential phase, 0.2% arabinose is added. After various induction times (1 h to 3 h), cells are collected and extracts are prepared. Western blot analysis followed by visualisation of Tbp2 using transferrin-peroxydase made it possible to show that most of Tbp2 occurs in the form of a precursor. Analysis of the extracts by SDS-PAGE followed by staining of the proteins with Coomassie blue made it possible to detect a high production of protein (evaluated at about 5 to 10% of the total proteins). Labelling experiments in vivo with titrated palmitate and glycerol made it possible to show that only the mature form is lipidated.

EXAMPLE 6
Expression of the DNA fragment which encodes the Tbp2 subunit of the strain IM2394 (construct with the rlpB signal sequence)

6A. Construction of the expression vector pTG4764.

From pTG3786 a fragment which encodes the RlpB signal peptide (Takase et al., J. Bacteriol. (1987) 169: 5692) and the beginning of the sequence which encodes mature Tbp2 up to the internal EcoRV site was generated by PCR using the primers OTG4494 and OTG4651 [SEQ ID NO: 60].

OTG4494: cf Example 1. 1

```
OTG4651 :
           BspHI
5' TTTTTTTCATG AGA TAC CTG GCA ACA TTG TTG TTA TCT
             Met Arg Tyr Leu Ala Thr Leu Leu Leu Ser

CTG GCG GTG TTA ATC ACC GCC GGG TGC CTG GGT GGC
Leu Ala Val Leu Ile Thr Ala Gly Cys Leu Gly ...
GGC GGC AGT TTC 3'
   cleavage of the signal peptide
```

GGC GGC AGT TTC 3'

The PCR fragment was then digested with BspHI and EcoRV and inserted simultaneously with the EcoRV-HindIII fragment of the pTG3786 carrying the 3' portion of the tbp2 gene, into the vector pTG3704 digested with NcoI and HindIII in order to generate the plasmid pTG4764. The sequence of the PCR-amplified fragment was checked.

6B. Production of the Tbp2 subunit.

E. coli Xac-I is transformed with the plasmid pTG4764 and then cultured at 37° C. in M9 medium+0.5% succinate+50 μg/ml arginine+100 μg/ml ampicillin. In the exponential phase, 0.2% arabinose is added. After various induction times (1 h to 3 h), cells are collected and extracts are prepared. A Western blot analysis followed by visualisation with transferrin-peroxydase made it possible to detect a predominant band whose molecular weight corresponds to that of purified mature Tbp2. The protein is detected in the extracts after SDS-PAGE and staining of the proteins with Coomassie blue (level of production evaluated at about 2 to 5% of the total proteins). Labelling experiments in vivo with tritiated palmitate and glycerol made it possible to show that the protein thus produced is lipidated. The quantity of lipidated mature Tbp2 form produced by the strain Xac-I/pTG4764 is greater than that produced by the strain Xac-I/pTG4710.

We claim:

1. A composition of matter comprising two proteins and a carrier therefor, wherein said proteins are recognized by an antiserum against the transferrin receptor of the strain IM2394 or IM2169 of *N. meningitidis*, wherein said proteins are obtained by culturing a host cell transformed by an expression cassette which comprises a DNA sequence which encodes the amino acid sequence of SEQ ID NO: 2, from position −20 to position 579; and further comprises a DNA sequence which encodes the amino acid sequence of SEQ ID NO: 8, from position −20 to position 691;

further wherein said expression cassette does not comprise the DNA sequence encoding the amino acid sequence of SEQ ID NO: 4, from position −24 to position 884, nor the DNA sequence encoding the amino acid sequence of SEQ ID NO: 6 from position −24 to position 887;

said DNA sequences being placed under the control of elements required for their expression; and recovering the proteins from the culture.

2. A composition of matter comprising two proteins and a carrier therefor, wherein said proteins are recognized by an antiserum against the transferrin receptor of the strain IM2394 or IM2169 of *N. meningitides*, wherein said proteins are obtained by culturing a host cell transformed by an expression cassette which comprises a DNA sequence which encodes the amino acid sequence of SEQ ID NO: 2, from position 1 to position 579; and further comprises a DNA sequence which encodes the amino acid sequence of SEQ ID NO: 8, from position 1 to position 691; further wherein said expression cassette does not comprise the DNA sequence encoding the amino acid sequence of SEQ ID NO: 4, from position 1 to position 884, nor the DNA sequence encoding the amino acid sequence of SEQ ID NO: 6 from position 1 to position 887;

said DNA sequences being placed under the control of elements required for their expression; and recovering the proteins from the culture.

3. A composition of matter comprising a protein and a carrier therefor, wherein said protein is recognized by an antiserum against the transferrin receptor of the strain IM2394 or IM2169 of *N. meningitidis*, and further wherein said protein is obtained by culturing a host cell transformed by an expression cassette which comprises a DNA sequence which encodes the Tbp2 subunit of *N. meningitidis*, and does not encode the Tbp1 subunit, wherein said Tbp2 subunit has an amino acid sequence selected from the group consisting of:

SEQ ID NO: 2, from position −20 to position 579; and

SEQ ID NO: 8, from position −20 to position 691, said DNA sequence being placed under the control of the elements required for its expression; and recovering the protein from the culture.

4. A composition of matter comprising a protein and a carrier therefor, wherein said protein is recognized by an antiserum against the transferrin receptor of the strain IM2394 or IM2169 of *N. meningitidis*, and further wherein said protein is obtained by:

culturing a host cell transformed by an expression cassette which comprises a DNA sequence which encodes the Tbp2 subunit of *N. meningitidis*, and does not encode the Tbp1 subunit, wherein said Tbp2 subunit has an amino acid sequence selected from the group consisting of:

SEQ ID NO: 2, from position 1 to position 579; and

SEQ ID NO: 8, from position 1 to position 691, said DNA sequence being placed under the control of the elements required for its expression; and recovering the protein from the culture.

5. A pharmaceutical composition comprising as an active ingredient two proteins capable of being recognized by an antiserum against the transferrin receptor of the strain IM2394 or IM2169 of *N. meningitidis*, and a carrier therefor, wherein said proteins are obtained by culturing a host cell transformed by an expression cassette which comprises a DNA sequence which encodes the amino acid sequence of SEQ ID NO: 2, from position −20 to position 579; and further comprises a DNA sequence which encodes the amino acid sequence of SEQ ID NO: 8, from position −20 to position 691; further wherein said expression cassette does not comprise the DNA sequence encoding the amino acid sequence of SEQ ID NO: 4, from position −24 to position 884, nor the DNA sequence encoding the amino acid sequence of SEQ ID NO: 6 from position −24 to position 887;

said DNA sequences being placed under the control of elements required for its expression;

and recovering the proteins from the culture.

6. A pharmaceutical composition comprising as an active ingredient two proteins capable of being recognized by an antiserum against the transferrin receptor of the strain IM2394 or IM2169 of *N. meningitides*, and a carrier therefor, wherein said proteins are obtained by culturing a host cell transformed by an expression cassette which comprises a DNA sequence which encodes the amino acid sequence of SEQ ID NO: 2, from position 1 to position 579; and further comprises a DNA sequence which encodes the amino acid sequence of SEQ ID NO: 8, from position 1 to position 691; further wherein said expression cassette does not comprise the DNA sequence encoding the amino acid sequence of SEQ ID NO: 4, from position 1 to position 884, nor the DNA sequence encoding the amino acid sequence of SEQ ID NO: 6 from position 1 to position 887;

said DNA sequences being placed under the control of elements required for its expression;

and recovering the proteins from the culture.

7. A pharmaceutical composition comprising as an active ingredient a protein capable of being recognized by an antiserum against the transferrin receptor of the strain IM2394 or IM2169 of *N. meningitidis* and a carrier therefor, wherein said protein is obtained by culturing a host cell transformed by an expression cassette which comprises a DNA sequence which encodes the Tbp2 subunit of *N. meningitidis*, and does not encode the Tbp1 subunit, wherein said Tbp2 subunit has an amino acid sequence selected from the group consisting of:

SEQ ID NO: 2, from position −20 to position 579; and

SEQ ID NO: 8, from position −20 to position 691, said DNA sequence being placed under the control of the elements required for its expression;

and recovering the protein from the culture.

8. A pharmaceutical composition comprising as an active ingredient a protein capable of being recognized by an antiserum against the transferrin receptor of the strain IM2394 or IM2169 of *N. meningitidis*, and a carrier therefor, wherein said protein is obtained by culturing a host cell transformed by an expression cassette which comprises a DNA sequence which encodes the Tbp2 subunit of *N. meningitidis*, and does not encode the Tbp1 subunit, wherein said Tbp2 subunit has an amino acid sequence selected from the group consisting of:

SEQ ID NO: 2, from position 1 to position 579; and

SEQ ID NO: 8, from position 1 to position 691, said DNA sequence being placed under the control of the elements required for its expression;

and recovering the protein from the culture.

* * * * *

SEQUENCE LISTING (1) GENERAL INFORMATION:

(iii) NUMBER OF SEQUENCES: 62

(2) INFORMATION FOR SEQ ID NO:1:

(i) SEQUENCE CHARACTERISTICS:
      (A) LENGTH: 1808 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: DNA which encodes Tbp2 subunit of transferrin receptor
      (B) STRAIN: Neisseria meningitidis IM2394

(ix) FEATURE:
 &

```
GGA TAT GTT TAC CTT AAT AAA AAT AAT ATT GAT ATT AAG AAT AAT ATA        480
Gly Tyr Val Tyr Leu Asn Lys Asn Asn Ile Asp Ile Lys Asn Asn Ile
125                 130                 135                 140

GTT CTT TTT GGA CCT GAC GGA TAT CTT TAC TAT AAA GGG AAA GAA CCT        528
Val Leu Phe Gly Pro Asp Gly Tyr Leu Tyr Tyr Lys Gly Lys Glu Pro
                145                 150                 155

TCC AAG GAG CTG CCA TCG GAA AAG ATA ACT TAT AAA GGT ACT TGG GAT        576
Ser Lys Glu Leu Pro Ser Glu Lys Ile Thr Tyr Lys Gly Thr Trp Asp
            160                 165                 170

TAT GTT ACT GAT GCT ATG GAA AAA CAA AGG TTT GAA GGA TTG GGT AGT        624
Tyr Val Thr Asp Ala Met Glu Lys Gln Arg Phe Glu Gly Leu Gly Ser
        175                 180                 185

GCA GCA GGA GGA GAT AAA TCG GGG GCG TTG TCT GCA TTA GAA GAA GGG        672
Ala Ala Gly Gly Asp Lys Ser Gly Ala Leu Ser Ala Leu Glu Glu Gly
    190                 195                 200

GTA TTG CGT AAT CAG GCA GAG GCA TCA TCC GGT CAT ACC GAT TTT GGT        720
Val Leu Arg Asn Gln Ala Glu Ala Ser Ser Gly His Thr Asp Phe Gly
205                 210                 215                 220

ATG ACT AGT GAG TTT GAG GTT GAT TTT TCT GAT AAA ACA ATA AAG GGC        768
Met Thr Ser Glu Phe Glu Val Asp Phe Ser Asp Lys Thr Ile Lys Gly
                225                 230                 235

ACA CTT TAT CGT AAC AAC CGT ATT ACT CAA AAT AAT AGT GAA AAC AAA        816
Thr Leu Tyr Arg Asn Asn Arg Ile Thr Gln Asn Asn Ser Glu Asn Lys
            240                 245                 250

CAA ATA AAA ACT ACG CGT TAC ACC ATT CAA GCA ACT CTT CAC GGC AAC        864
Gln Ile Lys Thr Thr Arg Tyr Thr Ile Gln Ala Thr Leu His Gly Asn
        255                 260                 265

CGT TTC AAA GGT AAG GCG TTG GCG GCA GAT AAA GGT GCA ACA AAT GGA        912
Arg Phe Lys Gly Lys Ala Leu Ala Ala Asp Lys Gly Ala Thr Asn Gly
    270                 275                 280

AGT CAT CCC TTT ATT TCC GAC TCC GAC AGT TTG GAA GGC GGA TTT TAC        960
Ser His Pro Phe Ile Ser Asp Ser Asp Ser Leu Glu Gly Gly Phe Tyr
285                 290                 295                 300

GGG CCG AAA GGC GAG GAA CTT GCC GGT AAA TTC TTG AGC AAC GAC AAC       1008
Gly Pro Lys Gly Glu Glu Leu Ala Gly Lys Phe Leu Ser Asn Asp Asn
                305                 310                 315

AAA GTT GCA GCG GTG TTT GGT GCG AAG CAG AAA GAT AAG AAG GAT GGG       1056
Lys Val Ala Ala Val Phe Gly Ala Lys Gln Lys Asp Lys Lys Asp Gly
            320                 325                 330

GAA AAC GCG GCA GGG CCT GCA ACG GAA ACC GTG ATA GAT GCA TAC CGT       1104
Glu Asn Ala Ala Gly Pro Ala Thr Glu Thr Val Ile Asp Ala Tyr Arg
        335                 340                 345

ATT ACC GGC GAG GAG TTT AAG AAA GAG CAA ATA GAC AGT TTT GGA GAT       1152
Ile Thr Gly Glu Glu Phe Lys Lys Glu Gln Ile Asp Ser Phe Gly Asp
    350                 355                 360

GTG AAA AAG CTG CTG GTT GAC GGA GTG GAG CTT TCA CTG CTG CCG TCT       1200
Val Lys Lys Leu Leu Val Asp Gly Val Glu Leu Ser Leu Leu Pro Ser
365                 370                 375                 380

GAG GGC AAT AAG GCG GCA TTT CAG CAC GAG ATT GAG CAA AAC GGC GTG       1248
Glu Gly Asn Lys Ala Ala Phe Gln His Glu Ile Glu Gln Asn Gly Val
                385                 390                 395

AAG GCA ACG GTG TGT TGT TCC AAC TTG GAT TAC ATG AGT TTT GGG AAG       1296
Lys Ala Thr Val Cys Cys Ser Asn Leu Asp Tyr Met Ser Phe Gly Lys
            400                 405                 410

CTG TCA AAA GAA AAT AAA GAC GAT ATG TTC CTG CAA GGT GTC CGC ACT       1344
Leu Ser Lys Glu Asn Lys Asp Asp Met Phe Leu Gln Gly Val Arg Thr
        415                 420                 425

CCA GTA TCC GAT GTG GCG GCA AGG ACG GAG GCA AAC GCC AAA TAT CGC       1392
Pro Val Ser Asp Val Ala Ala Arg Thr Glu Ala Asn Ala Lys Tyr Arg
    430                 435                 440
```

```
GGT ACT TGG TAC GGA TAT ATT GCC AAC GGC ACA AGC TGG AGC GGC GAA      1440
Gly Thr Trp Tyr Gly Tyr Ile Ala Asn Gly Thr Ser Trp Ser Gly Glu
445                 450                 455                 460

GCC TCC AAT CAG GAA GGT GGT AAT AGG GCA GAG TTT GAC GTG GAT TTT      1488
Ala Ser Asn Gln Glu Gly Gly Asn Arg Ala Glu Phe Asp Val Asp Phe
                465                 470                 475

TCC ACT AAA AAA ATC AGT GGC ACA CTC ACG GCA AAA GAC CGT ACG TCT      1536
Ser Thr Lys Lys Ile Ser Gly Thr Leu Thr Ala Lys Asp Arg Thr Ser
            480                 485                 490

CCT GCG TTT ACT ATT ACT GCC ATG ATT AAG GAC AAC GGT TTT TCA GGT      1584
Pro Ala Phe Thr Ile Thr Ala Met Ile Lys Asp Asn Gly Phe Ser Gly
        495                 500                 505

GTG GCG AAA ACC GGT GAA AAC GGC TTT GCG CTG GAT CCG CAA AAT ACC      1632
Val Ala Lys Thr Gly Glu Asn Gly Phe Ala Leu Asp Pro Gln Asn Thr
    510                 515                 520

GGA AAT TCC CAC TAT ACG CAT ATT GAA GCC ACT GTA TCC GGC GGT TTC      1680
Gly Asn Ser His Tyr Thr His Ile Glu Ala Thr Val Ser Gly Gly Phe
525                 530                 535                 540

TAC GGC AAA AAC GCC ATC GAG ATG GGC GGA TCG TTC TCA TTT CCG GGA      1728
Tyr Gly Lys Asn Ala Ile Glu Met Gly Gly Ser Phe Ser Phe Pro Gly
                545                 550                 555

AAT GCA CCA GAG GGA AAA CAA GAA AAA GCA TCG GTG GTA TTC GGT GCG      1776
Asn Ala Pro Glu Gly Lys Gln Glu Lys Ala Ser Val Val Phe Gly Ala
            560                 565                 570

AAA CGC CAA CAG CTT GTG CAA TAAGCACGGC T                             1808
Lys Arg Gln Gln Leu Val Gln
        575
```

(2) INFORMATION FOR SEQ ID NO:2:

(i) SEQUENCE CHARACTERISTICS:
        (A) LENGTH: 599 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Asn Pro Leu Val Asn Gln Ala Ala Met Val Leu Pro Val Phe
-20                 -15                 -10                  -5

Leu Leu Ser Ala Cys Leu Gly Gly Gly Ser Phe Asp Leu Asp Ser
                 1                   5                  10

Val Glu Thr Val Gln Asp Met His Ser Lys Pro Lys Tyr Glu Asp Glu
            15                  20                  25

Lys Ser Gln Pro Glu Ser Gln Gln Asp Val Ser Glu Asn Ser Gly Ala
        30                  35                  40

Ala Tyr Gly Phe Ala Val Lys Leu Pro Arg Arg Asn Ala His Phe Asn
45                  50                  55                  60

Pro Lys Tyr Lys Glu Lys His Lys Pro Leu Gly Ser Met Asp Trp Lys
                65                  70                  75

Lys Leu Gln Arg Gly Glu Pro Asn Ser Phe Ser Glu Arg Asp Glu Leu
            80                  85                  90

Glu Lys Lys Arg Gly Ser Ser Glu Leu Ile Glu Ser Lys Trp Glu Asp
        95                  100                 105

Gly Gln Ser Arg Val Val Gly Tyr Thr Asn Phe Thr Tyr Val Arg Ser
    110                 115                 120

Gly Tyr Val Tyr Leu Asn Lys Asn Asn Ile Asp Ile Lys Asn Asn Ile
125                 130                 135                 140
```

-continued

Val Leu Phe Gly Pro Asp Gly Tyr Leu Tyr Lys Gly Lys Glu Pro
                145                 150                 155

Ser Lys Glu Leu Pro Ser Glu Lys Ile Thr Tyr Lys Gly Thr Trp Asp
            160                 165                 170

Tyr Val Thr Asp Ala Met Glu Lys Gln Arg Phe Glu Gly Leu Gly Ser
        175                 180                 185

Ala Ala Gly Gly Asp Lys Ser Gly Ala Leu Ser Ala Leu Glu Glu Gly
    190                 195                 200

Val Leu Arg Asn Gln Ala Glu Ala Ser Ser Gly His Thr Asp Phe Gly
205                 210                 215                 220

Met Thr Ser Glu Phe Glu Val Asp Phe Ser Asp Lys Thr Ile Lys Gly
                225                 230                 235

Thr Leu Tyr Arg Asn Asn Arg Ile Thr Gln Asn Asn Ser Glu Asn Lys
            240                 245                 250

Gln Ile Lys Thr Thr Arg Tyr Thr Ile Gln Ala Thr Leu His Gly Asn
        255                 260                 265

Arg Phe Lys Gly Lys Ala Leu Ala Ala Asp Lys Gly Ala Thr Asn Gly
    270                 275                 280

Ser His Pro Phe Ile Ser Asp Ser Asp Ser Leu Glu Gly Gly Phe Tyr
285                 290                 295                 300

Gly Pro Lys Gly Glu Glu Leu Ala Gly Lys Phe Leu Ser Asn Asp Asn
                305                 310                 315

Lys Val Ala Ala Val Phe Gly Ala Lys Gln Lys Asp Lys Lys Asp Gly
            320                 325                 330

Glu Asn Ala Ala Gly Pro Ala Thr Glu Thr Val Ile Asp Ala Tyr Arg
        335                 340                 345

Ile Thr Gly Glu Glu Phe Lys Lys Glu Gln Ile Asp Ser Phe Gly Asp
    350                 355                 360

Val Lys Lys Leu Leu Val Asp Gly Val Glu Leu Ser Leu Leu Pro Ser
365                 370                 375                 380

Glu Gly Asn Lys Ala Ala Phe Gln His Glu Ile Glu Gln Asn Gly Val
                385                 390                 395

Lys Ala Thr Val Cys Cys Ser Asn Leu Asp Tyr Met Ser Phe Gly Lys
            400                 405                 410

Leu Ser Lys Glu Asn Lys Asp Asp Met Phe Leu Gln Gly Val Arg Thr
        415                 420                 425

Pro Val Ser Asp Val Ala Ala Arg Thr Glu Ala Asn Ala Lys Tyr Arg
    430                 435                 440

Gly Thr Trp Tyr Gly Tyr Ile Ala Asn Gly Thr Ser Trp Ser Gly Glu
445                 450                 455                 460

Ala Ser Asn Gln Glu Gly Gly Asn Arg Ala Glu Phe Asp Val Asp Phe
                465                 470                 475

Ser Thr Lys Ile Ser Gly Thr Leu Thr Ala Lys Asp Arg Thr Ser
            480                 485                 490

Pro Ala Phe Thr Ile Thr Ala Met Ile Lys Asp Asn Gly Phe Ser Gly
        495                 500                 505

Val Ala Lys Thr Gly Glu Asn Gly Phe Ala Leu Asp Pro Gln Asn Thr
    510                 515                 520

Gly Asn Ser His Tyr Thr His Ile Glu Ala Thr Val Ser Gly Gly Phe
525                 530                 535                 540

Tyr Gly Lys Asn Ala Ile Glu Met Gly Gly Ser Phe Ser Phe Pro Gly
                545                 550                 555

Asn Ala Pro Glu Gly Lys Gln Glu Lys Ala Ser Val Val Phe Gly Ala

-continued

```
                         560                 565                 570
Lys Arg Gln Gln Leu Val Gln
        575

(2) INFORMATION FOR SEQ ID NO:3:

(i) SEQUENCE CHARACTERISTICS:
        (A) LENGTH: 2800 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: DNA encodes Tpb1 subunit of transferrin
            receptor
        (B) STRAIN: Neisseria meningitidis IM2394

(ix) FEATURE:
        (A) NAME/KEY: sig_peptide
        (B) LOCATION: 40..111

(ix) FEATURE:
        (A) NAME/KEY: mat_peptide
        (B) LOCATION: 112..2763

(ix) FEATURE:
        (A) NAME/KEY: CDS
        (B) LOCATION: 40..2763

(xi) SEQUENCE DESCRIPTION: SEQ ID NO:3:

CTTCCGATGC CGTCTGAAAG CGAAGATTAG GGAAACACT ATG CAA CAG CAA CAT           54
                                            Met Gln Gln Gln His
                                            -24               -20

TTG TTC CGA TTA AAT ATT TTA TGC CTG TCT TTA ATG ACC GCG CTG CCC        102
Leu Phe Arg Leu Asn Ile Leu Cys Leu Ser Leu Met Thr Ala Leu Pro
            -15                 -10                  -5

GTT TAT GCA GAA AAT GTG CAA GCC GAA CAA GCA CAG GAA AAA CAG TTG        150
Val Tyr Ala Glu Asn Val Gln Ala Glu Gln Ala Gln Glu Lys Gln Leu
             1               5                  10

GAT ACC ATA CAG GTA AAA GCC AAA AAA CAG AAA ACC CGC CGC GAT AAC        198
Asp Thr Ile Gln Val Lys Ala Lys Lys Gln Lys Thr Arg Arg Asp Asn
        15                  20                  25

GAA GTG ACC GGG CTG GGC AAG TTG GTC AAG TCT TCC GAT ACG CTA AGT        246
Glu Val Thr Gly Leu Gly Lys Leu Val Lys Ser Ser Asp Thr Leu Ser
 30              35                  40                      45

AAA GAA CAG GTT TTG AAT ATC CGA GAC CTG ACC CGT TAT GAT CCG GGT        294
Lys Glu Gln Val Leu Asn Ile Arg Asp Leu Thr Arg Tyr Asp Pro Gly
                50                  55                  60

ATT GCC GTG GTC GAA CAG GGT CGG GGC GCA AGT TCC GGC TAT TCA ATA        342
Ile Ala Val Val Glu Gln Gly Arg Gly Ala Ser Ser Gly Tyr Ser Ile
             65                  70                  75

CGC GGC ATG GAT AAA AAC CGC GTT TCC TTA ACG GTA GAC GGC GTT TCG        390
Arg Gly Met Asp Lys Asn Arg Val Ser Leu Thr Val Asp Gly Val Ser
         80                  85                  90

CAA ATA CAG TCC TAC ACC GCG CAG GCG GCA TTG GGT GGG ACG AGG ACG        438
Gln Ile Gln Ser Tyr Thr Ala Gln Ala Ala Leu Gly Gly Thr Arg Thr
     95                 100                 105

GCG GGT AGC AGC GGC GCA ATC AAT GAA ATC GAG TAT GAA AAC GTC AAG        486
Ala Gly Ser Ser Gly Ala Ile Asn Glu Ile Glu Tyr Glu Asn Val Lys
110                 115                 120                 125

GCC GTT GAA ATC AGC AAG GGT TCG AAT TCA TCA GAA TAC GGA AAC GGC        534
Ala Val Glu Ile Ser Lys Gly Ser Asn Ser Ser Glu Tyr Gly Asn Gly
            130                 135                 140
```

-continued

| | |
|---|---|
| GCA TTG GCA GGT TCG GTC GCA TTT CAA ACC AAA ACC GCA GCC GAC ATT<br>Ala Leu Ala Gly Ser Val Ala Phe Gln Thr Lys Thr Ala Ala Asp Ile<br>             145                   150                 155 | 582 |
| ATC GGA GAG GGA AAA CAG TGG GGC ATT CAG AGT AAA ACT GCC TAT TCG<br>Ile Gly Glu Gly Lys Gln Trp Gly Ile Gln Ser Lys Thr Ala Tyr Ser<br>             160                   165                 170 | 630 |
| GGA AAA GAC CAT GCC CTG ACG CAA TCC CTT GCG CTT GCC GGA CGC AGC<br>Gly Lys Asp His Ala Leu Thr Gln Ser Leu Ala Leu Ala Gly Arg Ser<br>175                         180                   185 | 678 |
| GGC GGC GCG GAA GCC CTC CTT ATT TAT ACT AAA CGG CGG GGT CGG GAA<br>Gly Gly Ala Glu Ala Leu Leu Ile Tyr Thr Lys Arg Arg Gly Arg Glu<br>190                   195                   200                 205 | 726 |
| ATC CAT GCG CAT AAA GAT GCC GGC AAG GGT GTG CAG AGC TTC AAC CGG<br>Ile His Ala His Lys Asp Ala Gly Lys Gly Val Gln Ser Phe Asn Arg<br>             210                   215                 220 | 774 |
| CTG GTG TTG GAC GAG GAC AAG AAG GAG GGT GGC AGT CAG TAC AGA TAT<br>Leu Val Leu Asp Glu Asp Lys Lys Glu Gly Gly Ser Gln Tyr Arg Tyr<br>                   225                   230                 235 | 822 |
| TTC ATT GTC GAA GAA GAA TGC CAC AAT GGA TAT GCG GCC TGT AAA AAC<br>Phe Ile Val Glu Glu Glu Cys His Asn Gly Tyr Ala Ala Cys Lys Asn<br>             240                   245                 250 | 870 |
| AAG CTG AAA GAA GAT GCC TCG GTC AAA GAT GAG CGC AAA ACC GTC AGC<br>Lys Leu Lys Glu Asp Ala Ser Val Lys Asp Glu Arg Lys Thr Val Ser<br>                   255                   260                 265 | 918 |
| ACG CAG GAT TAT ACC GGC TCC AAC CGC TTA CTT GCG AAC CCG CTT GAG<br>Thr Gln Asp Tyr Thr Gly Ser Asn Arg Leu Leu Ala Asn Pro Leu Glu<br>270                       275                   280                 285 | 966 |
| TAT GGC AGC CAA TCA TGG CTG TTC CGA CCG GGT TGG CAT TTG GAC AAC<br>Tyr Gly Ser Gln Ser Trp Leu Phe Arg Pro Gly Trp His Leu Asp Asn<br>                   290                   295                 300 | 1014 |
| CGC CAT TAT GTC GGA GCC GTT CTC GAA CGT ACG CAG CAG ACC TTT GAT<br>Arg His Tyr Val Gly Ala Val Leu Glu Arg Thr Gln Gln Thr Phe Asp<br>             305                   310                 315 | 1062 |
| ACA CGG GAT ATG ACT GTT CCT GCC TAT TTT ACC AGT GAA GAT TAT GTA<br>Thr Arg Asp Met Thr Val Pro Ala Tyr Phe Thr Ser Glu Asp Tyr Val<br>320                       325                   330 | 1110 |
| CCC GGT TCG CTG AAA GGT CTT GGC AAA TAT TCG GGC GAT AAT AAG GCA<br>Pro Gly Ser Leu Lys Gly Leu Gly Lys Tyr Ser Gly Asp Asn Lys Ala<br>             335                   340                 345 | 1158 |
| GAA AGG CTG TTT GTT CAG GGA GAG GGC AGT ACA TTG CAG GGT ATC GGT<br>Glu Arg Leu Phe Val Gln Gly Glu Gly Ser Thr Leu Gln Gly Ile Gly<br>350                       355                   360                 365 | 1206 |
| TAC GGT ACC GGC GTG TTT TAT GAT GAA CGC CAT ACT AAA AAC CGC TAC<br>Tyr Gly Thr Gly Val Phe Tyr Asp Glu Arg His Thr Lys Asn Arg Tyr<br>             370                   375                 380 | 1254 |
| GGG GTC GAA TAT GTT TAC CAT AAT GCT GAT AAG GAT ACC TGG GCC GAT<br>Gly Val Glu Tyr Val Tyr His Asn Ala Asp Lys Asp Thr Trp Ala Asp<br>                   385                   390                 395 | 1302 |
| TAC GCC CGA CTT TCT TAT GAC CGG CAA GGT ATA GAT TTG GAC AAC CGT<br>Tyr Ala Arg Leu Ser Tyr Asp Arg Gln Gly Ile Asp Leu Asp Asn Arg<br>             400                   405                 410 | 1350 |
| TTG CAG CAG ACG CAT TGC TCT CAC GAC GGT TCG GAT AAA AAT TGC CGT<br>Leu Gln Gln Thr His Cys Ser His Asp Gly Ser Asp Lys Asn Cys Arg<br>                   415                   420                 425 | 1398 |
| CCC GAC GGC AAT AAA CCG TAT TCT TTC TAT AAA TCC GAC CGG ATG ATT<br>Pro Asp Gly Asn Lys Pro Tyr Ser Phe Tyr Lys Ser Asp Arg Met Ile<br>430                       435                   440                 445 | 1446 |
| TAT GAA GAA AGC CGA AAC CTG TTC CAA GCA GTA TTT AAA AAG GCA TTT<br>Tyr Glu Glu Ser Arg Asn Leu Phe Gln Ala Val Phe Lys Lys Ala Phe<br>                   450                   455                 460 | 1494 |

-continued

```
GAT ACG GCC AAA ATC CGT CAC AAT TTG AGT ATC AAT CTA GGG TAC GAC      1542
Asp Thr Ala Lys Ile Arg His Asn Leu Ser Ile Asn Leu Gly Tyr Asp
            465                 470                 475

CGC TTT AAG TCG CAA TTG TCC CAC AGC GAT TAT TAT CTT CAA AAC GCA      1590
Arg Phe Lys Ser Gln Leu Ser His Ser Asp Tyr Tyr Leu Gln Asn Ala
            480                 485                 490

GTT CAG GCA TAT GAT TTG ATA ACC CCG AAA AAG CCT CCG TTT CCC AAC      1638
Val Gln Ala Tyr Asp Leu Ile Thr Pro Lys Lys Pro Pro Phe Pro Asn
            495                 500                 505

GGA AGC AAA GAC AAC CCG TAT AGG GTG TCT ATC GGC AAG ACC ACG GTC      1686
Gly Ser Lys Asp Asn Pro Tyr Arg Val Ser Ile Gly Lys Thr Thr Val
510                 515                 520                 525

AAT ACA TCG CCG ATA TGC CGT TTC GGC AAT AAC ACC TAT ACA GAC TGC      1734
Asn Thr Ser Pro Ile Cys Arg Phe Gly Asn Asn Thr Tyr Thr Asp Cys
            530                 535                 540

ACA CCG AGG AAT ATC GGC GGC AAC GGT TAT TAT GCA GCC GTT CAA GAC      1782
Thr Pro Arg Asn Ile Gly Gly Asn Gly Tyr Tyr Ala Ala Val Gln Asp
            545                 550                 555

AAT GTC CGT TTG GGC AGG TGG GCG GAT GTC GGA GCA GGC ATA CGT TAC      1830
Asn Val Arg Leu Gly Arg Trp Ala Asp Val Gly Ala Gly Ile Arg Tyr
            560                 565                 570

GAT TAC CGC AGC ACG CAT TCG GAA GAT AAG AGT GTC TCT ACC GGC ACT      1878
Asp Tyr Arg Ser Thr His Ser Glu Asp Lys Ser Val Ser Thr Gly Thr
            575                 580                 585

CAC CGC AAC CTT TCT TGG AAC GCG GGC GTA GTC CTC AAA CCT TTC ACC      1926
His Arg Asn Leu Ser Trp Asn Ala Gly Val Val Leu Lys Pro Phe Thr
590                 595                 600                 605

TGG ATG GAT TTG ACT TAT CGC GCT TCT ACG GGC TTC CGT CTG CCG TCG      1974
Trp Met Asp Leu Thr Tyr Arg Ala Ser Thr Gly Phe Arg Leu Pro Ser
            610                 615                 620

TTT GCC GAA ATG TAT GGC TGG AGA GCC GGG GAG TCT TTG AAA ACG TTG      2022
Phe Ala Glu Met Tyr Gly Trp Arg Ala Gly Glu Ser Leu Lys Thr Leu
            625                 630                 635

GAT CTG AAA CCG GAA AAA TCC TTT AAT AGA GAG GCA GGT ATT GTA TTT      2070
Asp Leu Lys Pro Glu Lys Ser Phe Asn Arg Glu Ala Gly Ile Val Phe
            640                 645                 650

AAA GGG GAC TTC GGC AAT TTG GAA GCC AGC TAT TTC AAC AAT GCC TAT      2118
Lys Gly Asp Phe Gly Asn Leu Glu Ala Ser Tyr Phe Asn Asn Ala Tyr
655                 660                 665

CGC GAC CTG ATT GCA TTC GGT TAT GAA ACC CGA ACT CAA AAC GGG CAA      2166
Arg Asp Leu Ile Ala Phe Gly Tyr Glu Thr Arg Thr Gln Asn Gly Gln
670                 675                 680                 685

ACT TCG GCT TCT GGC GAC CCC GGA TAC CGA AAT GCC CAA AAT GCA CGG      2214
Thr Ser Ala Ser Gly Asp Pro Gly Tyr Arg Asn Ala Gln Asn Ala Arg
            690                 695                 700

ATA GCC GGT ATC AAT ATT TTG GGT AAA ATC GAT TGG CAC GGC GTA TGG      2262
Ile Ala Gly Ile Asn Ile Leu Gly Lys Ile Asp Trp His Gly Val Trp
            705                 710                 715

GGC GGG TTG CCG GAC GGG TTG TAT TCC ACG CTT GCC TAT AAC CGT ATC      2310
Gly Gly Leu Pro Asp Gly Leu Tyr Ser Thr Leu Ala Tyr Asn Arg Ile
            720                 725                 730

AAG GTC AAA GAT GCC GAT ATA CGC GCC GAC AGG ACG TTT GTA ACT TCA      2358
Lys Val Lys Asp Ala Asp Ile Arg Ala Asp Arg Thr Phe Val Thr Ser
735                 740                 745

TAT CTC TTT GAT GCC GTC CAA CCT TCA CGA TAT GTA TTG GGT TTG GGT      2406
Tyr Leu Phe Asp Ala Val Gln Pro Ser Arg Tyr Val Leu Gly Leu Gly
750                 755                 760                 765

TAC GAC CAT CCT GAC GGA ATA TGG GGC ATC AAT ACG ATG TTT ACT TAT      2454
Tyr Asp His Pro Asp Gly Ile Trp Gly Ile Asn Thr Met Phe Thr Tyr
```

-continued

```
                   770                 775                 780
TCC AAG GCA AAA TCT GTT GAC GAA CTG CTC GGC AGC CAG GCG CTG TTG     2502
Ser Lys Ala Lys Ser Val Asp Glu Leu Leu Gly Ser Gln Ala Leu Leu
            785                 790                 795

AAC GGT AAT GCC AAT GCT AAA AAA GCA GCA TCA CGG CGG ACG CGG CCT    2550
Asn Gly Asn Ala Asn Ala Lys Lys Ala Ala Ser Arg Arg Thr Arg Pro
                800                 805                 810

TGG TAT GTT ACG GAT GTT TCC GGA TAT TAC AAT ATC AAG AAA CAC CTG    2598
Trp Tyr Val Thr Asp Val Ser Gly Tyr Tyr Asn Ile Lys Lys His Leu
            815                 820                 825

ACC CTG CGC GCA GGT GTG TAC AAC CTC CTC AAC TAC CGC TAT GTT ACT    2646
Thr Leu Arg Ala Gly Val Tyr Asn Leu Leu Asn Tyr Arg Tyr Val Thr
830                 835                 840                 845

TGG GAA AAT GTG CGG CAA ACT GCC GGC GGC GCA GTC AAC CAA CAC AAA    2694
Trp Glu Asn Val Arg Gln Thr Ala Gly Gly Ala Val Asn Gln His Lys
                850                 855                 860

AAT GTC GGC GTT TAC AAC CGA TAT GCC GCC CCC GGC CGA AAC TAC ACA    2742
Asn Val Gly Val Tyr Asn Arg Tyr Ala Ala Pro Gly Arg Asn Tyr Thr
            865                 870                 875

TTT AGC TTG GAA ATG AAG TTT TAAACGTCCA AACGCCGCAA ATGCCGTCTG       2793
Phe Ser Leu Glu Met Lys Phe
        880

AAAGGCT                                                             2800
```

(2) INFORMATION FOR SEQ ID NO:4:

(i) SEQUENCE CHARACTERISTICS:
        (A) LENGTH: 908 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gln Gln Gln His Leu Phe Arg Leu Asn Ile Leu Cys Leu Ser Leu
-24             -20                 -15                 -10

Met Thr Ala Leu Pro Val Tyr Ala Glu Asn Val Gln Ala Glu Gln Ala
            -5                   1                   5

Gln Glu Lys Gln Leu Asp Thr Ile Gln Val Lys Ala Lys Lys Gln Lys
        10                  15                  20

Thr Arg Arg Asp Asn Glu Val Thr Gly Leu Gly Lys Leu Val Lys Ser
 25                  30                  35                  40

Ser Asp Thr Leu Ser Lys Glu Gln Val Leu Asn Ile Arg Asp Leu Thr
                45                  50                  55

Arg Tyr Asp Pro Gly Ile Ala Val Val Glu Gln Gly Arg Gly Ala Ser
            60                  65                  70

Ser Gly Tyr Ser Ile Arg Gly Met Asp Lys Asn Arg Val Ser Leu Thr
        75                  80                  85

Val Asp Gly Val Ser Gln Ile Gln Ser Tyr Thr Ala Gln Ala Ala Leu
    90                  95                  100

Gly Gly Thr Arg Thr Ala Gly Ser Ser Gly Ala Ile Asn Glu Ile Glu
105                 110                 115                 120

Tyr Glu Asn Val Lys Ala Val Glu Ile Ser Lys Gly Ser Asn Ser Ser
                125                 130                 135

Glu Tyr Gly Asn Gly Ala Leu Ala Gly Ser Val Ala Phe Gln Thr Lys
            140                 145                 150

Thr Ala Ala Asp Ile Ile Gly Glu Gly Lys Gln Trp Gly Ile Gln Ser
        155                 160                 165
```

```
Lys Thr Ala Tyr Ser Gly Lys Asp His Ala Leu Thr Gln Ser Leu Ala
    170                 175                 180

Leu Ala Gly Arg Ser Gly Gly Ala Glu Ala Leu Leu Ile Tyr Thr Lys
185                 190                 195                 200

Arg Arg Gly Arg Glu Ile His Ala His Lys Asp Ala Gly Lys Gly Val
                    205                 210                 215

Gln Ser Phe Asn Arg Leu Val Leu Asp Glu Asp Lys Lys Glu Gly Gly
                220                 225                 230

Ser Gln Tyr Arg Tyr Phe Ile Val Glu Glu Cys His Asn Gly Tyr
            235                 240                 245

Ala Ala Cys Lys Asn Lys Leu Lys Glu Asp Ala Ser Val Lys Asp Glu
    250                 255                 260

Arg Lys Thr Val Ser Thr Gln Asp Tyr Thr Gly Ser Asn Arg Leu Leu
265                 270                 275                 280

Ala Asn Pro Leu Glu Tyr Gly Ser Gln Ser Trp Leu Phe Arg Pro Gly
                285                 290                 295

Trp His Leu Asp Asn Arg His Tyr Val Gly Ala Val Leu Glu Arg Thr
                300                 305                 310

Gln Gln Thr Phe Asp Thr Arg Asp Met Thr Val Pro Ala Tyr Phe Thr
            315                 320                 325

Ser Glu Asp Tyr Val Pro Gly Ser Leu Lys Gly Leu Gly Lys Tyr Ser
    330                 335                 340

Gly Asp Asn Lys Ala Glu Arg Leu Phe Val Gln Gly Glu Gly Ser Thr
345                 350                 355                 360

Leu Gln Gly Ile Gly Tyr Gly Thr Gly Val Phe Tyr Asp Glu Arg His
                365                 370                 375

Thr Lys Asn Arg Tyr Gly Val Glu Tyr Val Tyr His Asn Ala Asp Lys
                380                 385                 390

Asp Thr Trp Ala Asp Tyr Ala Arg Leu Ser Tyr Asp Arg Gln Gly Ile
            395                 400                 405

Asp Leu Asp Asn Arg Leu Gln Gln Thr His Cys Ser His Asp Gly Ser
    410                 415                 420

Asp Lys Asn Cys Arg Pro Asp Gly Asn Lys Pro Tyr Ser Phe Tyr Lys
425                 430                 435                 440

Ser Asp Arg Met Ile Tyr Glu Glu Ser Arg Asn Leu Phe Gln Ala Val
                445                 450                 455

Phe Lys Lys Ala Phe Asp Thr Ala Lys Ile Arg His Asn Leu Ser Ile
            460                 465                 470

Asn Leu Gly Tyr Asp Arg Phe Lys Ser Gln Leu Ser His Ser Asp Tyr
    475                 480                 485

Tyr Leu Gln Asn Ala Val Gln Ala Tyr Asp Leu Ile Thr Pro Lys Lys
    490                 495                 500

Pro Pro Phe Pro Asn Gly Ser Lys Asp Asn Pro Tyr Arg Val Ser Ile
505                 510                 515                 520

Gly Lys Thr Thr Val Asn Thr Ser Pro Ile Cys Arg Phe Gly Asn Asn
                525                 530                 535

Thr Tyr Thr Asp Cys Thr Pro Arg Asn Ile Gly Gly Asn Gly Tyr Tyr
            540                 545                 550

Ala Ala Val Gln Asp Asn Val Arg Leu Gly Arg Trp Ala Asp Val Gly
    555                 560                 565

Ala Gly Ile Arg Tyr Asp Tyr Arg Ser Thr His Ser Glu Asp Lys Ser
570                 575                 580
```

```
Val Ser Thr Gly Thr His Arg Asn Leu Ser Trp Asn Ala Gly Val Val
585                 590                 595                 600

Leu Lys Pro Phe Thr Trp Met Asp Leu Thr Tyr Arg Ala Ser Thr Gly
                605                 610                 615

Phe Arg Leu Pro Ser Phe Ala Glu Met Tyr Gly Trp Arg Ala Gly Glu
                620                 625                 630

Ser Leu Lys Thr Leu Asp Leu Lys Pro Glu Lys Ser Phe Asn Arg Glu
                635                 640                 645

Ala Gly Ile Val Phe Lys Gly Asp Phe Gly Asn Leu Glu Ala Ser Tyr
650                 655                 660

Phe Asn Ala Tyr Arg Asp Leu Ile Ala Phe Gly Tyr Glu Thr Arg
665                 670                 675                 680

Thr Gln Asn Gly Gln Thr Ser Ala Ser Gly Asp Pro Gly Tyr Arg Asn
                685                 690                 695

Ala Gln Asn Ala Arg Ile Ala Gly Ile Asn Ile Leu Gly Lys Ile Asp
                700                 705                 710

Trp His Gly Val Trp Gly Gly Leu Pro Asp Gly Leu Tyr Ser Thr Leu
                715                 720                 725

Ala Tyr Asn Arg Ile Lys Val Lys Asp Ala Asp Ile Arg Ala Asp Arg
                730                 735                 740

Thr Phe Val Thr Ser Tyr Leu Phe Asp Ala Val Gln Pro Ser Arg Tyr
745                 750                 755                 760

Val Leu Gly Leu Gly Tyr Asp His Pro Asp Gly Ile Trp Gly Ile Asn
                765                 770                 775

Thr Met Phe Thr Tyr Ser Lys Ala Lys Ser Val Asp Glu Leu Leu Gly
                780                 785                 790

Ser Gln Ala Leu Leu Asn Gly Asn Ala Asn Ala Lys Lys Ala Ala Ser
                795                 800                 805

Arg Arg Thr Arg Pro Trp Tyr Val Thr Asp Val Ser Gly Tyr Tyr Asn
                810                 815                 820

Ile Lys Lys His Leu Thr Leu Arg Ala Gly Val Tyr Asn Leu Leu Asn
825                 830                 835                 840

Tyr Arg Tyr Val Thr Trp Glu Asn Val Arg Gln Thr Ala Gly Gly Ala
                845                 850                 855

Val Asn Gln His Lys Asn Val Gly Val Tyr Asn Arg Tyr Ala Ala Pro
                860                 865                 870

Gly Arg Asn Tyr Thr Phe Ser Leu Glu Met Lys Phe
                875                 880

(2) INFORMATION FOR SEQ ID NO:5:

(i) SEQUENCE CHARACTERISTICS:
        (A) LENGTH: 2809 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: DNA which encodes Tbp1 subunit of transferrin
            receptor
        (B) STRAIN: Neisseria meningitidis IM2169

(ix) FEATURE:
        (A) NAME/KEY: sig_peptide
        (B) LOCATION: 71..142

(ix) FEATURE:
        (A) NAME/KEY: mat_peptide
```

(B) LOCATION: 143..2803

(ix) FEATURE:
    (A) NAME/KEY: CDS
    (B) LOCATION: 71..2803

(xi) SEQUENCE DESCRIPTION: SEQ ID NO:5:

| | | |
|---|---|---|
| ATCAAGAATA AGGCTTCAGA CGGCATCGCT CCTTCCGATA CCGTCTGAAA GCGAAGATTA | 60 | |
| GGGAAACATT ATG CAA CAG CAA CAT TTG TTC CGA TTA AAT ATT TTA TGC<br>     Met Gln Gln Gln His Leu Phe Arg Leu Asn Ile Leu Cys<br>      -24    -20      -15 | 109 | |
| CTG TCG CTG ATG ACT GCG CTG CCT GCT TAT GCA GAA AAT GTG CAA GCC<br>Leu Ser Leu Met Thr Ala Leu Pro Ala Tyr Ala Glu Asn Val Gln Ala<br>  -10      -5       1      5 | 157 | |
| GGA CAA GCA CAG GAA AAA CAG TTG GAT ACC ATA CAG GTA AAA GCC AAA<br>Gly Gln Ala Gln Glu Lys Gln Leu Asp Thr Ile Gln Val Lys Ala Lys<br>      10       15       20 | 205 | |
| AAA CAG AAA ACC CGC CGC GAT AAC GAA GTA ACC GGT CTG GGC AAA TTG<br>Lys Gln Lys Thr Arg Arg Asp Asn Glu Val Thr Gly Leu Gly Lys Leu<br>    25       30       35 | 253 | |
| GTC AAA ACC GCC GAC ACC CTC AGC AAG GAA CAG GTA CTC GAT ATC CGC<br>Val Lys Thr Ala Asp Thr Leu Ser Lys Glu Gln Val Leu Asp Ile Arg<br>    40       45       50 | 301 | |
| GAC CTG ACG CGT TAC GAC CCC GGC ATC GCC GTG GTC GAA CAG GGG CGC<br>Asp Leu Thr Arg Tyr Asp Pro Gly Ile Ala Val Val Glu Gln Gly Arg<br>    55       60       65 | 349 | |
| GGC GCA AGT TCG GGC TAC TCG ATA CGC GGT ATG GAC AAA AAC CGC GTT<br>Gly Ala Ser Ser Gly Tyr Ser Ile Arg Gly Met Asp Lys Asn Arg Val<br>70       75       80       85 | 397 | |
| TCC TTG ACG GTG GAC GGC TTG GCG CAA ATA CAG TCC TAC ACC GCG CAG<br>Ser Leu Thr Val Asp Gly Leu Ala Gln Ile Gln Ser Tyr Thr Ala Gln<br>      90       95       100 | 445 | |
| GCG GCA TTG GGC GGG ACG AGG ACG GCG GGC AGC AGC GGC GCA ATC AAT<br>Ala Ala Leu Gly Gly Thr Arg Thr Ala Gly Ser Ser Gly Ala Ile Asn<br>      105       110       115 | 493 | |
| GAA ATC GAG TAT GAA AAC GTC AAA GCT GTC GAA ATC AGC AAA GGC TCA<br>Glu Ile Glu Tyr Glu Asn Val Lys Ala Val Glu Ile Ser Lys Gly Ser<br>      120       125       130 | 541 | |
| AAC TCG GTC GAA CAA GGC AGC GGC GCA TTG GCG GGT TCG GTC GCA TTT<br>Asn Ser Val Glu Gln Gly Ser Gly Ala Leu Ala Gly Ser Val Ala Phe<br>135       140       145 | 589 | |
| CAA ACC AAA ACC GCC GAC GAT GTT ATC GGG GAA GGC AGG CAG TGG GGC<br>Gln Thr Lys Thr Ala Asp Asp Val Ile Gly Glu Gly Arg Gln Trp Gly<br>150       155       160       165 | 637 | |
| ATT CAG AGT AAA ACC GCC TAT TCC GGC AAA AAC CGG GGG CTT ACC CAA<br>Ile Gln Ser Lys Thr Ala Tyr Ser Gly Lys Asn Arg Gly Leu Thr Gln<br>      170       175       180 | 685 | |
| TCC ATC GCG CTG GCG GGG CGC ATC GGC GGT GCG GAG GCT TTG CTG ATC<br>Ser Ile Ala Leu Ala Gly Arg Ile Gly Gly Ala Glu Ala Leu Leu Ile<br>      185       190       195 | 733 | |
| CAC ACC GGG CGG CGC GCG GGG GAA ATC CGC GCA CAC GAA GAT GCC GGA<br>His Thr Gly Arg Arg Ala Gly Glu Ile Arg Ala His Glu Asp Ala Gly<br>      200       205       210 | 781 | |
| CGC GGC GTT CAG AGC TTT AAC AGG CTG GTG CCG GTT GAA GAC AGC AGC<br>Arg Gly Val Gln Ser Phe Asn Arg Leu Val Pro Val Glu Asp Ser Ser<br>      215       220       225 | 829 | |
| GAA TAC GCC TAT TTC ATC GTT GAA GAT GAA TGC GAA GGC AAA AAT TAC<br>Glu Tyr Ala Tyr Phe Ile Val Glu Asp Glu Cys Glu Gly Lys Asn Tyr<br>230       235       240       245 | 877 | |
| GAA ACG TGT AAA AGC AAA CCG AAA AAA GAT GTT GTC GGC AAA GAC GAA | 925 | |

```
              Glu Thr Cys Lys Ser Lys Pro Lys Lys Asp Val Val Gly Lys Asp Glu
                              250                 255                 260

CGT CAA ACG GTT TCC ACC CGA GAC TAC ACG GGC CCC AAC CGC TTC CTC              973
Arg Gln Thr Val Ser Thr Arg Asp Tyr Thr Gly Pro Asn Arg Phe Leu
            265                 270                 275

GCC GAT CCG CTT TCA TAC GAA AGC CGA TCG TGG CTG TTC CGC CCG GGT             1021
Ala Asp Pro Leu Ser Tyr Glu Ser Arg Ser Trp Leu Phe Arg Pro Gly
        280                 285                 290

TTT CGT TTT GAA AAC AAA CGG CAC TAC ATC GGC GGC ATA CTC GAA CAC             1069
Phe Arg Phe Glu Asn Lys Arg His Tyr Ile Gly Gly Ile Leu Glu His
    295                 300                 305

ACG CAA CAA ACT TTC GAC ACG CGC GAT ATG ACG GTT CCG GCA TTC CTG             1117
Thr Gln Gln Thr Phe Asp Thr Arg Asp Met Thr Val Pro Ala Phe Leu
310                 315                 320                 325

ACC AAG GCG GTT TTT GAT GCA AAT TCA AAA CAG GCG GGT TCT TTG CCC             1165
Thr Lys Ala Val Phe Asp Ala Asn Ser Lys Gln Ala Gly Ser Leu Pro
                330                 335                 340

GGC AAC GGC AAA TAC GCG GGC AAC CAC AAA TAC GGC GGA CTG TTT ACC             1213
Gly Asn Gly Lys Tyr Ala Gly Asn His Lys Tyr Gly Gly Leu Phe Thr
            345                 350                 355

AAC GGC GAA AAC GGT GCG CTG GTG GGC GCG GAA TAC GGT ACG GGC GTG             1261
Asn Gly Glu Asn Gly Ala Leu Val Gly Ala Glu Tyr Gly Thr Gly Val
        360                 365                 370

TTT TAC GAC GAG ACG CAC ACC AAA AGC CGC TAC GGT TTG GAA TAT GTC             1309
Phe Tyr Asp Glu Thr His Thr Lys Ser Arg Tyr Gly Leu Glu Tyr Val
    375                 380                 385

TAT ACC AAT GCC GAT AAA GAC ACT TGG GCG GAT TAT GCC CGC CTC TCT             1357
Tyr Thr Asn Ala Asp Lys Asp Thr Trp Ala Asp Tyr Ala Arg Leu Ser
390                 395                 400                 405

TAC GAC CGG CAG GGC ATC GGT TTG GAC AAT CAT TTT CAG CAG ACG CAC             1405
Tyr Asp Arg Gln Gly Ile Gly Leu Asp Asn His Phe Gln Gln Thr His
                410                 415                 420

TGT TCT GCC GAC GGT TCG GAC AAA TAT TGC CGC CCG AGT GCC GAC AAG             1453
Cys Ser Ala Asp Gly Ser Asp Lys Tyr Cys Arg Pro Ser Ala Asp Lys
            425                 430                 435

CCG TTT TCC TAT TAC AAA TCC GAC CGC GTG ATT TAC GGG GAA AGC CAC             1501
Pro Phe Ser Tyr Tyr Lys Ser Asp Arg Val Ile Tyr Gly Glu Ser His
        440                 445                 450

AGG CTC TTG CAG GCG GCA TTC AAA AAA TCC TTC GAT ACC GCC AAA ATC             1549
Arg Leu Leu Gln Ala Ala Phe Lys Lys Ser Phe Asp Thr Ala Lys Ile
    455                 460                 465

CGC CAC AAC CTG AGC GTG AAT CTC GGG TTT GAC CGC TTT GAC TCT AAT             1597
Arg His Asn Leu Ser Val Asn Leu Gly Phe Asp Arg Phe Asp Ser Asn
470                 475                 480                 485

CTC CGC CAT CAG GAT TAT TAT TAT CAA CAT GCC AAC CGC GCC TAT TCG             1645
Leu Arg His Gln Asp Tyr Tyr Tyr Gln His Ala Asn Arg Ala Tyr Ser
                490                 495                 500

TCG AAA ACG CCC CCT AAA ACC GCC AAC CCC AAC GGC GAC AAG AGC AAA             1693
Ser Lys Thr Pro Pro Lys Thr Ala Asn Pro Asn Gly Asp Lys Ser Lys
            505                 510                 515

CCC TAT TGG GTC AGC ATA GGC GGG GGA AAT GTG GTT ACG GGG CAA ATC             1741
Pro Tyr Trp Val Ser Ile Gly Gly Gly Asn Val Val Thr Gly Gln Ile
        520                 525                 530

TGC CTC TTT GGC AAC AAT ACT TAT ACG GAC TGC ACG CCG CGC AGC ATC             1789
Cys Leu Phe Gly Asn Asn Thr Tyr Thr Asp Cys Thr Pro Arg Ser Ile
    535                 540                 545

AAC GGC AAA AGC TAT TAC GCG GCA GTT CGG GAC AAT GTC CGT TTG GGC             1837
Asn Gly Lys Ser Tyr Tyr Ala Ala Val Arg Asp Asn Val Arg Leu Gly
550                 555                 560                 565
```

```
                                        -continued

AGG TGG GCG GAT GTC GGC GCG GGG TTG CGC TAC GAC TAC CGC AGC ACG      1885
Arg Trp Ala Asp Val Gly Ala Gly Leu Arg Tyr Asp Tyr Arg Ser Thr
            570                 575                 580

CAT TCG GAC GAC GGC AGC GTT TCC ACC GGC ACG CAC CGC ACC CTG TCC      1933
His Ser Asp Asp Gly Ser Val Ser Thr Gly Thr His Arg Thr Leu Ser
        585                 590                 595

TGG AAC GCC GGC ATC GTC CTC AAA CCT GCC GAC TGG CTG GAT TTG ACT      1981
Trp Asn Ala Gly Ile Val Leu Lys Pro Ala Asp Trp Leu Asp Leu Thr
    600                 605                 610

TAC CGC ACT TCA ACC GGC TTC CGC CTG CCC TCG TTT GCG GAA ATG TAC      2029
Tyr Arg Thr Ser Thr Gly Phe Arg Leu Pro Ser Phe Ala Glu Met Tyr
615                 620                 625

GGC TGG CGG TCG GGT GTT CAA AGC AAG GCG GTC AAA ATC GAT CCG GAA      2077
Gly Trp Arg Ser Gly Val Gln Ser Lys Ala Val Lys Ile Asp Pro Glu
630                 635                 640                 645

AAA TCG TTC AAC AAA GAA GCC GGC ATC GTG TTT AAA GGC GAT TTC GGC      2125
Lys Ser Phe Asn Lys Glu Ala Gly Ile Val Phe Lys Gly Asp Phe Gly
            650                 655                 660

AAC TTG GAG GCA AGT TGG TTC AAC AAT GCC TAC CGC GAT TTG ATT GTC      2173
Asn Leu Glu Ala Ser Trp Phe Asn Asn Ala Tyr Arg Asp Leu Ile Val
        665                 670                 675

CGG GGT TAT GAA GCG CAA ATT AAA AAC GGC AAA GAA GAA GCC AAA GGC      2221
Arg Gly Tyr Glu Ala Gln Ile Lys Asn Gly Lys Glu Glu Ala Lys Gly
    680                 685                 690

GAC CCG GCT TAC CTC AAT GCC CAA AGC GCG CGG ATT ACC GGC ATC AAT      2269
Asp Pro Ala Tyr Leu Asn Ala Gln Ser Ala Arg Ile Thr Gly Ile Asn
695                 700                 705

ATT TTG GGC AAA ATC GAT TGG AAC GGC GTA TGG GAT AAA TTG CCC GAA      2317
Ile Leu Gly Lys Ile Asp Trp Asn Gly Val Trp Asp Lys Leu Pro Glu
710                 715                 720                 725

GGT TGG TAT TCT ACA TTT GCC TAT AAT CGT GTC CAT GTC CGC GAC ATC      2365
Gly Trp Tyr Ser Thr Phe Ala Tyr Asn Arg Val His Val Arg Asp Ile
            730                 735                 740

AAA AAA CGC GCA GAC CGC ACC GAT ATT CAA TCA CAC CTG TTT GAT GCC      2413
Lys Lys Arg Ala Asp Arg Thr Asp Ile Gln Ser His Leu Phe Asp Ala
        745                 750                 755

ATC CAA CCC TCG CGC TAT GTC GTC GGC TTG GGC TAT GAC CAA CCG GAA      2461
Ile Gln Pro Ser Arg Tyr Val Val Gly Leu Gly Tyr Asp Gln Pro Glu
    760                 765                 770

GGC AAA TGG GGT GTG AAC GGT ATG CTG ACT TAT TCC AAA GCC AAG GAA      2509
Gly Lys Trp Gly Val Asn Gly Met Leu Thr Tyr Ser Lys Ala Lys Glu
775                 780                 785

ATC ACA GAG TTG TTG GGC AGC CGG GCT TTG CTC AAC GGC AAC AGC CGC      2557
Ile Thr Glu Leu Leu Gly Ser Arg Ala Leu Leu Asn Gly Asn Ser Arg
790                 795                 800                 805

AAT ACA AAA GCC ACC GCG CGC CGT ACC CGC CCT TGG TAT ATT GTG GAT      2605
Asn Thr Lys Ala Thr Ala Arg Arg Thr Arg Pro Trp Tyr Ile Val Asp
            810                 815                 820

GTG TCC GGT TAT TAC ACG ATT AAA AAA CAC TTC ACC CTC CGT GCG GGC      2653
Val Ser Gly Tyr Tyr Thr Ile Lys Lys His Phe Thr Leu Arg Ala Gly
        825                 830                 835

GTG TAC AAC CTC CTC AAC TAC CGC TAT GTT ACT TGG GAA AAT GTG CGG      2701
Val Tyr Asn Leu Leu Asn Tyr Arg Tyr Val Thr Trp Glu Asn Val Arg
    840                 845                 850

CAA ACT GCC GGC GGC GCA GTC AAC CAA CAC AAA AAT GTC GGC GTT TAC      2749
Gln Thr Ala Gly Gly Ala Val Asn Gln His Lys Asn Val Gly Val Tyr
855                 860                 865

AAC CGA TAT GCC GCC CCC GGC CGA AAC TAC ACA TTT AGC TTG GAA ATG      2797
Asn Arg Tyr Ala Ala Pro Gly Arg Asn Tyr Thr Phe Ser Leu Glu Met
870                 875                 880                 885
```

```
AAG TTT TAAACG                                                                                    2809
Lys Phe (2) INFORMATION FOR SEQ ID NO:6:

(i) SEQUENCE CHARACTERISTICS:
        (A) LENGTH: 911 amino acids
        (B) TYPE: amino acid
        (D) TOPOLOGY: linear (ii) MOLECULE TYPE: protein (xi) SEQUENCE DESCRIPTION: SEQ ID NO:6:

Met Gln Gln Gln His Leu Phe Arg Leu Asn Ile Leu Cys Leu Ser Leu
-24              -20                 -15                 -10

Met Thr Ala Leu Pro Ala Tyr Ala Glu Asn Val Gln Ala Gly Gln Ala
            -5              1                   5

Gln Glu Lys Gln Leu Asp Thr Ile Gln Val Lys Ala Lys Lys Gln Lys
        10              15                  20

Thr Arg Arg Asp Asn Glu Val Thr Gly Leu Gly Lys Leu Val Lys Thr
25              30                  35                      40

Ala Asp Thr Leu Ser Lys Glu Gln Val Leu Asp Ile Arg Asp Leu Thr
                45                  50                  55

Arg Tyr Asp Pro Gly Ile Ala Val Val Glu Gln Gly Arg Gly Ala Ser
            60                  65                  70

Ser Gly Tyr Ser Ile Arg Gly Met Asp Lys Asn Arg Val Ser Leu Thr
        75                  80                  85

Val Asp Gly Leu Ala Gln Ile Gln Ser Tyr Thr Ala Gln Ala Ala Leu
    90                  95                  100

Gly Gly Thr Arg Thr Ala Gly Ser Ser Gly Ala Ile Asn Glu Ile Glu
105             110                 115                     120

Tyr Glu Asn Val Lys Ala Val Glu Ile Ser Lys Gly Ser Asn Ser Val
                125                 130                 135

Glu Gln Gly Ser Gly Ala Leu Ala Gly Ser Val Ala Phe Gln Thr Lys
            140                 145                 150

Thr Ala Asp Asp Val Ile Gly Glu Gly Arg Gln Trp Gly Ile Gln Ser
            155                 160                 165

Lys Thr Ala Tyr Ser Gly Lys Asn Arg Gly Leu Thr Gln Ser Ile Ala
170             175                 180

Leu Ala Gly Arg Ile Gly Gly Ala Glu Ala Leu Leu Ile His Thr Gly
185             190                 195                     200

Arg Arg Ala Gly Glu Ile Arg Ala His Glu Asp Ala Gly Arg Gly Val
            205                 210                 215

Gln Ser Phe Asn Arg Leu Val Pro Val Glu Asp Ser Ser Glu Tyr Ala
            220                 225                 230

Tyr Phe Ile Val Glu Asp Glu Cys Glu Gly Lys Asn Tyr Glu Thr Cys
        235                 240                 245

Lys Ser Lys Pro Lys Lys Asp Val Val Gly Lys Asp Glu Arg Gln Thr
        250                 255                 260

Val Ser Thr Arg Asp Tyr Thr Gly Pro Asn Arg Phe Leu Ala Asp Pro
265             270                 275                     280

Leu Ser Tyr Glu Ser Arg Ser Trp Leu Phe Arg Pro Gly Phe Arg Phe
            285                 290                 295

Glu Asn Lys Arg His Tyr Ile Gly Gly Ile Leu Glu His Thr Gln Gln
            300                 305                 310
```

-continued

```
Thr Phe Asp Thr Arg Asp Met Thr Val Pro Ala Phe Leu Thr Lys Ala
            315                 320                 325

Val Phe Asp Ala Asn Ser Lys Gln Ala Gly Ser Leu Pro Gly Asn Gly
        330                 335                 340

Lys Tyr Ala Gly Asn His Lys Tyr Gly Gly Leu Phe Thr Asn Gly Glu
345                 350                 355                 360

Asn Gly Ala Leu Val Gly Ala Glu Tyr Gly Thr Gly Val Phe Tyr Asp
                365                 370                 375

Glu Thr His Thr Lys Ser Arg Tyr Gly Leu Glu Tyr Val Tyr Thr Asn
            380                 385                 390

Ala Asp Lys Asp Thr Trp Ala Asp Tyr Ala Arg Leu Ser Tyr Asp Arg
        395                 400                 405

Gln Gly Ile Gly Leu Asp Asn His Phe Gln Gln Thr His Cys Ser Ala
    410                 415                 420

Asp Gly Ser Asp Lys Tyr Cys Arg Pro Ser Ala Asp Lys Pro Phe Ser
425                 430                 435                 440

Tyr Tyr Lys Ser Asp Arg Val Ile Tyr Gly Glu Ser His Arg Leu Leu
                445                 450                 455

Gln Ala Ala Phe Lys Lys Ser Phe Asp Thr Ala Lys Ile Arg His Asn
            460                 465                 470

Leu Ser Val Asn Leu Gly Phe Asp Arg Phe Asp Ser Asn Leu Arg His
        475                 480                 485

Gln Asp Tyr Tyr Gln His Ala Asn Arg Ala Tyr Ser Ser Lys Thr
    490                 495                 500

Pro Pro Lys Thr Ala Asn Pro Asn Gly Asp Lys Ser Lys Pro Tyr Trp
505                 510                 515                 520

Val Ser Ile Gly Gly Asn Val Val Thr Gly Gln Ile Cys Leu Phe
                525                 530                 535

Gly Asn Asn Thr Tyr Thr Asp Cys Thr Pro Arg Ser Ile Asn Gly Lys
            540                 545                 550

Ser Tyr Tyr Ala Ala Val Arg Asp Asn Val Arg Leu Gly Arg Trp Ala
        555                 560                 565

Asp Val Gly Ala Gly Leu Arg Tyr Asp Tyr Arg Ser Thr His Ser Asp
    570                 575                 580

Asp Gly Ser Val Ser Thr Gly Thr His Arg Thr Leu Ser Trp Asn Ala
585                 590                 595                 600

Gly Ile Val Leu Lys Pro Ala Asp Trp Leu Asp Leu Thr Tyr Arg Thr
                605                 610                 615

Ser Thr Gly Phe Arg Leu Pro Ser Phe Ala Glu Met Tyr Gly Trp Arg
            620                 625                 630

Ser Gly Val Gln Ser Lys Ala Val Lys Ile Asp Pro Glu Lys Ser Phe
        635                 640                 645

Asn Lys Glu Ala Gly Ile Val Phe Lys Gly Asp Phe Gly Asn Leu Glu
    650                 655                 660

Ala Ser Trp Phe Asn Asn Ala Tyr Arg Asp Leu Ile Val Arg Gly Tyr
665                 670                 675                 680

Glu Ala Gln Ile Lys Asn Gly Lys Glu Glu Ala Lys Gly Asp Pro Ala
                685                 690                 695

Tyr Leu Asn Ala Gln Ser Ala Arg Ile Thr Gly Ile Asn Ile Leu Gly
            700                 705                 710

Lys Ile Asp Trp Asn Gly Val Trp Asp Lys Leu Pro Glu Gly Trp Tyr
        715                 720                 725

Ser Thr Phe Ala Tyr Asn Arg Val His Val Arg Asp Ile Lys Lys Arg
```

```
      730                 735                 740
Ala Asp Arg Thr Asp Ile Gln Ser His Leu Phe Asp Ala Ile Gln Pro
745                 750                 755                 760

Ser Arg Tyr Val Val Gly Leu Gly Tyr Asp Gln Pro Glu Gly Lys Trp
                765                 770                 775

Gly Val Asn Gly Met Leu Thr Tyr Ser Lys Ala Lys Glu Ile Thr Glu
                780                 785                 790

Leu Leu Gly Ser Arg Ala Leu Leu Asn Gly Asn Ser Arg Asn Thr Lys
            795                 800                 805

Ala Thr Ala Arg Arg Thr Arg Pro Trp Tyr Ile Val Asp Val Ser Gly
810                 815                 820

Tyr Tyr Thr Ile Lys Lys His Phe Thr Leu Arg Ala Gly Val Tyr Asn
825                 830                 835                 840

Leu Leu Asn Tyr Arg Tyr Val Thr Trp Glu Asn Val Arg Gln Thr Ala
                845                 850                 855

Gly Gly Ala Val Asn Gln His Lys Asn Val Gly Val Tyr Asn Arg Tyr
                860                 865                 870

Ala Ala Pro Gly Arg Asn Tyr Thr Phe Ser Leu Glu Met Lys Phe
            875                 880                 885

(2) INFORMATION FOR SEQ ID NO:7:

(i) SEQUENCE CHARACTERISTICS:
        (A) LENGTH: 2230 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: DNA which encodes Tbp2 subunit of transferrin
            receptor
        (B) STRAIN: Neisseria meningitidis IM2169

(ix) FEATURE:
        (A) NAME/KEY: sig_peptide
        (B) LOCATION: 60..119

(ix) FEATURE:
        (A) NAME/KEY: mat_peptide
        (B) LOCATION: 120..2192

(ix) FEATURE:
        (A) NAME/KEY: CDS
        (B) LOCATION: 60..2192

(xi) SEQUENCE DESCRIPTION: SEQ ID NO:7:

ATTTGTTAAA AATAAATAAA ATAATAATCC TTATCATTCT TAATTGAAT TGGGTTTAT          59

ATG AAC AAT CCA TTG GTA AAT CAG GCT GCT ATG GTG CTG CCT GTG TTT        107
Met Asn Asn Pro Leu Val Asn Gln Ala Ala Met Val Leu Pro Val Phe
-20                 -15                 -10                  -5

TTG TTG AGT GCC TGT CTG GGC GGC GGC GGC AGT TTC GAT CTT GAT TCT        155
Leu Leu Ser Ala Cys Leu Gly Gly Gly Gly Ser Phe Asp Leu Asp Ser
                 1               5                  10

GTC GAT ACC GAA GCC CCG CGT CCC GCG CCA AAG TAT CAA GAT GTT TCT        203
Val Asp Thr Glu Ala Pro Arg Pro Ala Pro Lys Tyr Gln Asp Val Ser
             15                  20                  25

TCC GAA AAA CCG CAA GCC CAA AAA GAC CAA GGC GGA TAC GGT TTT GCG        251
Ser Glu Lys Pro Gln Ala Gln Lys Asp Gln Gly Gly Tyr Gly Phe Ala
         30                  35                  40

ATG AGG TTG AAA CGG AGG AAT TGG TAT CCG GGG GCA GAA GAA AGC GAG        299
Met Arg Leu Lys Arg Arg Asn Trp Tyr Pro Gly Ala Glu Glu Ser Glu
```

```
             45                  50                  55                  60
GTT AAA CTG AAC GAG AGT GAT TGG GAG GCG ACG GGA TTG CCG ACA AAA          347
Val Lys Leu Asn Glu Ser Asp Trp Glu Ala Thr Gly Leu Pro Thr Lys
                         65                  70                  75

CCC AAG GAA CTT CCT AAA CGG CAA AAA TCG GTT ATT GAA AAA GTA GAA          395
Pro Lys Glu Leu Pro Lys Arg Gln Lys Ser Val Ile Glu Lys Val Glu
                 80                  85                  90

ACA GAC GGC GAC AGC GAT ATT TAT TCT TCC CCC TAT CTC ACA CCA TCA          443
Thr Asp Gly Asp Ser Asp Ile Tyr Ser Ser Pro Tyr Leu Thr Pro Ser
             95                  100                 105

AAC CAT CAA AAC GGC AGC GCT GGC AAC GGT GTA AAT CAA CCT AAA AAT          491
Asn His Gln Asn Gly Ser Ala Gly Asn Gly Val Asn Gln Pro Lys Asn
         110                 115                 120

CAG GCA ACA GGT CAC GAA AAT TTC CAA TAT GTT TAT TCC GGT TGG TTT          539
Gln Ala Thr Gly His Glu Asn Phe Gln Tyr Val Tyr Ser Gly Trp Phe
125                 130                 135                 140

TAT AAA CAT GCA GCG AGT GAA AAA GAT TTC AGT AAC AAA AAA ATT AAG          587
Tyr Lys His Ala Ala Ser Glu Lys Asp Phe Ser Asn Lys Lys Ile Lys
                 145                 150                 155

TCA GGC GAC GAT GGT TAT ATC TTC TAT CAC GGT GAA AAA CCT TCC CGA          635
Ser Gly Asp Asp Gly Tyr Ile Phe Tyr His Gly Glu Lys Pro Ser Arg
             160                 165                 170

CAA CTT CCT GCT TCT GGA AAA GTT ATC TAC AAA GGT GTG TGG CAT TTT          683
Gln Leu Pro Ala Ser Gly Lys Val Ile Tyr Lys Gly Val Trp His Phe
         175                 180                 185

GTA ACC GAT ACA AAA AAG GGT CAA GAT TTT CGT GAA ATT ATC CAG CCT          731
Val Thr Asp Thr Lys Lys Gly Gln Asp Phe Arg Glu Ile Ile Gln Pro
     190                 195                 200

TCA AAA AAA CAA GGC GAC AGG TAT AGC GGA TTT TCT GGT GAT GGC AGC          779
Ser Lys Lys Gln Gly Asp Arg Tyr Ser Gly Phe Ser Gly Asp Gly Ser
205                 210                 215                 220

GAA GAA TAT TCC AAC AAA AAG GAA TCC ACG CTG AAA GAT GAT CAC GAG          827
Glu Glu Tyr Ser Asn Lys Lys Glu Ser Thr Leu Lys Asp Asp His Glu
                 225                 230                 235

GGT TAT GGT TTT ACC TCG AAT TTA GAA GTG GAT TTC GGC AAT AAG AAA          875
Gly Tyr Gly Phe Thr Ser Asn Leu Glu Val Asp Phe Gly Asn Lys Lys
             240                 245                 250

TTG ACG GGT AAA TTA ATA CGC AAT AAT GCG AGC CTA AAT AAT AAT ACT          923
Leu Thr Gly Lys Leu Ile Arg Asn Asn Ala Ser Leu Asn Asn Asn Thr
         255                 260                 265

AAT AAT GAC AAA CAT ACC ACC CAA TAC TAC AGC CTT GAT GCA CAA ATA          971
Asn Asn Asp Lys His Thr Thr Gln Tyr Tyr Ser Leu Asp Ala Gln Ile
     270                 275                 280

ACA GGC AAC CGC TTC AAC GGC ACG GCA ACG GCA ACT GAC AAA AAA GAG         1019
Thr Gly Asn Arg Phe Asn Gly Thr Ala Thr Ala Thr Asp Lys Lys Glu
285                 290                 295                 300

AAT GAA ACC AAA CTA CAT CCC TTT GTT TCC GAC TCG TCT TCT TTG AGC         1067
Asn Glu Thr Lys Leu His Pro Phe Val Ser Asp Ser Ser Ser Leu Ser
                 305                 310                 315

GGC GGC TTT TTC GGC CCG CAG GGT GAG GAA TTG GGT TTC CGC TTT TTG         1115
Gly Gly Phe Phe Gly Pro Gln Gly Glu Glu Leu Gly Phe Arg Phe Leu
             320                 325                 330

AGC GAC GAT CAA AAA GTT GCC GGT GTC GGC AGC GCG AAA ACC AAA GAC         1163
Ser Asp Asp Gln Lys Val Ala Gly Val Gly Ser Ala Lys Thr Lys Asp
         335                 340                 345

AAA CTG GAA AAT GGC GCG GCG GCT TCA GGC AGC ACA GGT GCG GCA GCA         1211
Lys Leu Glu Asn Gly Ala Ala Ala Ser Gly Ser Thr Gly Ala Ala Ala
     350                 355                 360

TCG GGC GGT GCG GCA GGC ACG TCG TCT GAA AAC AGT AAG CTG ACC ACG         1259
```

```
Ser Gly Gly Ala Ala Gly Thr Ser Ser Glu Asn Ser Lys Leu Thr Thr
365                 370                 375                 380

GTT TTG GAT GCG GTT GAA TTG ACA CTA AAC GAC AAG AAA ATC AAA AAT    1307
Val Leu Asp Ala Val Glu Leu Thr Leu Asn Asp Lys Lys Ile Lys Asn
                    385                 390                 395

CTC GAC AAC TTC AGC AAT GCC GCC CAA CTG GTT GTC GAC GGC ATT ATG    1355
Leu Asp Asn Phe Ser Asn Ala Ala Gln Leu Val Val Asp Gly Ile Met
                400                 405                 410

ATT CCG CTC CTG CCC AAG GAT TCC GAA AGC GGG AAC ACT CAG GCA GAT    1403
Ile Pro Leu Leu Pro Lys Asp Ser Glu Ser Gly Asn Thr Gln Ala Asp
            415                 420                 425

AAA GGT AAA AAC GGC GGA ACA GAA TTT ACC CGC AAA TTT GAA CAC ACG    1451
Lys Gly Lys Asn Gly Gly Thr Glu Phe Thr Arg Lys Phe Glu His Thr
        430                 435                 440

CCG GAA AGT GAT AAA AAA GAC GCC CAA GCA GGT ACG CAG ACG AAT GGG    1499
Pro Glu Ser Asp Lys Lys Asp Ala Gln Ala Gly Thr Gln Thr Asn Gly
445                 450                 455                 460

GCG CAA ACC GCT TCA AAT ACG GCA GGT GAT ACC AAT GGC AAA ACA AAA    1547
Ala Gln Thr Ala Ser Asn Thr Ala Gly Asp Thr Asn Gly Lys Thr Lys
                    465                 470                 475

ACC TAT GAA GTC GAA GTC TGC TGT TCC AAC CTC AAT TAT CTG AAA TAC    1595
Thr Tyr Glu Val Glu Val Cys Cys Ser Asn Leu Asn Tyr Leu Lys Tyr
                480                 485                 490

GGA ATG TTG ACG CGC AAA AAC AGC AAG TCC GCG ATG CAG GCA GGA GGA    1643
Gly Met Leu Thr Arg Lys Asn Ser Lys Ser Ala Met Gln Ala Gly Gly
            495                 500                 505

AAC AGT AGT CAA GCT GAT GCT AAA ACG GAA CAA GTT GAA CAA AGT ATG    1691
Asn Ser Ser Gln Ala Asp Ala Lys Thr Glu Gln Val Glu Gln Ser Met
        510                 515                 520

TTC CTC CAA GGC GAG CGT ACC GAT GAA AAA GAG ATT CCA ACC GAC CAA    1739
Phe Leu Gln Gly Glu Arg Thr Asp Glu Lys Glu Ile Pro Thr Asp Gln
525                 530                 535                 540

AAC GTC GTT TAT CGG GGG TCT TGG TAC GGG CAT ATT GCC AAC GGC ACA    1787
Asn Val Val Tyr Arg Gly Ser Trp Tyr Gly His Ile Ala Asn Gly Thr
                    545                 550                 555

AGC TGG AGC GGC AAT GCT TCT GAT AAA GAG GGC GGC AAC AGG GCG GAA    1835
Ser Trp Ser Gly Asn Ala Ser Asp Lys Glu Gly Gly Asn Arg Ala Glu
                560                 565                 570

TTT ACT GTG AAT TTT GCC GAT AAA AAA ATT ACC GGC AAG TTA ACC GCT    1883
Phe Thr Val Asn Phe Ala Asp Lys Lys Ile Thr Gly Lys Leu Thr Ala
            575                 580                 585

GAA AAC AGG CAG GCG CAA ACC TTT ACC ATT GAG GGA ATG ATT CAG GGC    1931
Glu Asn Arg Gln Ala Gln Thr Phe Thr Ile Glu Gly Met Ile Gln Gly
        590                 595                 600

AAC GGC TTT GAA GGT ACG GCG AAA ACT GCT GAG TCA GGT TTT GAT CTC    1979
Asn Gly Phe Glu Gly Thr Ala Lys Thr Ala Glu Ser Gly Phe Asp Leu
605                 610                 615                 620

GAT CAA AAA AAT ACC ACC CGC ACG CCT AAG GCA TAT ATC ACA GAT GCC    2027
Asp Gln Lys Asn Thr Thr Arg Thr Pro Lys Ala Tyr Ile Thr Asp Ala
                    625                 630                 635

AAG GTA AAG GGC GGT TTT TAC GGG CCT AAA GCC GAA GAG TTG GGC GGA    2075
Lys Val Lys Gly Gly Phe Tyr Gly Pro Lys Ala Glu Glu Leu Gly Gly
                640                 645                 650

TGG TTT GCC TAT CCG GGC GAT AAA CAA ACG GAA AAG GCA ACA GCT ACA    2123
Trp Phe Ala Tyr Pro Gly Asp Lys Gln Thr Glu Lys Ala Thr Ala Thr
            655                 660                 665

TCC AGC GAT GGA AAT TCA GCA AGC AGC GCG ACC GTG GTA TTC GGT GCG    2171
Ser Ser Asp Gly Asn Ser Ala Ser Ser Ala Thr Val Val Phe Gly Ala
        670                 675                 680
```

```
AAA CGC CAA CAG CCT GTG CAA TAAGCACGGT TGCCGAACAA TCAAGAATAA         2222
Lys Arg Gln Gln Pro Val Gln
685                 690

GGCTTCAG                                                              2230
```

(2) INFORMATION FOR SEQ ID NO:8:

(i) SEQUENCE CHARACTERISTICS:
        (A) LENGTH: 711 amino acids
        (B) TYPE: amino acid
        (D) TOPOLOGY: linear (ii) MOLECULE TYPE: protein (xi) SEQUENCE DESCRIPTION: SEQ ID NO:8:

```
Met Asn Asn Pro Leu Val Asn Gln Ala Ala Met Val Leu Pro Val Phe
-20                 -15                 -10                  -5

Leu Leu Ser Ala Cys Leu Gly Gly Gly Gly Ser Phe Asp Leu Asp Ser
                  1               5                  10

Val Asp Thr Glu Ala Pro Arg Pro Ala Pro Lys Tyr Gln Asp Val Ser
            15                  20                  25

Ser Glu Lys Pro Gln Ala Gln Lys Asp Gln Gly Gly Tyr Gly Phe Ala
        30                  35                  40

Met Arg Leu Lys Arg Arg Asn Trp Tyr Pro Gly Ala Glu Glu Ser Glu
45                  50                  55                  60

Val Lys Leu Asn Glu Ser Asp Trp Glu Ala Thr Gly Leu Pro Thr Lys
                65                  70                  75

Pro Lys Glu Leu Pro Lys Arg Gln Lys Ser Val Ile Glu Lys Val Glu
            80                  85                  90

Thr Asp Gly Asp Ser Asp Ile Tyr Ser Ser Pro Tyr Leu Thr Pro Ser
        95                 100                 105

Asn His Gln Asn Gly Ser Ala Gly Asn Gly Val Asn Gln Pro Lys Asn
    110                 115                 120

Gln Ala Thr Gly His Glu Asn Phe Gln Tyr Val Tyr Ser Gly Trp Phe
125                 130                 135                 140

Tyr Lys His Ala Ala Ser Glu Lys Asp Phe Ser Asn Lys Lys Ile Lys
                145                 150                 155

Ser Gly Asp Asp Gly Tyr Ile Phe Tyr His Gly Glu Lys Pro Ser Arg
            160                 165                 170

Gln Leu Pro Ala Ser Gly Lys Val Ile Tyr Lys Gly Val Trp His Phe
        175                 180                 185

Val Thr Asp Thr Lys Lys Gly Gln Asp Phe Arg Glu Ile Ile Gln Pro
    190                 195                 200

Ser Lys Lys Gln Gly Asp Arg Tyr Ser Gly Phe Ser Gly Asp Gly Ser
205                 210                 215                 220

Glu Glu Tyr Ser Asn Lys Lys Glu Ser Thr Leu Lys Asp Asp His Glu
                225                 230                 235

Gly Tyr Gly Phe Thr Ser Asn Leu Glu Val Asp Phe Gly Asn Lys Lys
            240                 245                 250

Leu Thr Gly Lys Leu Ile Arg Asn Asn Ala Ser Leu Asn Asn Asn Thr
        255                 260                 265

Asn Asn Asp Lys His Thr Thr Gln Tyr Tyr Ser Leu Asp Ala Gln Ile
    270                 275                 280

Thr Gly Asn Arg Phe Asn Gly Thr Ala Thr Ala Thr Asp Lys Lys Glu
285                 290                 295                 300

Asn Glu Thr Lys Leu His Pro Phe Val Ser Asp Ser Ser Ser Leu Ser
```

```
                    305                 310                 315
Gly Gly Phe Phe Gly Pro Gln Gly Glu Leu Gly Phe Arg Phe Leu
                320                 325                 330

Ser Asp Asp Gln Lys Val Ala Gly Val Gly Ser Ala Lys Thr Lys Asp
            335                 340                 345

Lys Leu Glu Asn Gly Ala Ala Ala Ser Gly Ser Thr Gly Ala Ala Ala
350                 355                 360

Ser Gly Gly Ala Ala Gly Thr Ser Ser Glu Asn Ser Lys Leu Thr Thr
365                 370                 375                 380

Val Leu Asp Ala Val Glu Leu Thr Leu Asn Asp Lys Lys Ile Lys Asn
                385                 390                 395

Leu Asp Asn Phe Ser Asn Ala Ala Gln Leu Val Val Asp Gly Ile Met
                400                 405                 410

Ile Pro Leu Leu Pro Lys Asp Ser Glu Ser Gly Asn Thr Gln Ala Asp
                415                 420                 425

Lys Gly Lys Asn Gly Gly Thr Glu Phe Thr Arg Lys Phe Glu His Thr
            430                 435                 440

Pro Glu Ser Asp Lys Lys Asp Ala Gln Ala Gly Thr Gln Thr Asn Gly
445                 450                 455                 460

Ala Gln Thr Ala Ser Asn Thr Ala Gly Asp Thr Asn Gly Lys Thr Lys
                465                 470                 475

Thr Tyr Glu Val Glu Val Cys Cys Ser Asn Leu Asn Tyr Leu Lys Tyr
                480                 485                 490

Gly Met Leu Thr Arg Lys Asn Ser Lys Ser Ala Met Gln Ala Gly Gly
                495                 500                 505

Asn Ser Ser Gln Ala Asp Ala Lys Thr Glu Gln Val Glu Gln Ser Met
510                 515                 520

Phe Leu Gln Gly Glu Arg Thr Asp Glu Lys Glu Ile Pro Thr Asp Gln
525                 530                 535                 540

Asn Val Val Tyr Arg Gly Ser Trp Tyr Gly His Ile Ala Asn Gly Thr
                545                 550                 555

Ser Trp Ser Gly Asn Ala Ser Asp Lys Glu Gly Gly Asn Arg Ala Glu
                560                 565                 570

Phe Thr Val Asn Phe Ala Asp Lys Lys Ile Thr Gly Lys Leu Thr Ala
                575                 580                 585

Glu Asn Arg Gln Ala Gln Thr Phe Thr Ile Glu Gly Met Ile Gln Gly
590                 595                 600

Asn Gly Phe Glu Gly Thr Ala Lys Thr Ala Glu Ser Gly Phe Asp Leu
605                 610                 615                 620

Asp Gln Lys Asn Thr Thr Arg Thr Pro Lys Ala Tyr Ile Thr Asp Ala
                625                 630                 635

Lys Val Lys Gly Gly Phe Tyr Gly Pro Lys Ala Glu Glu Leu Gly Gly
                640                 645                 650

Trp Phe Ala Tyr Pro Gly Asp Lys Gln Thr Glu Lys Ala Thr Ala Thr
                655                 660                 665

Ser Ser Asp Gly Asn Ser Ser Ala Thr Val Val Phe Gly Ala
                670                 675                 680

Lys Arg Gln Gln Pro Val Gln
685                 690
```

(2) INFORMATION FOR SEQ ID NO:9:

(i) SEQUENCE CHARACTERISTICS:
        (A) LENGTH: 51 base pairs (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..51

(ix) FEATURE:
            (A) NAME/KEY: sig_peptide
            (B) LOCATION: 1..51

(xi) SEQUENCE DESCRIPTION: SEQ ID NO:9:

ATG AGG AAA AGA TTT TTT GTG GGA ATA TTC GCG ATA AAC CTC CTT GTT      48
Met Arg Lys Arg Phe Phe Val Gly Ile Phe Ala Ile Asn Leu Leu Val
 1               5                  10                  15

GGA                                                                  51
Gly (2) INFORMATION FOR SEQ ID NO:10:

(i) SEQUENCE CHARACTERISTICS:
            (A) LENGTH: 17 amino acids
            (B) TYPE: amino acid
            (D) TOPOLOGY: linear (ii) MOLECULE TYPE: protein (xi) SEQUENCE DESCRIPTION: SEQ ID NO:10:

Met Arg Lys Arg Phe Phe Val Gly Ile Phe Ala Ile Asn Leu Leu Val
 1               5                  10                  15

Gly (2) INFORMATION FOR SEQ ID NO:11:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..57

(ix) FEATURE:
            (A) NAME/KEY: sig_peptide
            (B) LOCATION: 1..57

(xi) SEQUENCE DESCRIPTION: SEQ ID NO:11:

ATG AAA AAA ATA ACA GGG ATT ATT TTA TTG CTT CTT GCA GTC ATT ATT      48
Met Lys Lys Ile Thr Gly Ile Ile Leu Leu Leu Leu Ala Val Ile Ile
 1               5                  10                  15

CTG TCT GCA                                                          57
Leu Ser Ala (2) INFORMATION FOR SEQ ID NO:12:

(i) SEQUENCE CHARACTERISTICS:
            (A) LENGTH: 19 amino acids
            (B) TYPE: amino acid
            (D) TOPOLOGY: linear (ii) MOLECULE TYPE: protein (xi) SEQUENCE DESCRIPTION: SEQ ID NO:12:

```
Met Lys Lys Ile Thr Gly Ile Ile Leu Leu Leu Ala Val Ile Ile
  1               5                  10                  15

Leu Ser Ala
```

(2) INFORMATION FOR SEQ ID NO:13:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..60

(ix) FEATURE:
        (A) NAME/KEY: sig_peptide
        (B) LOCATION: 1..60

(xi) SEQUENCE DESCRIPTION: SEQ ID NO:13:

```
ATG AAA GCT ACT AAA CTG GTA CTG GGC GCG GTA ATC CTG GGT TCT ACT        48
Met Lys Ala Thr Lys Leu Val Leu Gly Ala Val Ile Leu Gly Ser Thr
  1               5                  10                  15

CTG CTG GCA GGT                                                        60
Leu Leu Ala Gly
            20
```

(2) INFORMATION FOR SEQ ID NO:14:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:14:

```
Met Lys Ala Thr Lys Leu Val Leu Gly Ala Val Ile Leu Gly Ser Thr
  1               5                  10                  15

Leu Leu Ala Gly
            20
```

(2) INFORMATION FOR SEQ ID NO:15:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..69

(ix) FEATURE:
        (A) NAME/KEY: sig_peptide
        (B) LOCATION: 1..69

(xi) SEQUENCE DESCRIPTION: SEQ ID NO:15:

```
ATG AAA CTG ACA ACA CAT CAT CTA CGG ACA GGG GCC GCA TTA TTG GTG        48
Met Lys Leu Thr Thr His His Leu Arg Thr Gly Ala Ala Leu Leu Val
  1               5                  10                  15

GCC GGA ATT CTG CTG GCA GGT                                            69
```

```
Ala Gly Ile Leu Leu Ala Gly
            20
```

(2) INFORMATION FOR SEQ ID NO:16:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:16:

```
Met Lys Leu Thr Thr His His Leu Arg Thr Gly Ala Ala Leu Leu Val
 1               5                  10                  15
Ala Gly Ile Leu Leu Ala Gly
            20
```

(2) INFORMATION FOR SEQ ID NO:17:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..69

(ix) FEATURE:
        (A) NAME/KEY: sig_peptide
        (B) LOCATION: 1..69

(xi) SEQUENCE DESCRIPTION: SEQ ID NO:17:

```
ATG TTT GTA ACG AGC AAA AAA ATG ACC GCG GCT GTT CTG GCA ATT ACT    48
Met Phe Val Thr Ser Lys Lys Met Thr Ala Ala Val Leu Ala Ile Thr
 1               5                  10                  15
TTG GCA ATG TCT CTG AGT GCA                                        69
Leu Ala Met Ser Leu Ser Ala
            20
```

(2) INFORMATION FOR SEQ ID NO:18:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:18:

```
Met Phe Val Thr Ser Lys Lys Met Thr Ala Ala Val Leu Ala Ile Thr
 1               5                  10                  15
Leu Ala Met Ser Leu Ser Ala
            20
```

(2) INFORMATION FOR SEQ ID NO:19:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (genomic)

```
    (ix) FEATURE:
          (A) NAME/KEY: CDS
          (B) LOCATION: 1..63

(ix) FEATURE:
          (A) NAME/KEY: sig_peptide
          (B) LOCATION: 1..63

(xi) SEQUENCE DESCRIPTION: SEQ ID NO:19:

ATG CAA CTG AAC AAA GTG CTG AAA GGG CTG ATG ATT GCT CTG CCT GTT       48
Met Gln Leu Asn Lys Val Leu Lys Gly Leu Met Ile Ala Leu Pro Val
 1               5                  10                  15

ATG GCA ATT GCG GCA                                                   63
Met Ala Ile Ala Ala
                20

(2) INFORMATION FOR SEQ ID NO:20:

(i) SEQUENCE CHARACTERISTICS:
         (A) LENGTH: 21 amino acids
         (B) TYPE: amino acid
         (D) TOPOLOGY: linear (ii) MOLECULE TYPE: protein (xi) SEQUENCE DESCRIPTION: SEQ ID NO:20:

Met Gln Leu Asn Lys Val Leu Lys Gly Leu Met Ile Ala Leu Pro Val
 1               5                  10                  15

Met Ala Ile Ala Ala
                20

(2) INFORMATION FOR SEQ ID NO:21:

(i) SEQUENCE CHARACTERISTICS:
         (A) LENGTH: 54 base pairs
         (B) TYPE: nucleic acid
         (C) STRANDEDNESS: single
         (D) TOPOLOGY: linear (ii) MOLECULE TYPE: DNA (genomic)

(ix) FEATURE:
          (A) NAME/KEY: CDS
          (B) LOCATION: 1..54

(ix) FEATURE:
          (A) NAME/KEY: sig_peptide
          (B) LOCATION: 1..54

(xi) SEQUENCE DESCRIPTION: SEQ ID NO:21:

ATG AGA TAC CTG GCA ACA TTG TTG TTA TCT CTG GCG GTG TTA ATC ACC       48
Met Arg Tyr Leu Ala Thr Leu Leu Leu Ser Leu Ala Val Leu Ile Thr
 1               5                  10                  15

GCC GGG                                                               54
Ala Gly (2) INFORMATION FOR SEQ ID NO:22:

(i) SEQUENCE CHARACTERISTICS:
         (A) LENGTH: 18 amino acids
         (B) TYPE: amino acid
         (D) TOPOLOGY: linear (ii) MOLECULE TYPE: protein (xi) SEQUENCE DESCRIPTION: SEQ ID NO:22:

Met Arg Tyr Leu Ala Thr Leu Leu Leu Ser Leu Ala Val Leu Ile Thr
 1               5                  10                  15
```

Ala Gly (2) INFORMATION FOR SEQ ID NO:23:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..66

(ix) FEATURE:
        (A) NAME/KEY: sig_peptide
        (B) LOCATION: 1..66

(xi) SEQUENCE DESCRIPTION: SEQ ID NO:23:

```
ATG AAA CAT AAC GTT AAG CTG ATG GCA ATG ACT GCC GTT TTA TCC TCT        48
Met Lys His Asn Val Lys Leu Met Ala Met Thr Ala Val Leu Ser Ser
 1               5                  10                  15

GTC CTC GTG CTC TCC GGG                                                 66
Val Leu Val Leu Ser Gly
            20
```

(2) INFORMATION FOR SEQ ID NO:24:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO:24:

```
Met Lys His Asn Val Lys Leu Met Ala Met Thr Ala Val Leu Ser Ser
 1               5                  10                  15

Val Leu Val Leu Ser Gly
            20
```

(2) INFORMATION FOR SEQ ID NO:25:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

```
Glu Xaa Val Gln Ala Glu Gln Ala Gln Glu Lys Gln Leu Asp Thr Ile
 1               5                  10                  15

Gln Val
```

(2) INFORMATION FOR SEQ ID NO:26:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
Xaa Leu Xaa Xaa Xaa Xaa Ser Phe Asp Leu Asp Ser Val Glu Xaa Val
1               5                   10                  15

Gln Xaa Met Xaa
            20
```

(2) INFORMATION FOR SEQ ID NO:27:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
Asn Asn Ile Val Leu Phe Gly Pro Asp Gly Tyr Leu Tyr Tyr Lys
1               5                   10                  15
```

(2) INFORMATION FOR SEQ ID NO:28:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
Tyr Thr Ile Gln Ala
1               5
```

(2) INFORMATION FOR SEQ ID NO:29:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

```
Asp Gly Glu Asn Ala Ala Gly Pro Ala Thr Glu Xaa Val Ile Asp Ala
1               5                   10                  15

Tyr Arg
```

(2) INFORMATION FOR SEQ ID NO:30:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
Xaa Gln Ile Asp Ser Phe Gly Asp Val Lys
1               5                   10
```

(2) INFORMATION FOR SEQ ID NO:31:

(i) SEQUENCE CHARACTERISTICS:
        (A) LENGTH: 7 amino acids
        (B) TYPE: amino acid (C) STRANDEDNESS: single
        (D) TOPOLOGY: linear (ii) MOLECULE TYPE: DNA (genomic)

(xi) SEQUENCE DESCRIPTION: SEQ ID NO:31:

Ala Ala Phe Xaa Xaa Xaa Ile
1               5

(2) INFORMATION FOR SEQ ID NO:32:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

Xaa Asn Xaa Xaa Xaa Met Phe Leu Gln Gly Val Arg
1               5                   10

(2) INFORMATION FOR SEQ ID NO:33:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

Thr Pro Val Ser Asp Val Ala Ala Arg
1               5

(2) INFORMATION FOR SEQ ID NO:34:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

Xaa Ser Pro Ala Phe Thr
1               5

(2) INFORMATION FOR SEQ ID NO:35:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

Asn Ala Ile Glu Met Gly Gly Ser Phe Xaa Phe Pro Gly Asn Ala Pro
1               5                   10                  15

Glu Gly Lys (2) INFORMATION FOR SEQ ID NO:36:

```
        (i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: DNA (genomic)

(xi) SEQUENCE DESCRIPTION: SEQ ID NO:36:

Xaa Gln Pro Glu Ser Gln Gln Asp Val Ser Glu Asn Xaa
1               5                   10

(2) INFORMATION FOR SEQ ID NO:37:

(i) SEQUENCE CHARACTERISTICS:
            (A) LENGTH: 19 amino acids
            (B) TYPE: amino acid
            (C) STRANDEDNESS: single
            (D) TOPOLOGY: linear (ii) MOLECULE TYPE: DNA (genomic)

(xi) SEQUENCE DESCRIPTION: SEQ ID NO:37:

Glu Asn Val Gln Ala Gly Gln Ala Gln Glu Lys Gln Leu Xaa Xaa Ile
1               5                   10                  15

Gln Val Xaa (2) INFORMATION FOR SEQ ID NO:38:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: DNA (genomic)

(ix) FEATURE:
            (A) NAME/KEY: Protein
            (B) LOCATION: 4
            (D) OTHER INFORMATION: /note= "Amino acid 4 is E or W."

(xi) SEQUENCE DESCRIPTION: SEQ ID NO:38:

Xaa Leu Ser Xaa Asn Ala Gly Xaa Val Leu Xaa Pro Ala Asp Xaa
1               5                   10                  15

(2) INFORMATION FOR SEQ ID NO:39:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: DNA (genomic)

(xi) SEQUENCE DESCRIPTION: SEQ ID NO:39:

Gln Leu Asp Thr Ile Gln Val Lys
1               5

(2) INFORMATION FOR SEQ ID NO:40:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: DNA (genomic)
```

(xi) SEQUENCE DESCRIPTION: SEQ ID NO:40:

Thr Ala Gly Ser Ser Gly Ala Ile Asn Glu Ile Glu Tyr Glu Asn Xaa
1               5                   10                  15

Xaa (2) INFORMATION FOR SEQ ID NO:41:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

Tyr Val Thr Trp Glu Asn Val Asp Xaa Xaa Xaa Xaa Xaa Xaa
1               5                   10

(2) INFORMATION FOR SEQ ID NO:42:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

Ser Leu Val Xaa Ala Xaa Ser Phe Asp Leu Xaa Ser Val
1               5                   10

(2) INFORMATION FOR SEQ ID NO:43:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

Xaa Xaa Asp Asn Leu Ser Asn Ala Xaa
1               5

(2) INFORMATION FOR SEQ ID NO:44:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

Xaa Gly Asp Asp Gly Tyr Ile Phe Tyr Xaa Gly Glu Lys Pro Xaa
1               5                   10                  15

(2) INFORMATION FOR SEQ ID NO:45:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

Xaa Gln Gly Xaa Tyr Gly Phe Ala Met Xaa
1               5                   10

(2) INFORMATION FOR SEQ ID NO:46:

(i) SEQUENCE CHARACTERISTICS:
            (A) LENGTH: 19 amino acids
            (B) TYPE: amino acid
            (C) STRANDEDNESS: single
            (D) TOPOLOGY: linear (ii) MOLECULE TYPE: DNA (genomic)

(xi) SEQUENCE DESCRIPTION: SEQ ID NO:46:

Xaa Gln Ala Thr Gly His Glu Asn Phe Gln Tyr Val Tyr Ser Gly Xaa
1               5                   10                  15

Phe Tyr Lys (2) INFORMATION FOR SEQ ID NO:47:

(i) SEQUENCE CHARACTERISTICS:
            (A) LENGTH: 85 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:47:

AAATACCTAT TGCCTACGGC AGCCGCTGGA CTGTTATTAC TCGCTGCCCA ACCAGCGATG      60

GCATGCTTTC CCACGCGTTT TCCCA                                           85

(2) INFORMATION FOR SEQ ID NO:48:

(i) SEQUENCE CHARACTERISTICS:
            (A) LENGTH: 89 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:48:

AGCTTGGGAA AACGCGTGGG AAAGCATGCC ATCGCTGGTT GGGCAGCGAG TAATAACAGT      60

CCAGCGGCTG CCGTAGGCAA TAGGTATTT                                       89

(2) INFORMATION FOR SEQ ID NO:49:

(i) SEQUENCE CHARACTERISTICS:
            (A) LENGTH: 93 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..66

(xi) SEQUENCE DESCRIPTION: SEQ ID NO:49:

ATG AAA TAC CTA TTG CCT ACG GCA GCC GCT GGA CTG TTA TTA CTC GCT        48
Met Lys Tyr Leu Leu Pro Thr Ala Ala Ala Gly Leu Leu Leu Leu Ala

```
              1           5              10              15
GCC CAA CCA GCG ATG GCA TGCTTTCCCA CGCGTTTTCC CAAGCTT              93
Ala Gln Pro Ala Met Ala
            20
```

(2) INFORMATION FOR SEQ ID NO:50:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

```
AAAAAGGATC CGCATGCCTG GGTGGCGGCG GCAGTTTC                          38
```

(2) INFORMATION FOR SEQ ID NO:51:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

```
AAAAGGATCC GAATGGTGTA ACGCGTAGTT TTTAT                             35
```

(2) INFORMATION FOR SEQ ID NO:52:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

```
CATGGCTGCA GGRACCACGC GTGAATTCCC CGGGTCTAGA                        40
```

(2) INFORMATION FOR SEQ ID NO:53:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

```
AGCTTCTAGA CCCGGGGAAT TCACGCGTGG TACCTGCAGC                        40
```

(2) INFORMATION FOR SEQ ID NO:54:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS (B) LOCATION: 15..26

(xi) SEQUENCE DESCRIPTION: SEQ ID NO:54:

TTTCCCGGAT CCGC ATG CAA CAG CAA CATTTGTTCC GATTA                    41
                Met Gln Gln Gln
                  1

(2) INFORMATION FOR SEQ ID NO:55:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

AAAAGGATCC GGGGTCGTAA CGCGTCAGGT CGCGG                              35

(2) INFORMATION FOR SEQ ID NO:56:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

GGCTTTGCGC TGGATCCGCA AAATACC                                       27

(2) INFORMATION FOR SEQ ID NO:57:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

CCCAAAAGAT CTCCAAGCTT GAAGCCTTAT TCTCGATTGT TCGGCAGCC               49

(2) INFORMATION FOR SEQ ID NO:58:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 15..83

(xi) SEQUENCE DESCRIPTION: SEQ ID NO:58:

TTTTTTGGAT CCTC ATG AAC AAT CCA TTG GTA AAT CAG GCT GCT ATG GTG     50
                Met Asn Asn Pro Leu Val Asn Gln Ala Ala Met Val
                  1               5                  10

CTG CCT GTG TTT TTG TTG AGT GCA TGC CTG GGT                         83
Leu Pro Val Phe Leu Leu Ser Ala Cys Leu Gly
         15                  20

(2) INFORMATION FOR SEQ ID NO:59:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

```
TTTTTTGGAT CCGATATCCG TCAGGTCCAA AAAGAACTAT ATTATTC                 47
```

(2) INFORMATION FOR SEQ ID NO:60:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 9..71

(xi) SEQUENCE DESCRIPTION: SEQ ID NO:60:

```
TTTTTTTC ATG AGA TAC CTG GCA ACA TTG TTG TTA TCT CTG GCG GTG TTA    50
         Met Arg Tyr Leu Ala Thr Leu Leu Leu Ser Leu Ala Val Leu
          1               5                  10

ATC ACC GCC GGG TGC CTG GGT GGC                                     74
Ile Thr Ala Gly Cys Leu Gly
 15              20
```

(2) INFORMATION FOR SEQ ID NO:61:

(i) SEQUENCE CHARACTERISTICS:
        (A) LENGTH: 578 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

```
Cys Leu Gly Gly Gly Gly Ser Phe Asp Leu Asp Ser Val Glu Thr Val
 1               5                  10                  15

Gln Asp Met His Ser Lys Pro Lys Tyr Glu Asp Glu Lys Ser Gln Pro
                20                  25                  30

Glu Ser Gln Gln Asp Val Ser Glu Asn Ser Gly Ala Ala Tyr Gly Phe
            35                  40                  45

Ala Val Lys Leu Pro Arg Arg Asn Ala His Phe Asn Pro Lys Tyr Lys
         50                  55                  60

Glu Lys His Lys Pro Leu Gly Ser Met Asp Trp Lys Lys Leu Gln Arg
 65                  70                  75                  80

Gly Glu Pro Asn Ser Phe Ser Glu Arg Asp Glu Leu Glu Lys Lys Arg
                 85                  90                  95

Gly Ser Ser Glu Leu Ile Glu Ser Lys Trp Glu Asp Gly Gln Ser Arg
            100                 105                 110

Val Val Gly Tyr Thr Asn Phe Thr Tyr Val Arg Ser Gly Tyr Val Tyr
        115                 120                 125

Leu Asn Lys Asn Asn Ile Asp Ile Lys Asn Asn Ile Val Leu Phe Gly
    130                 135                 140
```

-continued

```
Pro Asp Gly Tyr Leu Tyr Tyr Lys Gly Lys Glu Pro Ser Lys Glu Leu
145                 150                 155                 160

Pro Ser Glu Lys Ile Thr Tyr Lys Gly Thr Trp Asp Tyr Val Thr Asp
                165                 170                 175

Ala Met Glu Lys Gln Arg Phe Glu Gly Gly Ser Ala Ala Gly Gly Asp
            180                 185                 190

Lys Ser Gly Ala Leu Ser Ala Leu Glu Glu Gly Val Leu Arg Asn Gln
        195                 200                 205

Ala Glu Ala Ser Ser Gly His Thr Asp Phe Gly Met Thr Ser Glu Phe
    210                 215                 220

Glu Val Asp Phe Ser Asp Lys Thr Ile Lys Gly Thr Leu Tyr Arg Asn
225                 230                 235                 240

Asn Arg Ile Thr Gln Asn Asn Ser Glu Asn Lys Gln Ile Lys Thr Thr
                245                 250                 255

Arg Tyr Thr Ile Gln Ala Thr Leu His Gly Asn Arg Phe Lys Gly Lys
            260                 265                 270

Ala Leu Ala Ala Asp Lys Gly Ala Thr Asn Gly Ser His Pro Phe Ile
        275                 280                 285

Ser Asp Ser Asp Ser Leu Glu Gly Gly Phe Tyr Gly Pro Lys Gly Glu
    290                 295                 300

Glu Leu Ala Gly Lys Phe Leu Ser Asn Asp Asn Lys Val Ala Ala Val
305                 310                 315                 320

Phe Gly Ala Lys Gln Lys Asp Lys Lys Asp Gly Glu Asn Ala Ala Gly
                325                 330                 335

Pro Ala Thr Glu Thr Val Ile Asp Ala Tyr Arg Ile Thr Gly Glu Glu
            340                 345                 350

Phe Lys Lys Glu Gln Ile Asp Ser Phe Gly Asp Val Lys Lys Leu Leu
        355                 360                 365

Val Asp Gly Val Glu Leu Ser Leu Leu Pro Ser Glu Gly Asn Lys Ala
    370                 375                 380

Ala Phe Gln His Glu Ile Glu Gln Asn Gly Val Lys Ala Thr Val Cys
385                 390                 395                 400

Cys Ser Asn Leu Asp Tyr Met Ser Phe Gly Lys Leu Ser Lys Glu Asn
                405                 410                 415

Lys Asp Asp Met Phe Leu Gln Gly Val Arg Thr Pro Val Ser Asp Val
            420                 425                 430

Ala Ala Arg Thr Glu Ala Asn Ala Lys Tyr Arg Gly Thr Trp Tyr Gly
        435                 440                 445

Tyr Ile Ala Asn Gly Thr Ser Trp Ser Gly Glu Ala Ser Asn Gln Glu
    450                 455                 460

Gly Gly Asn Arg Ala Glu Phe Asp Val Asp Phe Ser Thr Lys Lys Ile
465                 470                 475                 480

Ser Gly Thr Leu Thr Ala Lys Asp Arg Thr Ser Pro Ala Phe Thr Ile
                485                 490                 495

Thr Ala Met Ile Lys Asp Asn Gly Phe Ser Gly Val Ala Lys Thr Gly
            500                 505                 510

Glu Asn Gly Phe Ala Leu Asp Pro Gln Asn Thr Gly Asn Ser His Tyr
        515                 520                 525

Thr His Ile Glu Ala Thr Val Ser Gly Gly Phe Tyr Gly Lys Asn Ala
    530                 535                 540

Ile Glu Met Gly Gly Ser Phe Ser Phe Pro Gly Asn Ala Pro Glu Gly
545                 550                 555                 560
```

```
Lys Gln Glu Lys Ala Ser Val Val Phe Gly Ala Lys Arg Gln Gln Leu
                565                 570                 575

Val Gln (2) INFORMATION FOR SEQ ID NO:62:

(i) SEQUENCE CHARACTERISTICS:
        (A) LENGTH: 692 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

Cys Leu Gly Gly Gly Ser Phe Asp Leu Asp Ser Val Asp Thr Glu
1               5                   10                  15

Ala Arg Pro Arg Pro Ala Pro Lys Tyr Gln Asp Val Ser Ser Glu Lys
                20                  25                  30

Pro Gln Ala Gln Lys Asp Gln Gly Gly Tyr Gly Phe Ala Met Arg Leu
                35                  40                  45

Lys Arg Arg Asn Trp Tyr Pro Gly Ala Glu Glu Ser Glu Val Lys Leu
50                  55                  60

Asn Glu Ser Asp Trp Glu Ala Thr Gly Leu Pro Thr Lys Pro Lys Glu
65                  70                  75                  80

Leu Pro Lys Arg Gln Lys Ser Val Ile Glu Lys Val Glu Thr Asp Gly
                85                  90                  95

Asp Ser Asp Ile Tyr Ser Ser Pro Tyr Leu Thr Pro Ser Asn His Gln
                100                 105                 110

Asn Gly Ser Ala Gly Asn Gly Val Asn Gln Pro Lys Asn Gln Ala Thr
                115                 120                 125

Gly His Glu Asn Phe Gln Tyr Val Tyr Ser Gly Trp Phe Tyr Lys His
                130                 135                 140

Ala Ala Ser Glu Lys Asp Phe Ser Asn Lys Ile Lys Ser Gly Asp
145                 150                 155                 160

Asp Gly Tyr Ile Phe Tyr His Gly Glu Lys Pro Ser Arg Gln Leu Pro
                165                 170                 175

Ala Ser Gly Lys Val Ile Tyr Lys Gly Val Trp His Phe Val Thr Asp
                180                 185                 190

Thr Lys Lys Gly Gln Asp Phe Arg Glu Ile Ile Gln Pro Ser Lys Lys
                195                 200                 205

Gln Gly Asp Arg Tyr Ser Gly Phe Ser Gly Asp Gly Ser Glu Glu Tyr
                210                 215                 220

Ser Asn Lys Asn Glu Ser Thr Leu Lys Asp Asp His Glu Gly Tyr Gly
225                 230                 235                 240

Phe Thr Ser Asn Leu Glu Val Asp Phe Gly Asn Lys Lys Leu Thr Gly
                245                 250                 255

Lys Leu Ile Arg Asn Asn Ala Ser Leu Asn Asn Thr Asn Asn Asp
                260                 265                 270

Lys His Thr Thr Gln Tyr Tyr Ser Leu Asp Ala Gln Ile Thr Gly Asn
                275                 280                 285

Arg Phe Asn Gly Thr Ala Thr Ala Thr Asp Lys Lys Glu Asn Glu Thr
                290                 295                 300

Lys Leu His Pro Phe Val Ser Asp Ser Ser Ser Leu Ser Gly Gly Phe
305                 310                 315                 320

Phe Gly Pro Gln Gly Glu Glu Leu Gly Phe Arg Phe Leu Ser Asp Asp
```

-continued

```
                325                 330                 335

Gln Lys Val Ala Val Val Gly Ser Ala Lys Thr Lys Asp Lys Leu Glu
            340                 345                 350

Asn Gly Ala Ala Ala Ser Gly Ser Thr Gly Ala Ala Ala Ser Gly Gly
        355                 360                 365

Ala Ala Gly Thr Ser Ser Glu Asn Ser Lys Leu Thr Thr Val Leu Asp
    370                 375                 380

Ala Val Glu Leu Thr Leu Asn Asp Lys Lys Ile Lys Asn Leu Asp Asn
385                 390                 395                 400

Phe Ser Asn Ala Ala Gln Leu Val Val Asp Gly Ile Met Ile Pro Leu
                405                 410                 415

Leu Pro Lys Asp Ser Glu Ser Gly Asn Thr Gln Ala Asp Lys Gly Lys
            420                 425                 430

Asn Gly Gly Thr Glu Phe Thr Arg Lys Phe Glu His Thr Pro Glu Ser
        435                 440                 445

Asp Lys Lys Asp Ala Gln Ala Gly Thr Gln Thr Asn Gly Ala Gln Thr
    450                 455                 460

Ala Ser Asn Thr Ala Gly Asp Thr Asn Gly Lys Thr Lys Thr Tyr Glu
465                 470                 475                 480

Val Glu Val Cys Cys Ser Asn Leu Asn Tyr Leu Lys Tyr Gly Met Leu
                485                 490                 495

Thr Arg Lys Asn Ser Lys Ser Ala Met Gln Ala Gly Gly Asn Ser Ser
            500                 505                 510

Gln Ala Asp Ala Lys Thr Glu Gln Val Glu Gln Ser Met Phe Leu Gln
        515                 520                 525

Gly Glu Arg Thr Asp Glu Lys Glu Ile Pro Thr Asp Gln Asn Val Val
    530                 535                 540

Tyr Arg Gly Ser Trp Tyr Gly His Ile Ala Asn Gly Thr Ser Trp Ser
545                 550                 555                 560

Gly Asn Ala Ser Asp Lys Glu Gly Gly Asn Arg Ala Glu Phe Thr Val
                565                 570                 575

Asn Phe Ala Asp Lys Lys Ile Thr Gly Lys Leu Thr Ala Glu Asn Arg
            580                 585                 590

Gln Ala Gln Thr Phe Thr Ile Glu Gly Met Ile Gln Gly Asn Gly Phe
        595                 600                 605

Glu Gly Thr Ala Lys Thr Ala Glu Ser Gly Phe Asp Leu Asp Gln Lys
    610                 615                 620

Asn Thr Thr Arg Thr Pro Lys Ala Tyr Ile Thr Asp Ala Lys Val Lys
625                 630                 635                 640

Gly Gly Phe Tyr Gly Pro Lys Ala Glu Glu Leu Gly Gly Trp Phe Ala
                645                 650                 655

Tyr Pro Gly Asp Lys Gln Thr Glu Lys Ala Thr Ala Thr Ser Ser Asp
            660                 665                 670

Gly Asn Ser Ala Ser Ser Ala Thr Val Val Phe Gly Ala Lys Arg Gln
        675                 680                 685

Gln Pro Val Gln
    690
```